(12) United States Patent
Bhonoah et al.

(10) Patent No.: US 9,693,556 B2
(45) Date of Patent: Jul. 4, 2017

(54) HERBICIDAL PYRIDAZINONE DERIVATIVES

(71) Applicant: SYNGENTA LIMITED, Guildford (GB)

(72) Inventors: Yunas Bhonoah, Bracknell (GB); Alison Clare Elliott, Bracknell (GB); Steven Gaulier, Bracknell (GB); Kenneth Ling, Bracknell (GB); Glynn Mitchell, Bracknell (GB); James Alan Morris, Bracknell (GB); Paula Rocha Rzepa, Bracknell (GB); Russell Colin Viner, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 0 days.

(21) Appl. No.: 14/349,972

(22) PCT Filed: Oct. 3, 2012

(86) PCT No.: PCT/EP2012/069543
§ 371 (c)(1),
(2) Date: Apr. 7, 2014

(87) PCT Pub. No.: WO2013/050421
PCT Pub. Date: Apr. 11, 2013

(65) Prior Publication Data
US 2014/0256546 A1 Sep. 11, 2014

(30) Foreign Application Priority Data
Oct. 4, 2011 (GB) .................................. 1117019.8

(51) Int. Cl.
| | | |
|---|---|---|
| *A61K 31/51* | (2006.01) | |
| *C07D 401/00* | (2006.01) | |
| *A01N 43/58* | (2006.01) | |
| *C07D 237/16* | (2006.01) | |
| *C07D 401/04* | (2006.01) | |
| *C07D 401/14* | (2006.01) | |
| *C07D 405/04* | (2006.01) | |
| *C07D 405/12* | (2006.01) | |

(Continued)

(52) U.S. Cl.
CPC ............. *A01N 43/58* (2013.01); *A01N 43/60* (2013.01); *A01N 43/653* (2013.01); *A01N 43/80* (2013.01);
(Continued)

(58) Field of Classification Search
CPC .. C07D 237/16; C07D 401/04; C07D 401/14; C07D 405/04; C07D 405/12;
(Continued)

(56) References Cited

U.S. PATENT DOCUMENTS 8,507,410 B2 * 8/2013 Fusaka ................... A01N 43/58
504/238
8,541,414 B2 * 9/2013 Kiji ......................... A01N 43/58
504/238
(Continued)

FOREIGN PATENT DOCUMENTS

JP 11152273 6/1999
JP 11152273 A * 6/1999

OTHER PUBLICATIONS

CAS Abstract of JP 11152273 (1999).*
(Continued)

*Primary Examiner* — Alexander R Pagano
(74) *Attorney, Agent, or Firm* — James Cueva

(57) ABSTRACT

The present invention provides a compound of Formula (I) or an agronomically acceptable salt thereof, wherein: $R^2$ is selected from the group consisting of (A1), (A2) and (A3) wherein $X^1$ is N or $CR^7 X^2$ is N or $CR^8 X^3$ is N or $CR^9 X^4$ is N or $CR^6 R^1$, $R^3$, $R^4$, $R^5$ $R^6$, $R^7$, $R^8$ and $R^9$ are as defined herein. The invention further relates to herbicidal compositions which comprise a compound of Formula (I), and to their use for controlling weeds, in particular in crops of useful plants.

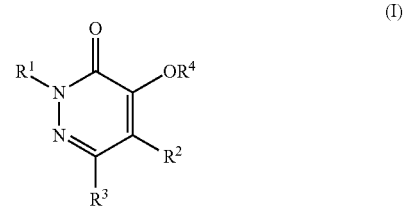

(I)

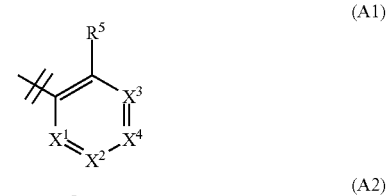

(A1)

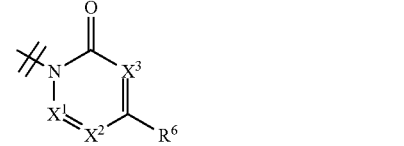

(A2)

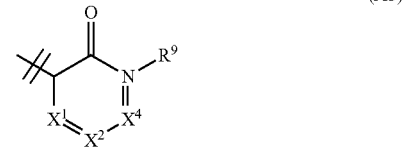

(A3)

13 Claims, No Drawings

(51) Int. Cl.
    *C07D 405/14* (2006.01)
    *C07D 409/14* (2006.01)
    *C07D 413/10* (2006.01)
    *C07D 413/14* (2006.01)
    *C07D 417/04* (2006.01)
    *C07D 471/04* (2006.01)
    *C07D 495/10* (2006.01)
    *A01N 43/60* (2006.01)
    *A01N 43/653* (2006.01)
    *A01N 43/80* (2006.01)
    *A01N 43/90* (2006.01)
    *A01N 43/84* (2006.01)

(52) U.S. Cl.
    CPC ............ *A01N 43/84* (2013.01); *A01N 43/90* (2013.01); *C07D 237/16* (2013.01); *C07D 401/04* (2013.01); *C07D 401/14* (2013.01); *C07D 405/04* (2013.01); *C07D 405/12* (2013.01); *C07D 405/14* (2013.01); *C07D 409/14* (2013.01); *C07D 413/10* (2013.01); *C07D 413/14* (2013.01); *C07D 417/04* (2013.01); *C07D 471/04* (2013.01); *C07D 495/10* (2013.01)

(58) Field of Classification Search
    CPC .. C07D 405/14; C07D 409/14; C07D 413/10; C07D 413/14; C07D 417/04; C07D 471/04; C07D 495/10; A01N 43/58; A01N 43/60; A01N 43/653; A01N 43/80; A01N 43/84; A01N 43/90
    USPC ...................... 514/252.01; 544/238
    See application file for complete search history.

(56) References Cited

U.S. PATENT DOCUMENTS

| | | | | |
|---|---|---|---|---|
| 8,962,625 B2* | 2/2015 | Kiji | ........................ | A01N 43/58 514/247 |
| 9,049,864 B2* | 6/2015 | Burton | ................ | C07D 403/04 |
| 9,096,533 B2* | 8/2015 | Kiji | ........................ | A01N 43/58 |
| 9,096,534 B2* | 8/2015 | Kiji | ........................ | A01N 43/58 |
| 2008/0139390 A1* | 6/2008 | Plant | .................... | C07D 261/10 504/103 |
| 2009/0111696 A1* | 4/2009 | Kiji | ........................ | A01N 43/58 504/238 |
| 2012/0028803 A1* | 2/2012 | Fusaka | ................ | C07D 237/16 504/238 |
| 2012/0028988 A1* | 2/2012 | Sakamoto | .............. | A01N 43/58 514/252.03 |
| 2012/0196750 A1* | 8/2012 | Kiji | ........................ | A01N 43/58 504/238 |
| 2015/0031540 A1* | 1/2015 | Burton | ................ | C07D 403/04 504/237 |
| 2015/0126738 A1* | 5/2015 | Kiji | ........................ | A01N 43/58 544/240 |
| 2015/0126739 A1* | 5/2015 | Kiji | ........................ | A01N 43/58 544/240 |
| 2016/0068509 A1* | 3/2016 | Stevenson et al. | .... | A01N 43/58 504/103 |
| 2016/0272613 A1* | 9/2016 | Braun et al. | ......... | C07D 405/14 |
| 2016/0326135 A1* | 11/2016 | Braun et al. | ......... | C07D 405/14 |

OTHER PUBLICATIONS

L. M. Abell et al. Target-Site Directed Herbicide Design in, Pest Control With Enhanced Environmental Safety 15-37 (ACS Symposium Series; American Chemical Society, S. Duke, et al. eds, 1993).*
S.C. Knight et al., Annual Review of Phytopathology 35, 349-372, 357 (1997).*
W.T. Ruegg et al., Weed Research, 47(4), 271-275, 271 (2006).*
B. Maes et al., 58 Tetrahedron, 9713-9712 (2002).*
Maes B U W et al: "Synthesis of 4-aryl-5-hydroxy- and 5-aryl-4-hydroxypyridazin-3(2H)-ones and their use in the preparation of 4,5-diarylpyridazin-3(2H)-ones and hitherto unknown isochromeno [3,4-d]pyridazinediones", Tetrahedron, Elsevier Science Publishers, Amsterdam, NL, vol. 58, No. 48, Nov. 25, 2002, pp. 9713-9721.
International Search Report prepared for PCT/EP2012/069543, competed Oct. 23, 2012.

* cited by examiner

HERBICIDAL PYRIDAZINONE DERIVATIVES

This application is a 371 of International Application No. PCT/EP2012/069543 filed Oct. 3, 2012, which claims priority to GB 1117019.8, filed Oct. 4, 2011, the contents of which are incorporated herein by reference.

The present invention relates to novel pyridazinone derivatives, to processes for their preparation, to herbicidal compositions which comprise the novel derivatives, and to their use for controlling weeds, in particular in crops of useful plants, or for inhibiting plant growth.

Thus, according to the present invention there is provided a compound of Formula (I):

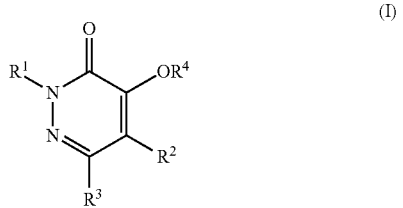

(I)

or an agronomically acceptable salt thereof,
wherein:—
$R^1$ is selected from the group consisting of hydrogen, $C_1$-$C_6$alkyl, $C_3$-$C_6$cycloalkyl, $C_2$-$C_6$alkenyl, $C_2$-$C_6$alkynyl, $C_1$-$C_6$haloalkyl, $C_1$-$C_6$alkoxy-$C_1$-$C_3$-alkyl, $C_3$-$C_6$cycloalkyl$C_1$-$C_3$-alkyl, tetrahydropyranyl- and benzyl-, wherein the benzyl is optionally substituted by one or more $R^{11}$;
$R^2$ is selected from the group consisting of A1, A2 and A3

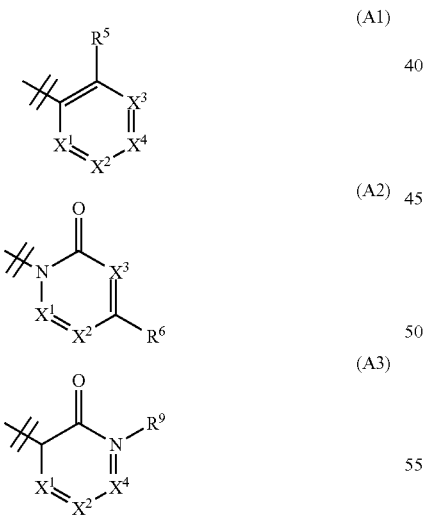

wherein
$X^1$ is N or $CR^7$;
$X^2$ is N or $CR^8$;
$X^3$ is N or $CR^9$;
$X^4$ is N or $CR^6$;
$R^3$ is selected from the group consisting of hydrogen, hydroxyl, halo, nitro, amino, cyano, $C_1$-$C_6$alkyl, $C_1$-$C_3$alkoxy-, $C_3$-$C_6$cycloalkyl, $C_2$-$C_6$alkenyl, $C_2$-$C_6$alkynyl, $C_1$-$C_6$haloalkyl, $C_1$-$C_6$alkoxy-$C_1$-$C_3$-alkyl, $C_3$-$C_6$cycloalkyl-$C_1$-$C_3$-alkyl, $C_1$-$C_6$alkyl-S(O)$_p$—, $C_1$-$C_6$alkyl-S(O)$_p$—$C_1$-$C_3$-alkyl, $C_1$-$C_6$haloalkyl-S(O)$_p$—, $C_1$-$C_3$alkylamino, $C_1$-$C_3$dialkylamino and $C_1$-$C_6$haloalkyl-S(O)$_p$—$C_1$-$C_3$-alkyl;
$R^4$ is selected from the group consisting of hydrogen, $C_1$-$C_6$alkylcarbonyl-, arylcarbonyl-, $C_1$-$C_6$alkoxycarbonyl-, $C_1$-$C_6$alkyl-S(O)$_p$—, $C_1$-$C_6$alkyl-S(O)$_p$carbonyl- and aryl-S(O)$_p$—, wherein said aryl groups may be optionally substituted by one or more $R^{11}$;
$R^5$ is selected from the group consisting of hydroxyl, halogen, $C_1$-$C_6$alkyl, $C_1$-$C_6$cycloalkyl, $C_1$-$C_6$haloalkyl, $C_2$-$C_6$alkenyl, $C_2$-$C_6$haloalkenyl, $C_2$-$C_6$alkynyl, $C_1$-$C_6$ alkoxy-, $C_2$-$C_6$ alkenyloxy-, $C_3$-$C_6$cycloalkyl$C_1$-$C_3$-alkyl-, $C_1$-$C_6$ alkoxy$C_1$-$C_3$alkyl-, $C_1$-$C_6$ alkoxy-$C_2$-$C_6$alkoxy-, $C_1$-$C_6$ alkoxy-$C_2$-$C_6$alkoxy-$C_1$-$C_3$alkyl-, $C_1$-$C_6$ halo alkoxy-, $C_1$-$C_6$ halo alkoxy-$C_1$-$C_3$alkyl-, $C_1$-$C_6$alkyl-S(O)$_p$—, $C_1$-$C_6$haloalkyl-S(O)$_p$—, aryl, aryl-S(O)$_p$—, heterocyclyl, heterocyclyl-S(O)$_p$—, aryloxy-, aryl-$C_2$-$C_6$alkyl-, aryl-$C_1$-$C_6$alkoxy-, heterocyclyloxy-, heterocyclyl-$C_1$-$C_3$alkoxy-$C_1$-$C_3$alkyl-, hydroxycarbonyl, hydroxycarbonyl-$C_1$-$C_3$ alkoxy-, $C_1$-$C_3$ alkoxycarbonyl-, $C_1$-$C_3$ alkoxycarbonyl-$C_1$-$C_3$ alkoxy-, $C_1$-$C_3$alkylamino-, $C_1$-$C_3$dialkylamino-, $C_1$-$C_3$ alkylamino-S(O)$_p$—, $C_1$-$C_3$-alkylamino-S(O)$_p$—$C_1$-$C_3$alkyl-, $C_1$-$C_3$ dialkylamino-S(O)$_p$—, $C_1$-$C_3$ dialkylamino-S(O)$_p$—$C_1$-$C_3$alkyl-, $C_1$-$C_3$alkylaminocarbonyl-, $C_1$-$C_3$alkylaminocarbonyl-$C_1$-$C_3$alkyl-, $C_1$-$C_3$dialkylaminocarbonyl-, $C_1$-$C_3$ dialkylaminocarbonyl-$C_1$-$C_3$alkyl-,
$C_1$-$C_3$alkylcarbonylamino-, $C_1$-$C_3$ alkyl-S(O)$_p$-amino-, $C_1$-$C_3$alkyl-S(O)$_p$—$C_1$-$C_3$alkylamino-, $C_1$-$C_3$alkyl-S(O)$_p$-amino$C_1$-$C_3$alkyl, cyano and nitro, wherein said heterocyclyls are five or six membered heterocyclyls containing from one to three heteroatoms each independently selected from the group consisting of oxygen, nitrogen and sulphur, and wherein the aryl or heterocyclyl components may be optionally substituted by one or more substituents selected from the group consisting of halo, $C_1$-$C_3$alkyl, $C_1$-$C_3$haloalkyl, $C_1$-$C_3$ alkoxy, $C_1$-$C_3$ haloalkoxy, $C_1$-$C_6$alkyl-S(O)$_p$—, phenyl, cyano and nitro;
$R^6$ and $R^9$ are independently selected from the group consisting of hydrogen, hydroxyl, halogen, $C_1$-$C_6$alkyl, $C_1$-$C_6$cycloalkyl, $C_1$-$C_6$haloalkyl, $C_2$-$C_6$alkenyl, $C_2$-$C_6$haloalkenyl, $C_2$-$C_6$alkynyl, $C_1$-$C_6$ alkoxy-, $C_2$-$C_6$ alkenyloxy-, $C_3$-$C_6$cycloalkyl$C_1$-$C_3$-alkyl-, $C_1$-$C_6$ alkoxy$C_1$-$C_3$alkyl-, $C_1$-$C_6$ alkoxy-$C_2$-$C_6$alkoxy-, $C_1$-$C_6$ alkoxy-$C_2$-$C_6$alkoxy-$C_1$-$C_3$alkyl-, $C_1$-$C_6$ haloalkoxy-, $C_1$-$C_6$ haloalkoxy-$C_1$-$C_3$alkyl-, $C_1$-$C_6$alkyl-S(O)$_p$—, $C_1$-$C_6$haloalkyl-S(O)$_p$—, aryl, aryl-S(O)$_p$—, heterocyclyl, heterocyclyl-S(O)$_p$—, aryloxy-, aryl-$C_2$-$C_6$alkyl-, aryl-$C_1$-$C_6$alkoxy-, heterocyclyloxy-, heterocyclyl-$C_1$-$C_3$alkoxy-$C_1$-$C_3$alkyl-, hydroxycarbonyl, hydroxycarbonyl-$C_1$-$C_3$alkoxy-, $C_1$-$C_3$ alkoxycarbonyl-, $C_1$-$C_3$alkoxycarbonyl-$C_1$-$C_3$ alkoxy-, $C_1$-$C_3$alkylamino-, $C_1$-$C_3$dialkylamino-, $C_1$-$C_3$alkylamino-S(O)$_p$—, $C_1$-$C_3$ alkylamino-S(O)$_p$—$C_1$-$C_3$alkyl-, $C_1$-$C_3$ dialkylamino-S(O)$_p$—, $C_1$-$C_3$ dialkylamino-S(O)$_p$—$C_1$-$C_3$alkyl-,
$C_1$-$C_3$alkylaminocarbonyl-, $C_1$-$C_3$alkylaminocarbonyl-$C_1$-$C_3$alkyl-, $C_1$-$C_3$dialkylaminocarbonyl-, $C_1$-$C_3$ dialkylaminocarbonyl-$C_1$-$C_3$alkyl-,
$C_1$-$C_3$alkylcarbonylamino-, $C_1$-$C_3$ alkyl-S(O)$_p$-amino-, $C_1$-$C_3$alkyl-S(O)$_p$—$C_1$-$C_3$alkylamino-, $C_1$-$C_3$alkyl-S(O)$_p$— amino$C_1$-$C_3$alkyl-, cyano and nitro, wherein said heterocyclyls are five or six membered heterocyclyls containing from one to three heteroatoms each independently selected from the group consisting of oxygen, nitrogen and sulphur, and wherein the aryl or heterocyclyl components may be optionally substituted by one or more substituents selected from the group consisting of halo, $C_1$-$C_3$alkyl, $C_1$-$C_3$haloalkyl, $C_1$-$C_3$ alkoxy, $C_1$-$C_3$ haloalkoxy, $C_1$-$C_6$alkyl-S(O)$_p$—, phenyl, cyano and nitro;

$R^7$ and $R^8$ are independently selected from the group consisting of hydrogen, halogen, $C_1$-$C_3$ alkyl-, $C_1$-$C_3$ alkoxy-, $C_2$-$C_3$alkenyl-, $C_2$-$C_3$alkynyl-, $C_1$-$C_3$ haloalkyl- and $C_1$-$C_3$haloalkoxy-;

and wherein $R^5$ and $R^9$ can together form a saturated or unsaturated 5- or 6-membered carbocyclic or heterocyclic ring, said heterocyclic ring comprising one or more nitrogen and/or oxygen heteroatoms, the 5- or 6-membered ring being optionally substituted by one or more $R^{12}$; or $R^6$ and $R^9$ can together form a saturated or unsaturated 5- or 6-membered carbocyclic or heterocyclic ring, said heterocyclic ring comprising one or more heteroatoms selected from the group consisting of nitrogen, oxygen and $S(O)_2$, the 5- or 6-membered ring being optionally substituted by one or more $R^{12}$; or $R^6$ and $R^8$ can together form a saturated or unsaturated 5- or 6-membered carbocyclic or heterocyclic ring, said heterocyclic ring comprising one or more nitrogen heteroatoms, the 5- or 6-membered ring being optionally substituted by one or more $R^{13}$; and $R^{11}$ is selected from the group consisting of halo-, $C_1$-$C_3$alkyl, $C_1$-$C_3$ haloalkyl and $C_1$-$C_6$alkoxy;

$R^{12}$ is selected from the group of hydrogen, cyano, halo-, oxy-, $C_1$-$C_3$alkylS(O)$_p$—, $C_1$-$C_3$ alkyl, $C_2$-$C_3$alkenyl, $C_2$-$C_3$alkynyl, $C_1$-$C_3$ alkoxy and $C_1$-$C_3$ haloalkyl;

$R^{13}$ is selected from the group of hydrogen, cyano, halo-, $C_1$-$C_3$alkylS(O)$_p$—, $C_1$-$C_3$ alkyl, $C_2$-$C_3$alkenyl, $C_2$-$C_3$alkynyl, morpholinyl- and $C_1$-$C_3$ haloalkyl; and p=0, 1 or 2.

Alkyl groups having a chain length of from 1 to 6 carbon atoms include, for example, methyl (Me, $CH_3$), ethyl (Et, $C_2H_5$), n-propyl, isopropyl (i-Pr), n-butyl (n-bu), iso-butyl (i-bu), sec-butyl and tert-butyl (t-butyl).

Alkenyl groups having a chain length of from 2 to 6 carbon atoms include, for example, —CH=$CH_2$ (vinyl) and —$CH_2$—CH=$CH_2$ (allyl).

Alkynyl groups having a chain length of from 2 to 6 carbon atoms include, for example, —C≡CH (ethynyl) and —$CH_2$—C≡CH (propargyl).

Cycloalkyl groups include c-propyl (c-Pr), c-butyl (c-Bu), c-pentyl and c-hexyl.

Halogen (halo) encompasses fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Haloalkenyl radicals include alkenyl groups substituted one or more times by halogen, halogen being fluorine, chlorine, bromine or iodine and especially fluorine or chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl. Preferred $C_2$-$C_6$alkenyl radicals substituted once, twice or three times by halogen are those having a chain length of from 2 to 5 carbon atoms.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. Alkylcarbonyl is preferably acetyl or propionyl. Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl, preferably methoxycarbonyl, ethoxycarbonyl or tert-butoxycarbonyl. It should also be appreciated that two alkoxy substituents present on the same carbon atom may be joined to form a spiro group. Thus, the methyl groups present in two methoxy substituents may be joined to form a spiro 1,3 dioxolane substituent, for example. Such a possibility is within the scope of the present invention.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

Alkylthio (alkyl-S—) groups preferably have a chain length of from 1 to 6 carbon atoms. Alkylthio is, for example, methylthio, ethylthio, propylthio, isopropylthio, n-butylthio, isobutylthio, sec-butylthio or tert-butylthio, preferably methylthio or ethylthio.

Alkylsulfinyl (alkyl-SO—) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

Alkylsulfonyl (alkyl-S(O)$_2$—) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Alkylamino (alkyl-NH—) is, for example, methylamino, ethylamino, n-propylamino, isopropylamino or a butylamino isomer. Dialkylamino ((alkyl)$_2$-N—) is, for example, dimethylamino, methylethylamino, diethylamino, n-propylmethylamino, dibutylamino or diisopropylamino. Preference is given to alkylamino groups having a chain length of from 1 to 4 carbon atoms.

Cycloalkylamino- or dicycloalkylamino- is for example cyclohexylamino or dicyclopropylamino.

Alkoxyalkyl groups preferably have from 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkylthioalkyl (alkyl-5-alkyl) groups preferably have from 1 to 6 carbon atoms. Alkylthioalkyl is, for example, methylthiomethyl, methylthioethyl, ethylthiomethyl, ethylthioethyl, n-propylthiomethyl, n-propylthioethyl, isopropylthiomethyl, isopropylthioethyl, butylthiomethyl, butylthioethyl or butylthiobutyl.

Cycloalkyl groups preferably have from 3 to 6 ring carbon atoms and may be substituted by one or more methyl groups; they are preferably unsubstituted, for example cyclopropyl (c-Pr), cyclobutyl (c-Bu), cyclopentyl (c-pentyl) or cyclohexyl (c-hexyl).

Aryl includes benzyl, phenyl, including phenyl as part of a substituent such as phenoxy, benzyl, benzyloxy, benzoyl, phenylthio, phenylalkyl, phenoxyalkyl or tosyl, may be in mono- or poly-substituted form, in which case the substituents may, as desired, be in the ortho-, meta- and/or para-position(s). The term also includes, for example, naphthalenyl.

Heterocyclyl, includes, for example, morpholinyl, tetrahydrofuryl and heteroaryl.

Heteroaryl, including heteroaryl as part of a substituent such as heteroaryloxy, means, for example, a five to ten (preferably five or six) member heteroaryl containing one to three heteroatoms, each independently selected from the group consisting of oxygen, nitrogen and sulphur. The term heteroaryl thus includes, for example, benzofuranyl, benzimidazolyl, indolyl, isobenzofuranyl, furanyl, thiophenyl, thiazolyl, oxazolyl, isoxazolyl, thiazolyl, pyrazolyl, isothiazolyl, pyridyl, pyridazinyl, pyrazinyl, pyrimidinyl, pyridonyl, triazolyl, napthyridinyl and napthyridinonyl. The heteroaryl component may be optionally mono or poly substituted as previously defined.

Preferably, $R^1$ is selected from the group consisting of hydrogen, $C_1$-$C_6$alkyl, $C_2$-$C_6$alkenyl, $C_2$-$C_6$alkynyl, $C_3$-$C_6$cycloalkyl, $C_1$-$C_6$haloalkyl $C_1$-$C_6$alkoxy-$C_1$-$C_3$alkyl and $C_3$-$C_6$cycloalkyl-$C_1$-$C_3$alkyl. In a more preferred embodiment $R^1$ is selected from the group consisting of $C_1$-$C_4$alkyl, cyclopropyl, difluoromethyl, cyclopropylmethyl-, vinyl and propargyl with methyl being particularly preferred.

Preferably $R^2$ is selected from the group consisting of A1a, A1b, A1c, A1d, A1e, A1f, A1g, A1h, A2a, A2b, A3a, A3b and A3b:

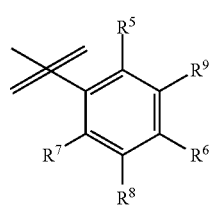

(A1a)

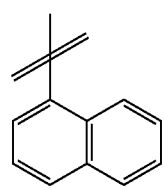

(A1b)

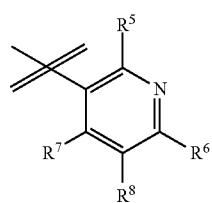

(A1c)

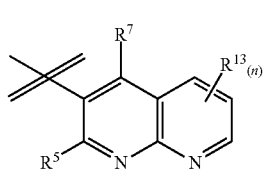

(A1d)

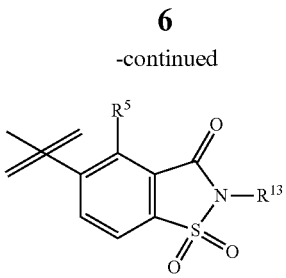

(A1e)

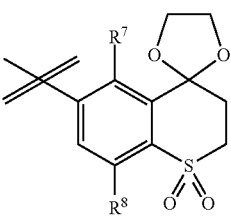

(A1f)

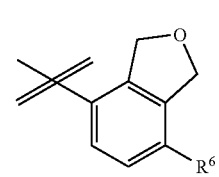

(A1g)

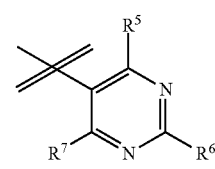

(A1h)

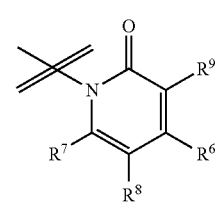

(A2a)

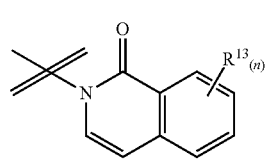

(A2b)

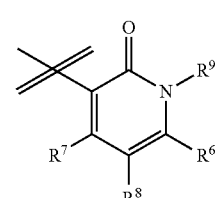

(A3a)

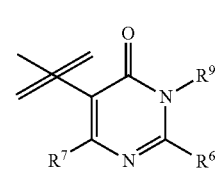

(A3b)

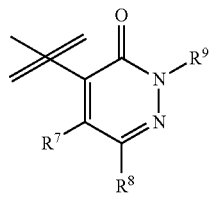

(A3c)

wherein R⁵, R⁶, R⁷, R⁸, R⁹ and R¹³ are as defined previously and n is 0, 1, 2 or 3.

More preferably, $R^2$ is selected from the group consisting of phenyl (e.g. A1a), 3-pyridyl (e.g. A1c), N-pyridonyl (e.g. A2a) and 3-linked [1,8]naphthyridinyl (e.g. A1d). Even more preferably $R^2$ is phenyl (e.g. A1a).

Preferably, $R^3$ is selected from the group consisting of hydrogen, halo, cyano, $C_1$-$C_6$alkyl, $C_2$-$C_6$alkenyl, $C_2$-$C_6$alkynyl, $C_1$-$C_6$haloalkyl and $C_1$-$C_6$alkyl-S(O)$_p$—. More preferably, $R^3$ is selected from the group consisting of hydrogen, halo and $C_1$-$C_6$alkyl, most preferred being hydrogen or methyl.

$R^4$ is preferably hydrogen.

$R^3$ and $R^4$ are both preferably hydrogen.

$R^5$ is preferably selected from the group consisting of hydroxyl, halo, $C_1$-$C_6$alkyl, $C_1$-$C_6$cycloalkyl, $C_1$-$C_6$haloalkyl, $C_1$-$C_6$alkenyl, $C_1$-$C_6$alkynyl, $C_1$-$C_6$ alkoxy, $C_1$-$C_6$ alkoxy$C_1$-$C_3$alkyl, $C_1$-$C_6$ alkoxy-$C_2$-$C_6$alkoxy, $C_1$-$C_6$ alkoxy-$C_2$-$C_6$alkoxy-$C_1$-$C_3$alkyl, $C_1$-$C_6$ haloalkoxy, $C_1$-$C_6$ haloalkoxy-$C_1$-$C_3$alkyl, $C_1$-$C_6$alkyl-S(O)$_p$—, $C_1$-$C_6$haloalkyl-S(O)$_p$—, aryl, aryloxy, heterocyclyl, heterocyclyl-$C_1$-$C_3$alkoxy-$C_1$-$C_3$alkyl, $C_1$-$C_3$alkylamino-, $C_1$-$C_3$dialkylamino-, $C_1$-$C_3$ alkylamino-S(O)$_p$—, $C_1$-$C_3$ alkylamino-S(O)$_p$—$C_1$-$C_3$alkyl-, $C_1$-$C_3$ dialkylamino-S(O)$_p$—, $C_1$-$C_3$ dialkylamino-S(O)$_p$—$C_1$-$C_3$alkyl-, $C_1$-$C_3$alkylaminocarbonyl-, $C_1$-$C_3$dialkylaminocarbonyl-, $C_1$-$C_3$ dialkylaminocarbonyl-$C_1$-$C_3$alkyl-, $C_1$-$C_3$alkylcarbonylamino-, $C_1$-$C_3$ alkyl-S(O)$_p$-amino-, cyano and nitro, wherein said heterocyclyls are five or six membered heterocyclyls containing from one to three heteroatoms each independently selected from the group consisting of oxygen, nitrogen and sulphur, and wherein the aryl or heterocyclyl components may be optionally substituted by one or more substituents selected from the group consisting of halo, $C_1$-$C_3$alkyl, $C_1$-$C_3$haloalkyl, $C_1$-$C_3$ alkoxy, $C_1$-$C_3$ haloalkoxy, cyano and nitro.

The terms "aryl" and "heterocyclyl" are further defined above. However, in the context of $R^5$ phenyl, benzyl, isoxazolinyl, pyrimidinyl, morpholinyl, furyl and thiophenyl are particularly preferred.

More preferably, $R^5$ is selected from the group consisting of chloro, fluoro, methyl, trifluoromethyl, 2-fluoroethyl-, methoxyethoxymethyl-, trifluoromethoxymethyl-, methylS(O)$_p$—, aryl, isoxazolinyl, morpholinyl, methyl-S(O)$_p$-dimethylamino-, cyano and nitro, wherein the aryl or heterocyclyl components may be optionally substituted by one or more substituents selected from the group consisting of chloro, methyl and trifluoromethyl. Most preferably, $R^5$ is selected from the group consisting of methyl, methyl-S(O)$_2$— and trifluoromethyl.

Preferably, $R^6$ is selected from the group consisting of hydrogen, halogen, $C_1$-$C_6$alkyl, $C_1$-$C_6$haloalkyl, $C_1$-$C_6$alkyl-S(O)$_p$—, $C_1$-$C_6$cycloalkyl, $C_2$-$C_6$alkenyl, $C_2$-$C_6$haloalkenyl, $C_2$-$C_6$alkynyl, $C_1$-$C_6$ alkoxy-, $C_1$-$C_6$haloalkoxy, $C_2$-$C_6$alkenyloxy-, $C_3$-$C_6$cycloalkyl$C_1$-$C_3$-alkyl-, $C_1$-$C_6$ alkoxy$C_1$-$C_3$alkyl-, $C_1$-$C_6$ alkoxy-$C_2$-$C_6$alkoxy-, nitro and phenyl wherein the phenyl may be optionally substituted by one or more substituents selected from the group consisting of halo, $C_1$-$C_3$alkyl, $C_1$-$C_3$haloalkyl, $C_1$-$C_3$ alkoxy, $C_1$-$C_3$ haloalkoxy, $C_1$-$C_6$alkyl-S(O)$_p$—, phenyl, cyano and nitro. More preferably, $R^6$ is selected from the group consisting of hydrogen, halogen, $C_1$-$C_6$alkyl, $C_1$-$C_6$haloalkyl, $C_1$-$C_6$alkyl-S(O)$_p$—, $C_2$-$C_6$alkenyl and $C_2$-$C_6$alkynyl.

Preferably, $R^7$ is selected from the group consisting of hydrogen, halogen and $C_1$-$C_3$ alkyl-.

Preferably, $R^8$ is selected from the group consisting of hydrogen, halogen and $C_1$-$C_3$ alkyl-.

Preferably, $R^9$ is selected from the group consisting of hydrogen, halogen, $C_1$-$C_6$alkyl, $C_1$-$C_6$haloalkyl, $C_1$-$C_6$alkyl-S(O)$_p$—, $C_1$-$C_6$cycloalkyl, $C_2$-$C_6$alkenyl, $C_2$-$C_6$haloalkenyl, $C_2$-$C_6$alkynyl, $C_1$-$C_6$ alkoxy-, $C_1$-$C_6$haloalkoxy, $C_2$-$C_6$alkenyloxy-, $C_3$-$C_6$cycloalkyl$C_1$-$C_3$-alkyl-, $C_1$-$C_6$ alkoxy$C_1$-$C_3$alkyl-, $C_1$-$C_6$ alkoxy-$C_2$-$C_6$alkoxy-, nitro and phenyl wherein the phenyl may be optionally substituted by one or more substituents selected from the group consisting of halo, $C_1$-$C_3$alkyl, $C_1$-$C_3$haloalkyl, $C_1$-$C_3$ alkoxy, $C_1$-$C_3$ haloalkoxy, $C_1$-$C_6$alkyl-S(O)$_p$—, phenyl, cyano and nitro. More preferably, $R^9$ is selected from the group consisting of hydrogen, halogen, $C_1$-$C_6$alkyl, $C_1$-$C_6$haloalkyl, $C_1$-$C_6$alkyl-S(O)$_p$—, $C_2$-$C_6$alkenyl and $C_2$-$C_6$alkynyl.

Compounds of Formula I may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

Similarly, where there are disubstituted alkenes, these may be present in E or Z form or as mixtures of both in any proportion.

Furthermore, compounds of Formula I may be in equilibrium with alternative hydroxyl tautomeric forms. It should be appreciated that all tautomeric forms (single tautomer or mixtures thereof), racemic mixtures and single isomers are included within the scope of the present invention.

The present invention also includes agronomically acceptable salts that the compounds of Formula I may form with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

The compounds of Formula (I) according to the invention can be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound according to any one of the previous claims and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The composition of the present may further comprise at least one additional pesticide. For example, the compounds according to the invention can also be used in combination with other herbicides or plant growth regulators. In a preferred embodiment the additional pesticide is a herbicide and/or herbicide safener. Examples of such mixtures are (in which 'I' represents a compound of Formula I). I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bicyclopyrone, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+fluorochloridone, I+fluoroxypyr, I+flurtamone, I+fluthiacet, I+fluthiacet-methyl, I+fomesafen, I+foramsulfuron, I+fosamine, I+glufosinate, I+glufosinate-ammonium, I+glyphosate, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+p entoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+tri-allate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6). The compounds of the present invention may also be combined with herbicidal compounds disclosed in WO06/024820 and/or WO07/096,576.

The mixing partners of the compound of Formula I may also be in the form of esters or salts, as mentioned e.g. in The Pesticide Manual, Fourteenth Edition, British Crop Protection Council, 2006.

The compound of Formula I can also be used in mixtures with other agrochemicals such as fungicides, nematicides or insecticides, examples of which are given in The Pesticide Manual.

The mixing ratio of the compound of Formula I to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula I according to the invention can also be used in combination with one or more safeners. Likewise, mixtures of a compound of Formula I according to the invention with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxy-benzoylsulfamoyl)-benzamide (CAS RN 221668-34-4). Other possibilities include safener compounds disclosed in, for example, EP0365484 e.g N-(2-methoxybenzoyl)-4-[(methylaminocarbonyl)amino]benzenesulfonamide. Particularly preferred are mixtures of a compound of Formula I with cyprosulfamide, isoxadifen-ethyl, cloquintocet-mexyl and/or N-(2-methoxybenzoyl)-4-[(methyl-aminocarbonyl)amino]benzenesulfonamide.

The safeners of the compound of Formula I may also be in the form of esters or salts, as mentioned e.g. in The Pesticide Manual, 14$^{th}$ Edition (BCPC), 2006. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula I to safener is from 100:1 to 1:10, especially from 20:1 to 1:1.

The mixtures can advantageously be used in the above-mentioned formulations (in which case "active ingredient" relates to the respective mixture of compound of Formula I with the safener).

The present invention still further provides a method of selectively controlling weeds at a locus comprising crop plants and weeds, wherein the method comprises application to the locus of a weed controlling amount of a composition according to the present invention. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula I may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf Maize is particularly preferred.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

In a preferred embodiment the crop plant is rendered tolerant to HPPD-inhibitors via genetic engineering. Methods of rending crop plants tolerant to HPPD-inhibitors are known, for example from WO0246387. Thus in an even more preferred embodiment the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria, Chenchrus, Lolium, Festuca, Setaria, Eleusine, Sorghum* or *Avena* species.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled may be both monocotyledonous species, for example *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*, and dicotyledonous species, for example *Abutilon, Amaranthus, Ambrosia, Chenopodium, Chrysanthemum, Conyza, Galium, Ipomoea, Nasturtium, Sida, Sinapis, Solanum, Stellaria, Veronica, Viola* and *Xanthium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

The compounds of the present invention can be prepared using the following methods.

Compounds of formula (1a) may be prepared from compounds of Formula (I) as shown in reaction scheme 1.

Reaction scheme 1

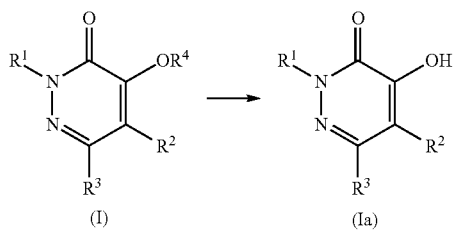

Compounds of formula (Ia), in which $R^4$ is hydrogen, may be prepared from compounds of formula I in which $R^4$ is lower alkyl, for example methyl, by heating with morpholine (Nagashima, Hiromu et al. Heterocycles, 26(1), 1-4; 1987); Compounds of Formula (I) may be prepared from compounds of formula (2) as shown in reaction scheme 2.

Reaction scheme 2

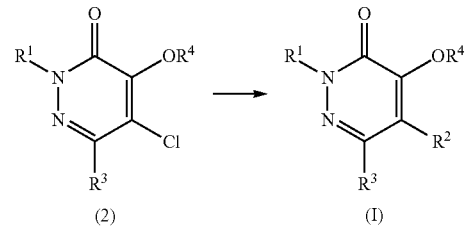

Compounds of Formula (I) in which $R^4$ is lower alkyl, for example methyl, and in which $R^2$ is aryl or heteroaryl, may be prepared from compounds of formula (2) by reaction with a suitable metal or metalloid derivative Y-M (e.g. a boronic acid or ester, a trialkyltin derivative, a zinc derivative or a Grignard reagent) in the presence of a suitable base (e.g. an inorganic base, such as potassium phosphate or caesium fluoride), a metal source (e.g. a palladium source, such as Pd (OAc)2) and optionally a ligand for the metal (e.g. a phosphine ligand) in a suitable solvent (e.g. a single solvent, such as dimethylformamide, or a mixed solvent system such as a mixture of dimethoxyethane and water or toluene and water). The metal catalyst and ligands may also be added as a single, pre-formed complex (e.g. a palladium/phosphine complex, such as bis(triphenylphosphine)palladium dichloride or [1,1'-bis(diphenylphosphino)ferrocene]palladium dichloride dichloromethane adduct). Compounds of formula (2) may be prepared from compounds of formula (3) as shown in reaction scheme 3.

Reaction scheme 3

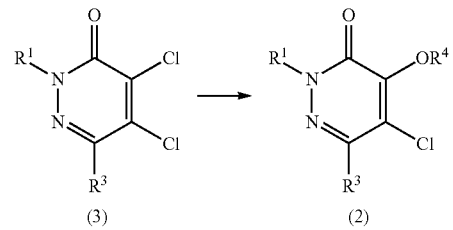

Compounds of formula (2) in which $R^4$ is lower alkyl, for example methyl, may be prepared from compounds of formula (3) by reaction with a suitable metal alkoxide, for example sodium methoxide, in a suitable solvent such as dioxane;

Compounds of formula (3) may be prepared from compounds of formula (4) as shown in reaction scheme 4.

Reaction scheme 4

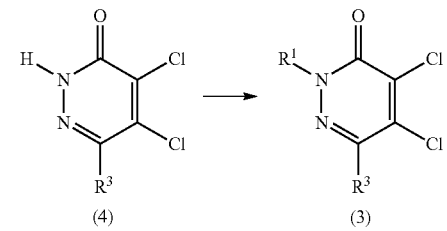

Compounds of formula (3) may be prepared from the compound of formula (4) (4,5-dichloro-1H-pyridazin-6-one—available commercially) by reaction with a suitable alkylating agent $R^1$—X, where X is a leaving group such as halide, for example methyl iodide, in the presence of a suitable base (e.g. an inorganic base, such as potassium carbonate) in a suitable solvent such as N,N-dimethylformamide.

Alternatively, compounds of Formula (1) may be prepared from compounds of formula (5) as shown in reaction scheme 5.

Reaction scheme 5

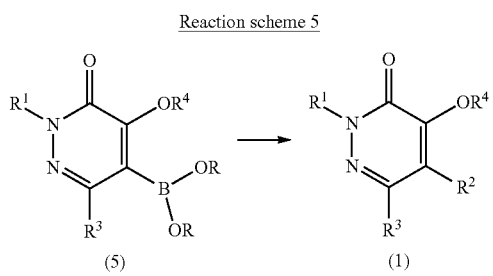

(5)  (1)

Compounds of Formula (1) in which $R^4$ is lower alkyl, for example methyl, and in which $R^2$ is aryl or heteroaryl, may be prepared from compounds of formula (5) by reaction with a suitable alkylating agent $R^2$—X in the presence of a suitable base (e.g. an inorganic base, such as potassium phosphate or caesium fluoride), a metal source (e.g. a palladium source, such as Pd $(OAc)_2$) and optionally a ligand for the metal (e.g. a phosphine ligand) in a suitable solvent (e.g. a single solvent, such as dimethylformamide, or a mixed solvent system such as a mixture of dimethoxyethane and water or toluene and water). The metal catalyst and ligands may also be added as a single, pre-formed complex (e.g. a palladium/phosphine complex, such as bis(triphenylphosphine)palladium dichloride or [1,1'-bis(diphenylphosphino)ferrocene]palladium dichloride dichloromethane adduct). Compounds of formula (5) may be prepared from compounds of formula (6) as shown in reaction scheme 6.

Reaction scheme 6

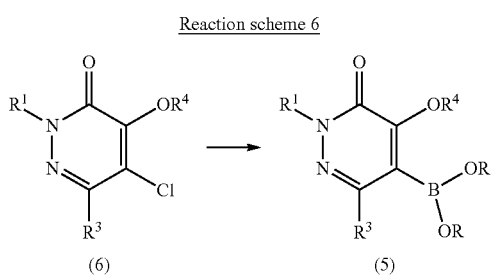

(6)  (5)

Compounds of formula (5) in which $R^4$ is lower alkyl, for example methyl, may be prepared from compounds of formula (6) by reaction with a suitable boronic acid or ester for example bis(pinacolato)diboron in the presence of a suitable base (e.g. an inorganic base, such as potassium phosphate or caesium fluoride), a metal source (e.g. a palladium source, such as $Pd_2(dba)_3$ or $Pd(OAc)_2$) and optionally a ligand for the metal (e.g. a phosphine ligand such as tricyclohexylphosphine) in a suitable solvent (e.g. a single solvent, such as dioxane, or a mixed solvent system such as a mixture of dimethoxyethane and water or toluene and water). The metal catalyst and ligands may also be added as a single, pre-formed complex (e.g. a palladium/phosphine complex, such as bis(triphenylphosphine)palladium dichloride or [1,1'-bis(diphenylphosphino)ferrocene] palladium dichloride dichloromethane adduct). Analogous reactions are known in the art e.g. Tetrahedron, 57(49), 9813-9816; 2001 Alternatively, compounds of formula (1c) in which $R^2$ is a nitrogen-linked heterocycle, for example indole or pyridone, may be prepared from compounds of formula (3) or (4) as shown in reaction scheme 7.

Reaction scheme 7

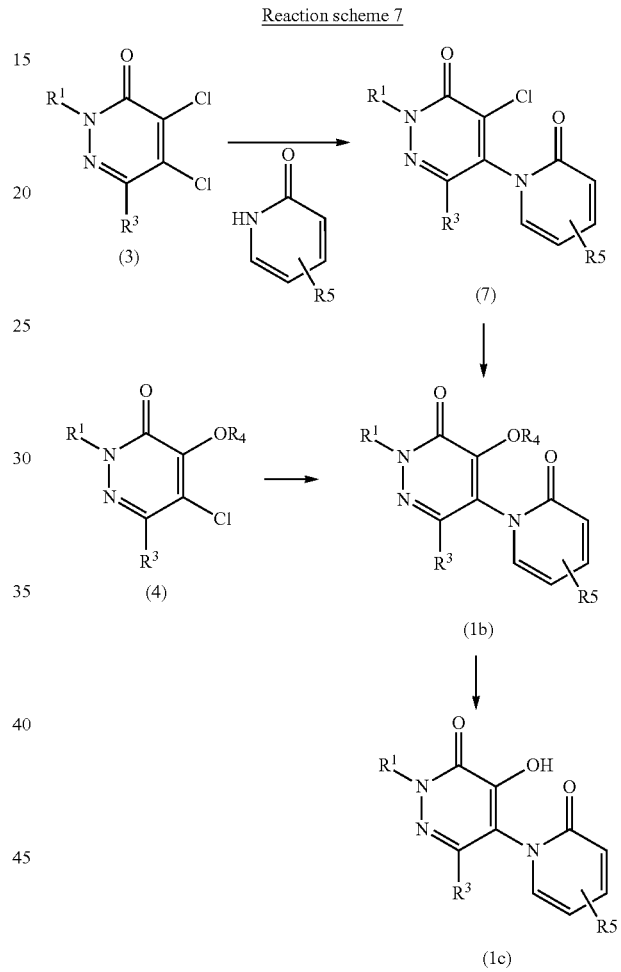

Compounds of formula (7) and (1b) may be prepared from compounds of formula (3) and (4) respectively by reaction with a nitrogen-containing heterocycle such as an indole or pyridone in the presence of a suitable base such in a suitable solvent.

Compounds of formula (1b) in which $R^4$ is lower alkyl, for example methyl, may be prepared from compounds of formula (7) as described in reaction scheme 3, and compounds of formula (1c) may be prepared from compounds of formula (1b) as described in reaction scheme 1. Alternatively compounds of formula (1c) may be prepared directly from compounds of formula (7) by reaction with a suitable metal hydroxide such as potassium hydroxide, in a suitable solvent such as aqueous methanol.

Compounds of Formula (1) may also be prepared from compounds of formula (8) as shown in reaction scheme 8.

Reaction scheme 8

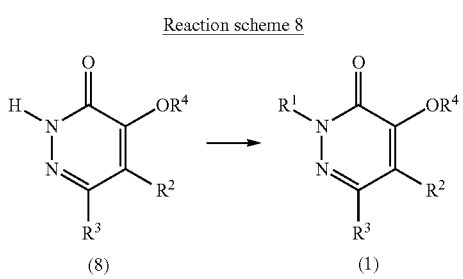

Compounds of Formula (1) in which $R^4$ is lower alkyl, for example methyl, may be prepared from compounds of formula (8) by reaction with a suitable alcohol $R^1OH$, in a suitable solvent such as tetrahydrofuran, in the presence of a suitable additive such as triphenylphosphine and an azodicarboxylate such as diethyl azodicarboxylate (DEAD) or diisopropyl azodicarboxylate (DIAD).

Compounds of formula (8) may be prepared from compounds of formula (1d) as shown in reaction scheme 9.

Reaction scheme 9.

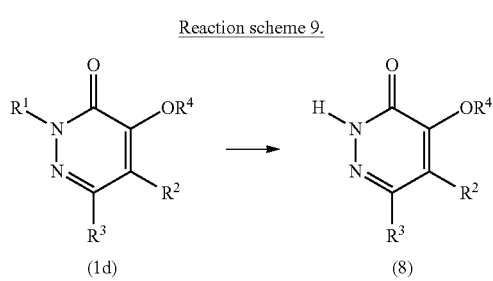

Compounds of formula (8) may be prepared from compounds of formula (1d), in which $R^1$ is a removable protecting group such as p-methoxybenzyl, by reaction with a suitable oxidising agent such as cerium ammonium nitrate in a suitable solvent such as aqueous acetonitrile.

Compounds of formula (1d), in which $R^1$ is a removable protecting group such as p-methoxybenzyl, may be prepared from commercially available compound (4) (4,5-dichloro-1H-pyridazin-6-one) in a method analogous to that in schemes 2-4.

Compounds of formula (3) may also be prepared from compounds (9) as shown in reaction scheme 10

Reaction scheme 10

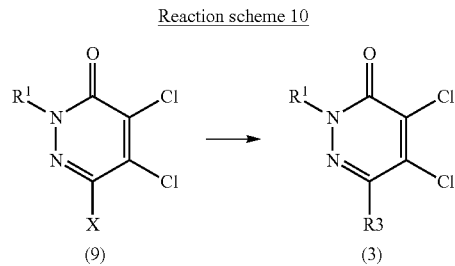

Compounds of formula (3), in which $R^3$ is for example alkyl, alkenyl or alkynyl, may also be prepared from compounds (9), in which X is a suitable leaving group such as bromide, by reaction with a suitable metal or metalloid derivative Y-M (e.g. a boronic acid or ester, a trialkyltin derivative, a zinc derivative or a Grignard reagent) in the presence of a suitable base (e.g. an inorganic base, such as potassium phosphate or caesium fluoride), a metal source (e.g. a palladium source, such as Pd (OAc)$_2$) and optionally a ligand for the metal (e.g. a phosphine ligand) in a suitable solvent (e.g. a single solvent, such as dioxane, or a mixed solvent system such as a mixture of dimethoxyethane and water or toluene and water). The metal catalyst and ligands may also be added as a single, pre-formed complex (e.g. a palladium/phosphine complex, such as bis(triphenylphosphine)palladium dichloride or [1,1'-bis(diphenylphosphino)ferrocene]palladium dichloride dichloromethane adduct). Compounds of formula (9) can be prepared via known methods.

Compounds of formula (3) may also be prepared as shown in reaction scheme 11.

Reaction scheme 11

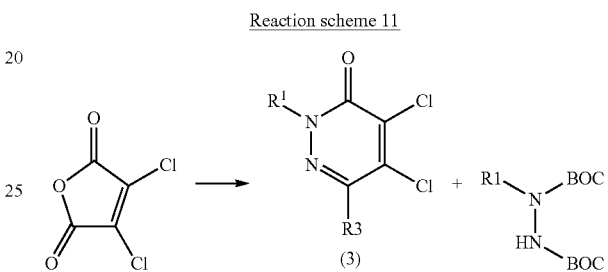

Compounds of formula (3) in which $R^3$ is hydrogen may be prepared by reaction of 3,4-dichloro-2,5-furandione or 3,4-dibromo-2,5-furandione with a suitably protected hydrazine in a suitable solvent such as aqueous hydrochloric acid.

Analogous reactions are known e.g. Angewandte Chemie (1965), 77(7), 282-90; Synthetic Communications (2006), 36(18), 2719-2726

Compounds of Formula (I) in which $R^2$ is a C-linked pyridone may be prepared from compounds of formula 2 as shown in scheme 12.

Reaction Scheme 12

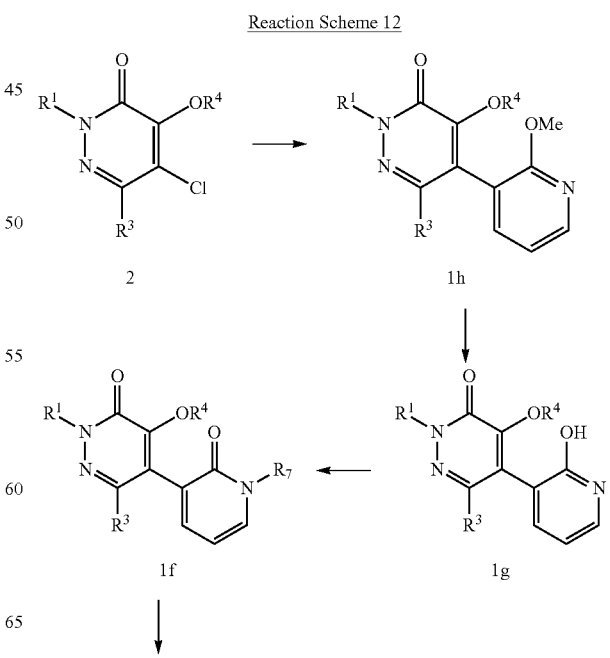

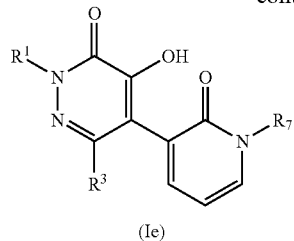

(Ie)

Compounds of formula 1h in which $R^4$ is lower alkyl, for example methyl, may be prepared from compounds of formula 2 by reaction with a suitable metal or metalloid derivative of 2-methoxypyridine (e.g. a boronic acid or ester, a trialkyltin derivative, a zinc derivative or a Grignard reagent) in the presence of a suitable base (e.g. an inorganic base, such as potassium phosphate or caesium fluoride), a metal source (e.g. a palladium source, such as Pd $(OAc)_2$) and optionally a ligand for the metal (e.g. a phosphine ligand) in a suitable solvent (e.g. a single solvent, such as dimethylformamide, or a mixed solvent system such as a mixture of dimethoxyethane and water or toluene and water). The metal catalyst and ligands may also be added as a single, pre-formed complex (e.g. a palladium/phosphine complex, such as bis(triphenylphosphine)palladium dichloride or [1,1'-bis(diphenylphosphino)ferrocene]palladium dichloride dichloromethane adduct). Compound 1g may be prepared from compound 1h by reaction with a dilute aqueous acid such as hydrochloric acid, optionally with heating or reaction in the microwave, analogous to known methods such as disclosed in Bioorganic & Medicinal Chemistry Letters, 18(9), 2967-2971; 2008.

Compounds of formula 1f may be prepared from compounds of formula 1g by reaction with a suitable aryl iodide, in the presence of copper iodide, a suitable base such as potassium triphosphate, in the presence of a suitable catalyst such as tetrabutylammonium chloride in a suitable solvent such as N,N-dimethylformamide, optionally with heating or reaction in the microwave. Analogous reactions are known e.g. Tet. Lett. 45 (2004) 4257-4260.

Compounds of formula 1e may be prepared from compounds of Formula (1g) as described in Reaction Scheme 1.

Reaction scheme 13

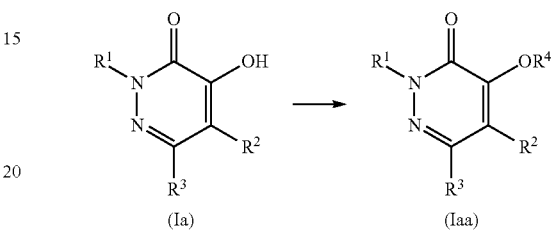

(Ia)                (Iaa)

Compounds of formula (1aa) in which $R^4$ is for example is alkylcarbonyl, arylcarbonyl, alkoxycarbonyl, alkoxysulphonyl or arylsulphonyl may be prepared from compounds of general formula (1a) in which $R^4$ is hydrogen by reaction with a suitable halide such as acetyl chloride, methyl chloroformate, ethyl thiochloroformate or p-toluenesulphonyl chloride, in the presence of a suitable base such as triethylamine or pyridine, in the presence of a suitable solvent such as dichloromethane or toluene.

Reaction Scheme 14

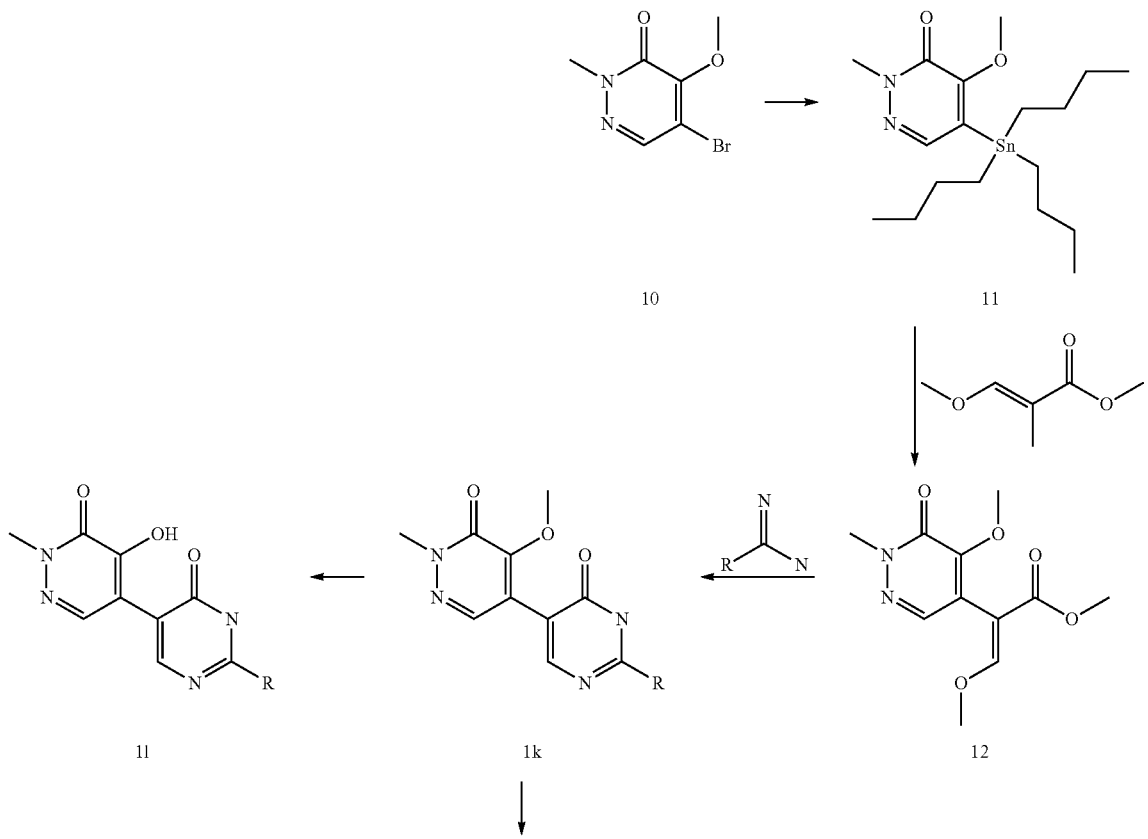

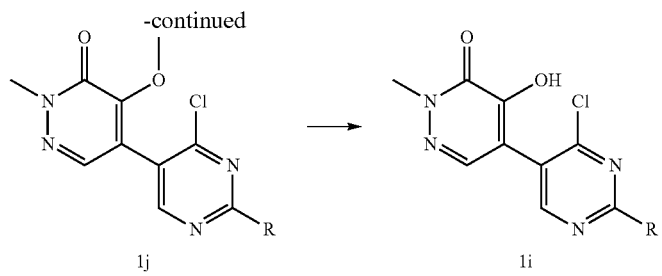

Compounds of Formula (1i) in which $R^2$ is a substituted pyrimidine, or Formula (1l), in which $R^2$ is a substituted pyrimidinone may be prepared according to reaction scheme 14. Compounds of Formula (11) may be prepared from compounds of Formula 10 by reaction of the corresponding Grignard reagent with tributyltin chloride in the presence of a suitable solvent such as tetrahydrofuran, the reaction being cooled during addition of the reagents. Analogous reactions are known e.g J. Org. Chem., 2011, 76, 6670-6677 (Grignard formation), WO2010/59943 (p. 32) and Journal of Organometallic Chemistry, 1973, (63), 133-138.

Compounds of Formula (12) may be prepared from compounds of Formula (11) by reaction with methyl (Z)-2-iodo-3-methoxy-prop-2-enoate in the presence of a suitable base (e.g. an inorganic base, such as potassium phosphate or caesium fluoride), a metal source (e.g. a palladium source, such as palladium (0) tetrakis(triphenylphosphine)) and a catalyst such as copper iodide, optionally with heating, according to analogous processes e.g. Angew. Chem. Int. Ed., 2004, 43, 1132-1136.

Compounds of general Formula (1k) may be prepared from compounds of general Formula (12) by reaction with a suitable amidine in the presence of a suitable metal alkoxide, for example sodium methoxide, in a suitable solvent such as methanol, the reaction mixture being heated.

Compounds of general Formula (1j) may be prepared from compounds of general Formula (1k) by reaction with a suitable chlorinating reagent, such as phosphorus oxychloride, optionally in the presence of a suitable solvent, according to procedures known e.g. Journal of Organic Chemistry, 76(10), 4149-4153; 2011.

Compounds of general Formulas (1i) and (1l) may be prepared from compounds of general Formulas (1j) and (1k) respectively as described in Reaction Scheme 1

EXAMPLES

Examples of the synthesis of specific compounds of the present invention are provided below.

Example 1

5-[2-chloro-3-(4,5-dihydroisoxazol-3-yl)-4-methyl-sulfonyl-phenyl]-4-hydroxy-2-propyl-pyridazin-3-one A mixture of 5-[2-chloro-3-(4,5-dihydroisoxazol-3-yl)-4-methylsulfonyl-phenyl]-4-methoxy-2-propyl-pyridazin-3-one (692 mg, 1.62 mmol) in morpholine (1.42 ml) was heated to 100° C. for 1 h. The reaction mixture was cooled then dichloromethane (20 ml) and 2M hydrochloric acid (20 ml) were added and the mixture stirred for 30 mins. The dichloromethane layer was separated then the aqueous layer extracted twice with dichloromethane. The combined organic extracts were passed through a phase separation cartridge then concentrated in vacuo. The crude product was dissolved in ethyl acetate then precipitated with hexane, concentrated in vacuo and triturated with acetonitrile to give the product as an off-white solid (224.6 mg).

5-[2-chloro-3-(4,5-dihydroisoxazol-3-yl)-4-methyl-sulfonyl-phenyl]-4-methoxy-2-propyl-pyridazin-3-one A mixture of 5-chloro-4-methoxy-2-propyl-pyridazin-3-one (811 mg, 4 mmol), potassium acetate (589 mg, 6 mmol), bis(pinicolato)diboron (1.52 g, 6 mmol), tris(dibenzylideneacetone)dipalladium(0) (148 mg, 0.16 mmol) and tricyclohexylphosphine (180 mg, 0.64 mmol) in degassed dioxane (12 ml) was heated at 150° C. for 15 minutes under microwave irradiation. The mixture was allowed to cool to room temperature then filtered through Celite, eluting with ethyl acetate. The filtrate was evaporated under reduced pressure then used directly in the next step.

The crude boronate ester was dissolved in degassed dimethoxyethane (12 ml); to the mixture were added 3-(3-bromo-2-chloro-6-methylsulfonyl-phenyl)-4,5-dihydroisoxazole (2.71 g, 8 mmol), caesium fluoride (2.43 g, 16 mmol) and [1,1'-bis(diphenylphosphino)ferrocene]palladium(II) dichloride dichloromethane adduct (260 mg, 0.32 mmol). The resulting mixture was heated at 150° C. for 20 minutes under microwave irradiation then allowed to cool to room temperature and filtered through Celite, eluting with ethyl acetate. The filtrate was concentrated under reduced pressure then purified by chromatography on silica eluting with 0-100% ethyl acetate in isohexane to give the product as a brown oil (692 mg).

8.06 (1H, d, J 8.1), 7.59 (1H, s), 7.56 (1H, d, J 8.1), 4.63 (3H, t, J 10.2), 4.19 (3H, s), 4.12 (2H, dd, J 7.3, 7.3), 3.47 (3H, t, J 10.2), 3.28 (3H, s), 1.90 (2H, m), 1.02 (3H, t, J 7.2)

5-chloro-4-methoxy-2-propyl-pyridazin-3-one

To a stirred solution of 4,5-dichloro-2-propyl-pyridazin-3-one (7.31 g, 35.3 mmol) in dioxane (150 ml) was added a solution of sodium methoxide in methanol (25% wt in methanol, 8.6 ml, 38.8 mmol) dropwise and the mixture stirred at room temperature for 60 mins. Water (150 ml) was added and the mixture extracted with diethyl ether (3×100 ml). The combined organics were dried, filtered and concentrated in vacuo.

The crude product was purified by chromatography on silica eluting with ethyl acetate/hexanes to give the desired product as a colourless oil (5.44 g).

4,5-dichloro-2-propyl-pyridazin-3-one

To a stirred solution of 4,5-dichloro-1H-pyridazin-6-one (8.25 g, 50 mmol) in N,N-dimethylformamide (25 ml) at room temperature was added potassium carbonate (1.2 g, 60 mmol) and 1-iodopropane (5.85 ml, 60 mmol). The mixture was stirred at 70 C for 2 hrs then water (75 ml) was added and the mixture extracted with dichloromethane (3×100 ml). The combined organic extracts were dried, filtered and concentrated in vacuo then partitioned between brine (200 ml) and diethylether (200 ml). The organic layer was dried, filtered and concentrated in vacuo to give a brown oil. The crude product was purified by chromatography on silica eluting with ethyl acetate/hexanes to give the desired product as a colourless oil (7.31 g).

7.78 (1H, s), 4.20-4.11 (2H, m), 1.90-1.74 (2H, m), 0.96 (3H, t, J 7.2)

Example 2

4-hydroxy-2-methyl-5-[2-methylsulfonyl-4-(trifluoromethyl)phenyl]pyridazin-3-one A mixture of 4-methoxy-2-methyl-5-[2-methylsulfonyl-4-(trifluoromethyl)phenyl]pyridazin-3-one (48 mg, 0.132 mmol) in morpholine (2 ml) was heated to 100° C. for 3 hours. The reaction was then allowed to cool to room temperature and evaporated under reduced pressure. The resulting residue was dissolved in ethyl acetate and washed with 2M hydrochloric acid. The organic layer was then dried over sodium sulphate and evaporated. The resulting solid was triturated with dichloromethane/hexane to give the desired product as a pale pink solid (25 mg).

4-methoxy-2-methyl-5-[2-methylsulfonyl-4-(trifluoromethyl)phenyl]pyridazin-3-one To a solution of 4-methoxy-2-methyl-5-[2-methylsulfanyl-4-(trifluoromethyl)phenyl]pyridazin-3-one (90 mg. 0.27 mmol) in acetic acid (4 ml) was added hydrogen peroxide (50% wt in water, 56 mg, 0.82 mmol) at room temperature. The reaction mixture was slowly heated to 55° C. and maintained at that temperature overnight. The reaction mixture was diluted with dichloromethane and quenched with sat. aq. sodium hydrogen carbonate and solid sodium hydrogen carbonate slowly until the pH was ~6-7. The organic layer was separated and the aqueous phase extracted with dichloromethane. The combined organics were dried over sodium sulphate and evaporated to give the desired product (78 mg) as a pale yellow oil. This was used without further purification.

$\delta_H$ (CDCl$_3$) 8.46 (1H, d), 7.98 (1H, dd), 7.60 (1H, s), 7.46 (1H, d), 4.14 (3H, s), 3.85 (3H, s), 3.02 (3H, s)

4-methoxy-2-methyl-5-[2-methylsulfanyl-4-(trifluoromethyl)phenyl]pyridazin-3-one A mixture of 5-chloro-4-methoxy-2-methyl-pyridazin-3-one (100 mg, 0.573 mmol), potassium acetate (84 mg, 0.86 mmol), bis(pinacolato)diboron (218 mg, 0.86 mmol), tris(dibenzylideneacetone)dipalladium(0) (4%, 21 mg, 0.023 mmol) and tricyclohexylphosphine (16%, 26 mg, 0.092 mmol) in degassed dioxane (2.5 ml) was heated at 150° C. for 15 min under microwave irradiation. The mixture was filtered through celite, washing with ethyl acetate and the filtrate evaporated under reduced pressure. The residue was dissolved in degassed 1,2-dimethoxyethane (2.5 ml) and 1-bromo-2-methylsulfanyl-4-(trifluoromethyl)benzene (233 mg, 0.86 mmol), caesium fluoride (348 mg, 2.29 mmol) and [1,1'-bis(diphenylphosphino)-ferrocene]palladium(II)chloride, dichloromethane complex (8%, 38 mg, 0.046 mmol) were then added. The resulting mixture was heated at 160° C. for 15 min under microwave irradiation. The reaction mixture was filtered through celite, washing with ethyl acetate. The filtrate was evaporated under reduced pressure and the residue purified by chromatography on silica, eluting with 0-40% ethyl acetate in hexanes, to give the desired product (190 mg, containing some residual pinacol impurity) as a red oil. This was used without further purification.

$\delta_H$ (CDCl$_3$) 7.52 (1H, s), 7.50 (1H, br s), 7.47 (1H, br d), 7.26 (1H, br d), 4.05 (3H, s), 3.84 (3H, s), 2.49 (3H, s)

5-chloro-4-methoxy-2-methyl-pyridazin-3-one

To a stirred solution of 4,5-dichloro-2-methyl-pyridazin-3-one (19.7 g, 110 mmol) in 1,4-dioxane (550 ml) was added sodium methoxide (28.5 g, 132 mmol, 30.2 ml) dropwise and the resulting mixture stirred at room temperature for 1 hr. The reaction was quenched with water (~500 ml) then extracted with diethyl ether (500 ml then 250 ml). The combined organics were dried, filtered and concentrated in vacuo to give 15.83 g of a white solid.

$\delta_H$ (CDCl$_3$) 7.68 (1H, s), 4.28 (3H, s), 3.75 (3H, s)

4,5-dichloro-2-methyl-pyridazin-3-one

To a stirred solution of 4,5-dichloro-1H-pyridazin-6-one (25.0 g, 152 mmol) in N,N-dimethylformamide (152 ml) was added potassium carbonate (25.4 g, 182 mmol) and iodomethane (25.8 g, 182 mmol, 11.3 ml). The resulting mixture was stirred at room temperature overnight. The reaction mixture was then poured onto ice-water (300 ml) and the mixture stirred for 15 mins. The resulting precipitate was collected by filtration, then dissolved in dichloromethane and passed through a phase separation cartridge. The organics were concentrated in vacuo to give 19.7 g of a pale brown solid.

1H NMR (400 MHz, Chloroform) d ppm 3.83 (s, 3H) 7.77 (s, 1H)

Example 3

4-hydroxy-2-methyl-5-[3-(m-tolyl)-2-oxo-4-(trifluoromethyl)-1-pyridyl]pyridazin-3-one A mixture of 4-chloro-2-methyl-5-[3-(m-tolyl)-2-oxo-4-(trifluoromethyl)-1-pyridyl]pyridazin-3-one (74 mg, 0.19 mmol) in aqueous potassium hydroxide (0.5M, 3 ml, 0.606 mmol) and methanol (2.5 ml) was heated at 55° C. for 90 minutes. Morpholine (1 ml) was added and reaction heated at 90° C. for 2 hours. The reaction mixture was concentrated under reduced pressure. 2M hydrochloric acid was then carefully added to the residue with rapid stirring for 5-10 min. The resulting cream precipitate was filtered, washed with 2M hydrochloric acid and water and then dried in a vacuum oven at 55° C. overnight to give the desired product (37 mg).

4-chloro-2-methyl-5-[3-(m-tolyl)-2-oxo-4-(trifluoromethyl)-1-pyridyl]pyridazin-3-one A mixture of 3-(m-tolyl)-4-(trifluoromethyl)-1H-pyridin-2-one (68 mg, 0.269 mmol), 4,5-dichloro-2-methyl-pyridazin-3-one (58 mg, 0.323 mmol) and potassium carbonate (112 mg, 0.807 mmol) in N,N-dimethylformamide (1 ml) was heated in the microwave at 150° C. for 25 min. The reaction mixture was then poured into 2M hydrochloric acid and extracted with ethyl acetate. The organic extracts were combined, dried over sodium sulphate and evaporated under reduced pressure. The crude mixture was purified by chromatography on silica, eluting with ethyl acetate in hexanes to give the desired product as a yellow oil (74 mg).

$\delta_H$ (CDCl$_3$) 7.84 (1H, s), 7.34-7.22 (3H, m), 7.11 (2H, m), 6.63 (1H, d), 3.88 (3H, s), 2.38 (3H, s)

3-(m-tolyl)-4-(trifluoromethyl)-1H-pyridin-2-one

A mixture of 2-chloro-3-(m-tolyl)-4-(trifluoromethyl) pyridine (96 mg, 0.353 mmol) and sodium hydroxide in dimethylsulphoxide (0.6 ml) and water (0.6 ml) was heated at 150° C. under microwave irradiation for 60 minutes. The liquid mixture was separated from the glassy residue and acidified to pH 1 with 2M hydrochloric acid. The resulting white precipitate was filtered, washed with a few drops of water and dried in a vacuum oven at 55° C. overnight to give the product as a white solid (68 mg).

$\delta_H$ (CD3OD) 7.62 (1H, d), 7.34-7.30 (1H, m), 7.25-7.23 (1H, m), 7.06 (1H, s), 7.02 (1H, d), 6.66 (1H, d), 2.40 (3H, s)

2-chloro-3-(m-tolyl)-4-(trifluoromethyl)pyridine

A mixture of 2-chloro-3-iodo-4-methyl-pyridine (200 mg, 0.652 mmol), m-tolylboronic acid (132 mg, 0.976 mmol), tetrakis(triphenylphosphine) palladium(0) (8%, 60 mg, 0.052 mmol) and potassium carbonate (136 mg, 0.976 mmol) in 1,2-dimethoxyethane (2.8 ml) was heated at 150° C. for 30 min under microwave irradiation. The reaction mixture was poured into brine and extracted with ethyl acetate. The organic extracts were dried over sodium sulphate and evaporated. The crude mixture was purified by chromatography on silica, eluting with ethyl acetate in hexanes, to give the product as a colourless oil (96 mg).

2-chloro-3-iodo-4-methyl-pyridine n-Butyllithium (1.6M in hexanes, 13.3 ml, 21.3 mmol) was added dropwise to a solution of diisopropylamine (33 ml, 23.3 mmol) in tetrahydrofuran (7 ml) at −70° C. (internal temp) and the resulting mixture was stirred for 30 min. 2-Chloro-4-trifluoromethyl-pyridine (2.5 ml, 3.52 g, 19.4 mmol) was then added dropwise over 20 minutes and the mixture stirred for 2 hours at −70° C. This was then cannulated rapidly into a solution of iodine (5.2 g, 20.4 mmol) in tetrahydrofuran (3 ml) held at 0° C. The resulting mixture was stirred for 10 min, quenched with aqueous sodium metabisulfite and extracted with ethyl acetate. The organic layer was collected, washed with brine, dried over magnesium sulphate and evaporated. The crude mixture was purified by chromatography on silica, eluting with ethyl acetate in hexane, to give the desired compound (4.87 g, ~82%) as a pale yellow solid contaminated with traces of starting material.

$\delta_H$ (CDCl$_3$) 8.50 (1H, d), 7.44 (1H, d)

Example 4

2-cyclopentyl-5-[3-(4,5-dihydroisoxazol-3-yl)-2-methyl-4-methylsulfonyl-phenyl]-4-methoxy-pyridazin-3-one To a stirred solution of 4-[3-(4,5-dihydroisoxazol-3-yl)-2-methyl-4-methylsulfonyl-phenyl]-5-methoxy-1H-pyridazin-6-one (126 mg, 0.35 mmol), triphenylphosphine (184 mg, 0.70 mmol) and cyclopentanol (0.06 ml, 0.70 mmol) in dry THF (3.5 ml) under a nitrogen atmosphere was added diisopropyl azodicarboxylate (0.14 ml, 0.7 mmol) dropwise. The resulting mixture was stirred at room temperature for 3 hours then concentrated in vacuo. The crude product was purified by column chromatography on silica, eluting with isohexane/ethyl acetate, to give 2-cyclopentyl-5-[3-(4,5-dihydroisoxazol-3-yl)-2-methyl-4-methylsulfonyl-phenyl]-4-methoxy-pyridazin-3-one (94 mg).

8.06 (1H, d, J 8.1), 7.56 (1H, s), 7.43 (1H, d, J 8.1), 5.50-5.41 (1H, m), 4.61 (2H, t, J 9.9), 4.10 (3H, s), 3.41 (2H, br s), 3.22 (3H, s), 2.17-2.02 (2H, m), 2.04 (3H, s), 2.00-1.86 (4H, m), 1.74-1.67 (2H, m)

4-[3-(4,5-dihydroisoxazol-3-yl)-2-methyl-4-methyl-sulfonyl-phenyl]-5-methoxy-1H-pyridazin-6-one To a stirred solution of 5-[3-(4,5-dihydroisoxazol-3-yl)-2-methyl-4-methylsulfonyl-phenyl]-2-[(4-hydroxyphenyl) methyl]-4-methoxy-pyridazin-3-one (281 mg, 0.58 mmol) in acetonitrile (5 ml) and water (1 ml) at room temperature was added ceric ammonium nitrate and the mixture was stirred at room temperature. The reaction was monitored by LCMS.

After 90 minutes, brine (25 ml) and ethyl acetate (25 ml) were added. The layers were separated and the aqueous layer extracted with ethyl acetate a further two times. The combined organics were washed with sat aqueous sodium bicarbonate (25 ml), then dried and concentrated in vacuo. The crude product was triturated with hexane (~20 ml) and filtered to give 126 mg pale yellow solid.

8.08 (1H, d, J 8.1), 7.56 (1H, s), 7.44 (1H, d, J 8.1), 4.61 (2H, t, J 10.2), 4.19 (3H, s), 3.43 (2H, br s), 3.22 (3H, s), 2.19 (3H, s)

5-[3-(4,5-dihydroisoxazol-3-yl)-2-methyl-4-methyl-sulfonyl-phenyl]-2-[(4-hydroxyphenyl)methyl]-4-methoxy-pyridazin-3-one A mixture of 5-chloro-4-methoxy-2-[(4-methoxyphenyl) methyl]pyridazin-3-one (281 mg, 1 mmol), palladium acetate (18 mg, 0.08 mmol), 3-[2-methyl-6-methylsulfonyl-3-(4,4,5,5-tetramethyl-1,3,2-dioxaborolan-2-yl)phenyl]-4,5-dihydroisoxazole (548 mg, 1.5 mmol), aqueous tripotassium phosphate (0.4 ml. 2 mmol) and SPhos (66 mg, 0.16 mmol) in degassed toluene was heated at 150° C. for 30 minutes under microwave irradiation. The mixture was allowed to cool to room temperature then filtered through Celite, eluting with ethyl acetate. The filtrate was evaporated under reduced pressure, and then purified by column chromatography to give the desired product as a pink oil (281 mg).

8.00 (1H, d), 7.49 (1H, s), 7.41 (2H, d), 7.35 (1H, d), 6.86 (2H, d), 5.36-5.14 (2H, br d), 4.54 (2H, t), 4.07 (3H, s), 3.77 (3H, s), 3.34 (2H, br s), 3.18 (3H, s), 2.11 (3H, s)

3-[2-methyl-6-methylsulfonyl-3-(4,4,5,5-tetramethyl-1,3, 2-dioxaborolan-2-yl)phenyl]-4,5-dihydroisoxazole is prepared as described in example 7 below.

5-chloro-4-methoxy-2-[(4-methoxyphenyl)methyl] pyridazin-3-one

To a stirred solution of 4,5-dichloro-2-[(4-methoxyphenyl)methyl]pyridazin-3-one (5.70 g, 20 mmol) in dry dioxane (50 ml) was added the sodium methoxide solution (30 wt % soln. in methanol (~5.4 M), 4.07 ml, 22 mmol) at room temperature. The resulting mixture was stirred at room temperature, monitoring by LCMS, and then poured into water (50 ml)/dichloromethane (50 ml). The organic layer was separated and the aqueous layer extracted with dichloromethane (2×50 ml). The combined organics were dried over magnesium sulphate and evaporated. The crude product was purified by column chromatography on silica, eluting with ethyl acetate/hexane, to give the desired product 5-chloro-4-methoxy-2-[(4-methoxyphenyl)methyl] pyridazin-3-one as a white solid (4.53 g) together with the isomeric compound, 4-chloro-5-methoxy-2-[(4-methoxyphenyl)methyl]pyridazin-3-one (650 mg).

Nmr Data:
5-chloro-4-methoxy-2-[(4-methoxyphenyl)methyl] pyridazin-3-one: 7.70 (1H, s), 7.39 (2H, d), 6.84 (2H, d), 5.20 (2H, s), 4.24 (3H, s), 3.79 (3H, s)
4-chloro-5-methoxy-2-[(4-methoxyphenyl)methyl] pyridazin-3-one: 7.80 (1H, s), 7.40 (2H, d), 6.86 (2H, d), 5.29 (2H, s), 4.02 (3H, s), 3.79 (3H, s)
4,5-dichloro-2-[(4-methoxyphenyl)methyl]pyridazin-3-one is prepared from 4,5-dichloro-1H-pyridazin-6-one by a procedure analogous to that described in example 1 above.

Example 5

5-[6-fluoro-2-(trifluoromethyl)-1,8-naphthyridin-3-yl]-4-hydroxy-2-methyl-pyridazin-3-one 5-[6-fluoro-2-(trifluoromethyl)-1,8-naphthyridin-3-yl]-4-methoxy-2-methyl-pyridazin-3-one (70 mg, 0.1976 mmol) was dissolved in acetonitrile (5 ml) and sodium iodide (50 mg, 0.33 mmol) was added in a 20 ml microwave tube. Chloro(trimethyl)silane (0.043 ml, 0.34 mmol) was added and the yellow reaction mixture immediately went purple. The mixture was stirred in a microwave vial at 100° C. for 30 minutes. LCMS showed only partial conversion to the desired product. More chloro(trimethyl)silane and sodium iodide were added and the reaction re-microwaved at 100° C. for 30 mins. LCMS showed an increase in the desired product but suggested the starting material was still the major component (~60%). The mixture was poured into water, basified with 2M sodium hydroxide and extracted into dichloromethane. The organic extracts were passed through a phase separation cartridge and evaporated to yield the un-reacted starting material. The basic aqueous layer was acidified with 2M hydrochloric acid and extracted with dichloromethane. The organic extracts were passed through a second phase separation cartridge and evaporated to yield the desired product, 5-[6-fluoro-2-(trifluoromethyl)-1,8-naphthyridin-3-yl]-4-hydroxy-2-methyl-pyridazin-3-one (21 mg, 0.062 mmol) as a pink solid.

1H NMR (400 MHz, Chloroform) δ ppm d 1H 9.18, s 1H 8.35, dd 1H 7.98, s 1H 7.69, s 3H 3.90

5-[6-fluoro-2-(trifluoromethyl)-1,8-naphthyridin-3-yl]-4-methoxy-2-methyl-pyridazin-3-one

[6-fluoro-2-(trifluoromethyl)-1,8-naphthyridin-3-yl]-trimethyl-stannane (200 mg, 0.528 mmol), 5-chloro-4-methoxy-2-methyl-pyridazin-3-one (105 mg, 0.60144 mmol), 1,4-bis(diphenylphosphinobutane)palladium dichloride (33 mg), copper(II) oxide (45 mg, 0.566 mmol) and N,N-dimethylformamide (5 ml, 64.4 mmol) were stirred in a microwave vial at 140° C. for 30 minutes. LCMS showed good conversion to the desired product with a minor amount of the 'homo-coupled' by-product as well and several other small impurities. The reaction mixture was filtered through a very small silica plug. The filtrate was partitioned between ether and water. The organic extracts were separated, washed, dried over anhydrous magnesium sulphate and evaporated. The crude product was dissolved in dichloromethane and purified by column chromatography, eluting with ethyl acetate/iso-hexane) to give 5-[6-fluoro-2-(trifluoromethyl)-1,8-naphthyridin-3-yl]-4-methoxy-2-methyl-pyridazin-3-one (75 mg, 0.2117 mmol) as a yellow solid.

1H NMR (400 MHz, Chloroform) δ ppm d 1H 9.20, s 1H 8.20, dd 1H 7.92, s 1H 7.61, s 3H 4.14, s 3H 3.88

5-chloro-4-methoxy-2-methyl-pyridazin-3-one is prepared from 4,5-dichloro-1H-pyridazin-6-one as described in example 2.

[6-fluoro-2-(trifluoromethyl)-1,8-naphthyridin-3-yl]-trimethyl-stannane

A mixture of 6-fluoro-3-iodo-2-(trifluoromethyl)-1,8-naphthyridine (400 mg, 1.17 mmol), hexamethyl ditin (1.15 g, 3.40 mmol) and bis(triphenylphosphine)palladium(II)dichloride (100 mg, 0.141 mmol) catalyst, in degassed 1,4-dioxane (6 mL, 70.3 mmol) was heated at 110° C. for 60 minutes under microwave irradiation. LCMS showed excellent conversion to the desired product. The reaction mixture was adsorbed on silica and purified by column chromatography, eluting with ethyl acetate/isohexane, to give [6-fluoro-2-(trifluoromethyl)-1,8-naphthyridin-3-yl]-trimethyl-stannane as a pale orange solid (300 mg, 0.7918 mmol).

1H NMR (400 MHz, Chloroform) δ ppm d 1H 9.10, s 1H 8.48, dd 1H 7.85, s 9H 0.47

6-fluoro-3-iodo-2-(trifluoromethyl)-1,8-naphthyridine can be prepared from 6-fluoro-2-(trifluoromethyl)-1,8-naphthyridin-3-amine by known procedures e.g. in *J. Org. Chem.* 1977, 42 (14), 2426-2431.

Example 6

4-[3-(4,5-dihydroisoxazol-3-yl)-2-methyl-4-methylsulfonyl-phenyl]-1,3-dimethyl-4H-pyridazine-5,6-dione 4-[3-(4,5-dihydroisoxazol-3-yl)-2-methyl-4-methylsulfonyl-phenyl]-1,3-dimethyl-4H-pyridazine-5,6-dione is prepared from 4,5-dichloro-2,6-dimethyl-pyridazin-3-one by a reaction sequence analogous to that in Example 1.

4,5-dichloro-2,6-dimethyl-pyridazin-3-one

To a 20 ml microwave vial was added 6-bromo-4,5-dichloro-2-methyl-pyridazin-3-one (1.00 g, 3.88 mmol), [1,1'-bis(diphenylphosphino)ferrocene]palladium(II) dichloride dichloromethane adduct (0.032 g, 0.039 mmol), caesium carbonate (2.02 g, 6.20 mmol), trimethylboroxine (0.787 g, 6.20 mmol, 0.876 mL) and 1,4-dioxane (9 mL) and heated in the microwave at 100° C. for 1 hour then for a further 30 minutes at 150 C.

The reaction mixture was filtered through celite, silica added and reduced under vacuum. The residue was purified by chromatography on silica, eluting with 0-30% ethyl acetate/hexane to give a white solid containing a 9:1 ratio of the desired product, 4,5-dichloro-2,6-dimethyl-pyridazin-3-one, together with a byproduct, 5-chloro-2,4,6-trimethyl-pyridazin-3-one (502 mg in total). This mixture was used directly in the next step to form 5-chloro-4-methoxy-2,6-dimethyl-pyridazin-3-one, as the by-product does not react.

1H NMR (CDCl$_3$):
4,5-dichloro-2,6-dimethyl-pyridazin-3-one δ 3.79 (s, 3H), 2.44 (s, 3H) 5-chloro-2,4,6-trimethyl-pyridazin-3-one δ 3.73 (s, 3H), 2.38 (s, 3H), 2.29 (s, 3H)

Example 7

2-cyclopropyl-5-[3-(4,5-dihydroisoxazol-3-yl)-2-methyl-4-methylsulfonyl-phenyl]-4-hydroxy-pyridazin-3-one

A solution of 2-cyclopropyl-5-[3-(4,5-dihydroisoxazol-3-yl)-2-methyl-4-methylsulfonyl-phenyl]-4-methoxy-pyridazin-3-one (0.203 g, 0.5032 mmol) in morpholine (0.4384 g, 5.032 mmol, 0.440 ml) was heated at 100° C. for 1 hour.

The reaction mixture was allowed to cool to room temperature then diluted with dichloromethane (5 ml) and 2M hydrochloric acid (5 ml). The mixture was then stirred for 30 mins.

The organic layer was separated and the aqueous layer extracted with dichloromethane (2×5 ml). The combined organics were dried and concentrated in vacuo to give a pink solid.

The crude solid was triturated with acetonitrile (3×2 ml portions) and collected by filtration to give 2-cyclopropyl-5-[3-(4,5-dihydroisoxazol-3-yl)-2-methyl-4-methylsulfonyl-phenyl]-4-hydroxy-pyridazin-3-one as a white solid (0.0883 g).

1H NMR (400 MHz, Chloroform) δ ppm 1.05-1.12 (m, 2H) 1.22-1.29 (m, 2H) 2.23 (s, 3H) 3.21 (s, 3H) 3.39 (br. s., 2H) 4.19 (dt, J=7.65, 3.69 Hz, 1H) 4.60 (t, J=10.07 Hz, 2H) 7.49 (d, J=8.19 Hz, 1H) 7.60 (s, 1H) 8.08 (d, J=8.19 Hz, 1H)

2-cyclopropyl-5-[3-(4,5-dihydroisoxazol-3-yl)-2-methyl-4-methylsulfonyl-phenyl]-4-methoxy-pyridazin-3-one

A mixture of 5-chloro-2-cyclopropyl-4-methoxy-pyridazin-3-one (0.20 g, 1 mmol), 3-[2-methyl-6-methylsulfonyl-3-(4,4,5,5-tetramethyl-1,3,2-dioxaborolan-2-yl)phenyl]-4,5-dihydroisoxazole (0.438 g, 1.2 mmol), palladium (II) acetate (0.018 g, 0.08 mmol), tripotassium phosphate (1.026 g, 2 mmol, 0.4 ml, 5 mol/l) and SPhos (0.0670 g, 0.16 mmol) in toluene (3.46 g, 37.4 mmol, 4.0 ml) was heated at 150° C. for 30 minutes under microwave irradiation.

The reaction mixture was filtered through celite, eluting with ethyl acetate. The filtrate was concentrated in vacuo to give the crude product. The crude product was dryloaded onto silica and purified by chromatography to give 2-cyclopropyl-5-[3-(4,5-dihydroisoxazol-3-yl)-2-methyl-4-methylsulfonyl-phenyl]-4-methoxy-pyridazin-3-one as a colourless oil (0.203 g, 0.503 mmol).

1H NMR (400 MHz, Chloroform) δ ppm 1.03-1.11 (m, 2H) 1.19 (br. s., 2H) 2.18 (s, 3H) 3.22 (s, 3H) 3.40 (br. s., 2H) 4.14 (s, 4H) 4.60 (t, J=10.07 Hz, 3H) 7.41 (d, J=8.19 Hz, 1H) 7.48 (s, 1H) 8.06 (d, J=8.19 Hz, 1H)

3-[2-methyl-6-methylsulfonyl-3-(4,4,5,5-tetramethyl-1,3,2-dioxaborolan-2-yl)phenyl]-4,5-dihydroisoxazole

A mixture of 3-(3-bromo-2-methyl-6-methylsulfonyl-phenyl)-4,5-dihydroisoxazole (A, 3.182 g, 10 mmol), bis(pinacolato)diboron (3.8476 g, 15 mmol), tris(dibenzylideneacetone)dipalladium(0) (0.092 g, 0.1 mmol), S-Phos (0.168 g, 0.4 mmol) and potassium acetate (1.487 g, 15 mmol) in 1,4-dioxane (15.51 g, 176 mmol, 15 ml) was heated at 150 C for 30 mins under microwave irradiation. The crude mixture was filtered through a pad of celite eluting with ethyl acetate. The crude product was dry loaded onto silica and purified by chromatography to give 3-[2-methyl-6-methylsulfonyl-3-(4,4,5,5-tetramethyl-1,3,2-dioxaborolan-2-yl)phenyl]-4,5-dihydroisoxazole as a pale yellow solid. (2.06 g, 5.64 mmol)

1H NMR (400 MHz, Chloroform) δ ppm 1.37 (s, 13H) 2.52 (s, 3H) 3.16 (s, 4H) 3.33 (br. s., 2H) 4.57 (t, J=10.00 Hz, 2H) 7.94 (d, J=8.06 Hz, 1H) 7.99 (d, J=7.92 Hz, 1H)

3-(3-bromo-2-chloro-6-methylsulfonyl-phenyl)-4,5-dihydroisoxazole can be prepared as reported for example in DE 19820722.

5-chloro-2-cyclopropyl-4-methoxy-pyridazin-3-one

To a stirred solution of 4,5-dichloro-2-cyclopropyl-pyridazin-3-one (A, 0.599 g, 2.9214 mmol, 100 mass %) in 1,4-dioxane (100 mL, 100 mass %) was added sodium methoxide (0.69443 g, 3.2135 mmol, 0.735 mL, 25 mass %) dropwise and the resulting mixture stirred at room temperature for 1 hour. The reaction mixture was concentrated in vacuo to give a crude brown oil then dry loaded onto silica and purified by chromatography to give 5-chloro-2-cyclopropyl-4-methoxy-pyridazin-3-one as a white solid (0.498 g).

1H NMR (400 MHz, Chloroform) δ ppm 0.96-1.14 (m, 4H) 3.95-4.07 (m, 1H) 4.28 (s, 3H) 7.64 (s, 1H)

4,5-dichloro-2-cyclopropyl-pyridazin-3-one

A mixture of tert-butyl N-(tert-butoxycarbonylamino)-N-cyclopropyl-carbamate (0.68 g, 2.5 mmol) and mucochloric acid (0.43 g, 2.5 mmol) in hydrochloric acid (4 mol/l) in water (25 mmol, 6.3 ml) was heated at reflux for 6 hours. The reaction mixture was allowed to cool to room temperature then extracted with dichloromethane (3×10 ml). The combined organic extracts were dried and concentrated in vacuo. The crude product was purified by chromatography to give 4,5-dichloro-2-cyclopropyl-pyridazin-3-one as a white solid (0.353 g).

1H NMR (400 MHz, Chloroform) δ ppm 1.02-1.17 (m, 4H) 4.09-4.16 (m, 1H) 7.72 (s, 1H)

Tert-butyl N-(tert-butoxycarbonylamino)-N-cyclopropyl-carbamate

To a stirred suspension of magnesium (1.34 g, 55 mmol) and catalytic iodine in tetrahydrofuran (5 ml) was added 5 ml of a 45 ml solution of cyclopropyl bromide (4.0 ml) in tetrahydrofuran (50 ml). The mixture was heated to initiate Grignard formation then the remaining solution of cyclopropyl bromide was added dropwise over 30 mins with heating (70 C). The Grignard solution was heated at reflux for a further 30 minutes then cooled to 0° C.

To a stirred solution of di-tert-butyl azodicarboxylate in THF (50 ml) at −78° C. was added the solution of cyclopropylmagnesium bromide dropwise via cannula. The resulting solution was stirred at −78° C. for 30 mins then quenched with acetic acid. The mixture was allowed to warm to room temperature then water (150 ml) was added and the mixture extracted three times with diethyl ether. The combined organic extracts were dried, filtered and concentrated in vacuo. The crude product was purified by column chromatography on silica, eluting with ethyl acetate/hexane, to give the product as a white solid (6.68 g).

1H NMR (400 MHz, Chloroform) δ ppm 0.7 (4H, br s), 1.5 (18H, s), 2.9-3.0 (1H, br m), 6.1 and 6.4 (1H, br s)

Example 8

[2-methyl-5-[2-methylsulfonyl-4-(trifluoromethyl)phenyl]-3-oxo-pyridazin-4-yl]acetate To a suspension of 4-hydroxy-2-methyl-5-[2-methylsulfonyl-4-(trifluoromethyl)phenyl]pyridazin-3-one (0.1 g, 0.29 mmol) in dry dichloromethane (1 ml) at room temperature was added pyridine (0.03 g, 0.03 ml, 0.37 mmol) and 4-(dimethylamino)pyridine (0.35 mg, 0.0029 mmol). The mixture was stirred for 2 min and acetyl chloride (0.027 g, 0.025 ml, 0.345 mmol) was added dropwise. The resulting suspension was stirred at room temperature for 2 hours, then diluted with dichloromethane and washed successively with 2M hydrochloric acid and saturated aqueous sodium hydrogen carbonate. The organic layer was collected, passed through a phase-separation cartridge and the filtrate evaporated.

The crude residue was purified by flash chromatography (10-55% ethyl acetate in hexanes, 13 min, then 3 min at 55%, 4 g silica GOLD) to give [2-methyl-5-[2-methylsulfonyl-4-(trifluoromethyl)phenyl]-3-oxo-pyridazin-4-yl]acetate (0.095 g, 0.2434 mmol, 84.78% yield) as a white solid.

4-hydroxy-2-methyl-5-[2-methylsulfonyl-4-(trifluoromethyl)phenyl]pyridazin-3-one was prepared as described in Example 2.

Example 9

Methyl [2-methyl-5-[2-methylsulfonyl-4-(trifluoromethyl)phenyl]-3-oxo-pyridazin-4-yl]carbonate To a suspension of 4-hydroxy-2-methyl-5-[2-methylsulfonyl-4-(trifluoromethyl)phenyl]pyridazin-3-one (0.1 g, 0.29 mmol) in dry toluene (1.99 g, 2.3 ml, 21.5 mmol) at room temperature was added triethylamine (0.032 g, 0.044 ml, 0.31 mmol), followed by methyl chloroformate (0.03 g, 0.024 ml, 0.31 mmol). The resulting mixture was stirred overnight.

Water was added and the mixture extracted with ethyl acetate. The organic extracts were passed through a phase-separation cartridge and the filtrate concentrated under reduced pressure. The residue was purified by flash chromatography (0-50% Ethyl acetate in hexanes, 12 min, then 3 minutes at 50%, 4 g silica) to give methyl [2-methyl-5-[2-methylsulfonyl-4-(trifluoromethyl)phenyl]-3-oxo-pyridazin-4-yl]carbonate (0.113 g, 0.2781 mmol, 96.87% yield) as a white solid.

4-hydroxy-2-methyl-5-[2-methylsulfonyl-4-(trifluoromethyl)phenyl]pyridazin-3-one was prepared as described in Example 2.

Example 10

[2-methyl-5-[2-methylsulfonyl-4-(trifluoromethyl)phenyl]-3-oxo-pyridazin-4-yl]ethylsulfanylformate To a suspension of 4-hydroxy-2-methyl-5-[2-methylsulphonyl-4-(trifluoromethyl)phenyl]pyridazin-3-one (0.1 g, 0.29 mmol) in dry tetrahydrofuran (4.6 g, 5.17 ml, 63.7 mmol) at room temperature was added triethylamine (0.059 g, 0.08 ml, 0.57 mmol) followed by ethyl chlorothioformate (0.047 g, 0.039 ml, 0.36 mmol). The resulting suspension was stirred at room temperature for 90 minutes and then diluted with ethyl acetate and washed with brine. The organic phase was collected and passed through a phase-separation cartridge. The filtrate was evaporated and the residue was purified by flash chromatography (0-40% ethyl acetate in hexanes, 13 min, then 3 min at 40%, 4 g silica) to give [2-methyl-5-[2-methylsulfonyl-4-(trifluoromethyl)phenyl]-3-oxo-pyridazin-4-yl]ethylsulfanylformate (0.126 g, 0.289 mmol, 100% yield) as a white solid.

4-hydroxy-2-methyl-5-[2-methylsulfonyl-4-(trifluoromethyl)phenyl]pyridazin-3-one was prepared as described in Example 2.

Example 11

[2-methyl-5-[2-methylsulfonyl-4-(trifluoromethyl)phenyl]-3-oxo-pyridazin-4-yl]propane-1-sulfonate To a suspension of 4-hydroxy-2-methyl-5-[2-methylsulfonyl-4-(trifluoromethyl)phenyl]pyridazin-3-one (0.1 g, 0.29 mmol) in dichloromethane (1.14 g, 0.86 ml, 13.4 mmol) at room temperature was added a solution of potassium carbonate (0.06 g, 0.43 mmol) in water (0.86 g, 0.86 ml, 47.81 mmol) followed by a solution of 1-propanesulphonyl chloride (0.063 g, 0.05 ml, 0.43 mmol) in dichloromethane (0.2 ml). Benzyltrimethylammonium chloride (0.0027 g, 0.0025 ml, 0.014 mmol) was then added and the biphasic mixture stirred vigorously at room temperature overnight.

The reaction mixture was diluted with water/dichloromethane and the organic phase separated. The aqueous layer was extracted with dichloromethane. The combined organic extracts were washed with aqueous 2M hydrochloric acid and brine and then passed through a phase-separation cartridge. The filtrate was evaporated and the residue purified by flash chromatography (0-50% ethyl acetate in hexanes, 13 min, 4 g silica) to afford [2-methyl-5-[2-methylsulfonyl-4-(trifluoromethyl)phenyl]-3-oxo-pyridazin-4-yl]propane-1-sulfonate (0.1 g, 0.22 mmol, 76.7% yield) as a white solid.

4-hydroxy-2-methyl-5-[2-methylsulfonyl-4-(trifluoromethyl)phenyl]pyridazin-3-one was prepared as described in Example 2.

Example 12

[2-methyl-5-[2-methylsulfonyl-4-(trifluoromethyl)phenyl]-3-oxo-pyridazin-4-yl]propane-1-sulfonate To a suspension of 4-hydroxy-2-methyl-5-[2-methylsulfonyl-4-(trifluoromethyl)phenyl]pyridazin-3-one (0.1 g, 0.2871 mmol) and para-toluene sulphonyl chloride (0.061 g, 0.32 mmol) in dry acetonitrile (4.51 g, 5.7 ml, 110 mmol) at room temperature was added potassium carbonate (0.071 g, 0.52 mmol). The resulting suspension was stirred at room temperature overnight.

The reaction mixture was diluted with water and extracted with ethyl acetate. The organic extracts were passed through a phase-separation cartridge and the filtrate evaporated. The resulting solid was dissolved in minimum amount of dichloromethane and hexane was added dropwise with rapid stirring until precipitation. The precipitate was collected by filtration and dried under suction to afford [2-methyl-5-[2-methylsulfonyl-4-(trifluoromethyl)phenyl]-3-oxo-pyridazin-4-yl]4-methylbenzenesulfonate (0.10 g, 0.2 mmol, 70.0% yield) as a white solid.

4-hydroxy-2-methyl-5-[2-methylsulfonyl-4-(trifluoromethyl)phenyl]pyridazin-3-one was prepared as described in Example 2.

Example 13

4-hydroxy-2-methyl-5-[4-morpholino-2-(trifluoromethyl)pyrimidin-5-yl]pyridazin-3-one 5-[4-chloro-2-(trifluoromethyl)pyrimidin-5-yl]-4-methoxy-2-methyl-pyridazin-3-one (240.0 mg, 0.22 mmol) was dissolved in morpholine (2.5 ml, 28.6 mmol). The reaction was stirred at 100° C. for 45 minutes. The reaction mixture was carefully added to 30.0 ml water and stirred for 10 minutes. The aqueous layer was extracted with dichloromethane (2×20 m). The aqueous layer was then acidified with aqueous hydrochloric acid (2.0M) and then washed with dichloromethane, which was collected using a phase-separation cartridge. The solvent was concentrated in vacuo and the crude was triturated with 5.0 ml acetonitrile then sonicated and the resulting solid (40.0 mg) was collected by filtration. TLC showed some impurity so it was triturated once more using 5.0 ml methanol and the resulting precipitate was isolated to yield 4-hydroxy-2-methyl-5-[4-morpholino-2-(trifluoromethyl)pyrimidin-5-yl]pyridazin-3-one (25.0 mg, 0.07 mmol, 31.2% yield) as a white solid.

5-[4-chloro-2-(trifluoromethyl)pyrimidin-5-yl]-4-methoxy-2-methyl-pyridazin-3-one 4-methoxy-2-methyl-5-[6-oxo-2-(trifluoromethyl)-1H-pyrimidin-5-yl]pyridazin-3-one 515.0 mg, 1.7 mmol) was dissolved in phosphorus (V) oxychloride (5.0 ml, 53 mmol). The mixture stirred at 85° C. for 90 minutes. The reaction was then stopped, and let to cool to room temperature and was then concentrated in vacuo. The crude product was dropped into ice cold water and the aqueous layer extracted with dichloromethane. The organic layers were combined, dried over sodium sulphate, filtrate and concentrated in vacuo, then was purified using a 24 g silica cartridge eluting with iso-hexane:ethyl acetate (100:0→60:40 over 12 minutes then keeping the gradient for 6 minutes). The fractions containing product were concentrated in vacuo to yield 5-[4-chloro-2-(trifluoromethyl)pyrimidin-5-yl]-4-methoxy-2-methyl-pyridazin-3-one (240.0 mg, 0.22 mmol, 13.18% yield) as a translucent oil.

$^1$H NMR (400 MHz, Chloroform) δ ppm=3.86 (3H, s) 4.29 (3H, s) 7.63 (1H, s) 8.76 (1H, s)

4-methoxy-2-methyl-5-[6-oxo-2-(trifluoromethyl)-1H-pyrimidin-5-yl]pyridazin-3-one 2,2,2-Trifluoroacetamidine (450 mg, 11.8 mmol) was suspended in methanol (3.0 ml). Then methyl (E)-3-methoxy-2-(5-methoxy-1-methyl-6-oxo-pyridazin-4-yl)prop-2-enoate (1.00 g, 3.93 mmol) was added, followed by sodium methoxide (1.35 ml, 5.90 mmol). The mixture was heated to 65° C. for 2 hours.

More 2,2,2-trifluoroacetamidine (450.0 mg, 11.8 mmol) and sodium methoxide (1.35 ml, 5.90 mmol) were added and the mixture stirred for another 2 hours. The reaction was stopped and let to cool to room temperature. 2M aqueous hydrochloric acid was added and the mixture was concentrated in vacuo.

The crude product was purified by chromatography on silica, eluting with iso-hexane:ethyl acetate then with dichloromethane:methanol. The fractions containing product were combined and concentrated in vacuo to yield 4-methoxy-2-methyl-5-[6-oxo-2-(trifluoromethyl)-1H-pyrimidin-5-yl]pyridazin-3-one (520.0 mg, 1.72 mmol, 43.7% yield) as a pale yellow solid.

$^1$H NMR (400 MHz, d$_3$-Methanol) δ ppm=3.80 (3H, s) 4.01 (3H, s) 7.94 (1H, s) 8.13 (1H, s)

Methyl (E)-3-methoxy-2-(5-methoxy-1-methyl-6-oxo-pyridazin-4-yl)prop-2-enoate 4-methoxy-2-methyl-5-tributylstannyl-pyridazin-3-one (2.9 g, 6.8 mmol) and methyl (Z)-2-iodo-3-methoxy-prop-2-enoate (1.5 g, 6.2 mmol) were dissolved in N,N-dimethylformamide (15.0 ml, 193 mmol). Caesium fluoride (1.9 g, 2.0 equiv., 12 mmol) was added and the mixture degassed with nitrogen. Copper iodide (0.12 g, 0.62 mmol) and palladium (0) tetrakis(triphenylphosphine) (0.36 g, 0.31 mmol) were then added and the mixture degassed another time with nitrogen before being put in a 55° C. pre-heated heating block for 2 hours.

Water (50 ml) and dichloromethane (50 ml) were added and the reaction shaken vigorously. 50.0 ml Saturated aqueous sodium hydrogen carbonate was added and the mixture shaken again. The dichloromethane layer was collected and concentrated in vacuo. The crude product was dry-loaded onto a 120 g silica cartridge eluting with dichloromethane:ethyl acetate (100:0→40:60 over 20 minutes, then keeping the gradient for another 10 minutes). The fractions containing product were combined and concentrated in vacuo to yield a 1.12 g brown oil that solidified upon standing. The crude product was further purified by column chromatography on silica, eluting with iso-hexane:ethyl acetate (60:40→30:70 over 8 minutes then keeping the gradient for 5 minutes then going to 100% ethyl acetate). The fractions containing product were combined and concentrated in vacuo to yield the product as a pale yellow solid (882.0 mg, 56% yield).

$^1$H NMR (400 MHz, Chloroform, (12wq161h2)) δ ppm=3.74 (3H, s) 3.77 (3H, s) 3.90 (3H, s) 4.11 (3H, s) 7.52 (1H, s) 7.56 (1H, s)

4-methoxy-2-methyl-5-tributylstannyl-pyridazin-3-one

To a stirred solution of 5-bromo-4-methoxy-2-methyl-pyridazin-3-one (5.00 g, 22.8 mmol) in tetrahydrofuran (40.6 g, 560 mmol, 45.7 ml) at −40 C was added 2-mesitylmagnesium bromide (1.0 mol) in tetrahydrofuran (46 g, 45.7 mmol, 46 ml, 1.0 mol/L) dropwise via a dropping funnel (maintaining the internal temperature below −30 C at all times) and the mixture stirred at −40 C for 30 minutes. Tri-n-butyltin chloride (23.2 g, 68.5 mmol, 19.3 ml) was then added dropwise as a solution in tetrahydrofuran (20 ml) and the mixture allowed to warm to 0 C over ~1 hr.

The reaction mixture was then quenched with saturated aqueous ammonium chloride solution (100 ml) and extracted with ethyl acetate (3×100 mL). The combined organic extracts were dried, filtered and concentrated in vacuo to give the crude product.

The crude product was dry loaded onto silica and purified by chromatography to give 4-methoxy-2-methyl-5-tributylstannyl-pyridazin-3-one as a reddish oil (5.21 g, 12.1 mmol, 53.2% yield)

$^1$H NMR (400 MHz, Chloroform) δ ppm 7.56 (1H, s) 4.14 (3H, s) 3.78 (3H, s) 1.44-1.62 (6H, m) 1.27-1.38 (6H, m) 1.00-1.21 (6H, m) 0.89 (9H, t, J=7.3 Hz)

5-bromo-4-methoxy-2-methyl-pyridazin-3-one may be prepared by a route analogous to that in Reaction Scheme 3.

Example 14

3-cyclohexyl-2-(3-fluorophenyl)-5-(5-hydroxy-1-methyl-6-oxo-pyridazin-4-yl)pyrimidin-4-one 3-cyclohexyl-2-(3-fluorophenyl)-5-(5-methoxy-1-methyl-6-oxo-pyridazin-4-yl)pyrimidin-4-one (51.0 mg, 0.118 mmol) was dissolved in morpholine (2.0 ml, 23 mmol. The reaction was stirred at 95° C. for 2 hours. LC indicated no reaction, so temperature was increased to 105° C. and the reaction stirred for a further 2 hours. This time, reaction had gone to completion so it the mixture was allowed to cool to room temperature. Aqueous hydrochloric acid was then added carefully to the reaction mixture until the mixture was acidic. The aqueous layer was washed with dichloromethane and the organic layers were combined and passed through a phase separation cartridge. The solvent was concentrated in vacuo and the crude triturated with 3.0 ml acetonitrile, sonicating the solution for about 1 minute.

The solid was collected by filtration to yield the product as a pale pink solid (25.0 mg, 53.4% yield).

3-cyclohexyl-2-(3-fluorophenyl)-5-(5-methoxy-1-methyl-6-oxo-pyridazin-4-yl)pyrimidin-4-one Ethyl 3-fluorobenzenecarboximidate hydrochloride (135.0 mg, 0.6629 mmol) was suspended in methanol (3.0 ml). Then cyclohexanamine (0.066 g, 0.6629 mmol) was added and the mixture stirred for 2 hours at for 18 hours. The reaction was heated gradually to reflux and stirred for another 2 hours. More cyclohexylamine (0.066 g, 0.6629 mmol) was added and the mixture stirred at reflux for 2 hours. The reaction was stopped and concentrated in vacuo to yield an oil.

The crude product was re-dissolved in methanol (3.0 ml), then sodium methoxide (0.12 g, 0.57 mmol) was added and the mixture stirred for 5 minutes before methyl (E)-3-methoxy-2-(5-methoxy-1-methyl-6-oxo-pyridazin-4-yl)prop-2-enoate (145.0 mg, 0.57 mmol) was then added and the mixture stirred at 65° C. for 3 hours.

The reaction was cooled and the solvent was concentrated in vacuo, then the crude product was taken up in diethyl ether. The organic layer was washed with saturated sodium hydrogen carbonate, and the aqueous washed with diethyl ether. The organic phases were combined, dried over sodium sulphate, filtered and concentrated in vacuo, then was purified by chromatography on silica, eluting with iso-hexane:ethyl acetate to give the product (95 mg) as a pale yellow gum. This was further purified by preparative HPLC and concentrated in vacuo to give the product as a translucent oil (51.0 mg, 21.8% yield).

$^1$H NMR (400 MHz, Chloroform) δ ppm=0.93-1.11 (2H, m) 1.14-1.30 (1H, m) 1.57 (1H, d, J=12.9 Hz) 1.72 (2H, d, J=11.3 Hz) 1.81 (2H, d, J=13.4 Hz) 2.63-2.79 (2H, m) 3.81 (3H, s) 3.87-3.97 (1H, m) 4.21 (3H, s) 7.21-7.26 (1H, m) 7.27-7.30 (1H, m) 7.52 (1H, td, J=7.9, 5.6 Hz) 7.88 (1H, s) 8.07 (1H, s)

Methyl (E)-3-methoxy-2-(5-methoxy-1-methyl-6-oxo-pyridazin-4-yl)prop-2-enoate was prepared as described in Example 13 above.

Example 15

4-hydroxy-2-methyl-5-[2-methylsulfonyl-4-(trifluoromethyl)phenyl]-6-propoxy-pyridazin-3-one 4-hydroxy-2-methyl-5-[2-methylsulfonyl-4-(trifluoromethyl)phenyl]-6-propoxy-pyridazin-3-one can be prepared from 4-methoxy-2-methyl-5-[2-methylsulfonyl-4-(trifluoromethyl)phenyl]-6-propoxy-pyridazin-3-one was prepared by a method analogous to that described in, for example, Example 1, step 1.

4-methoxy-2-methyl-5-[2-methylsulfonyl-4-(trifluoromethyl)phenyl]-6-propoxy-pyridazin-3-one To a mixture of 4-methoxy-2-methyl-5-[2-methylsulfonyl-4-(trifluoromethyl)phenyl]-1H-pyridazine-3,6-dione (0.09 g, 0.24 mmol) and potassium carbonate (0.17 g, 1.19 mmol) in N,N-dimethylformamide (1.4 g, 1.5 ml, 19 mmol) at room temperature was added 1-iodopropane (0.045 g, 0.026 ml, 0.26 mmol). The resulting yellow mixture was stirred for 3 hours and then poured into water and extracted with ethyl acetate. The organic extracts were washed with brine, filtered through a phase-separation cartridge and the filtrate evaporated. The crude residue was purified by flash chromatography (30-80% ethyl acetate in hexanes, 13 min, 4 g silica) to give 4-methoxy-2-methyl-5-[2-methylsulfonyl-4-(trifluoromethyl)phenyl]-6-propoxy-pyridazin-3-one as a pale yellow oil (0.099 g, 0.236 mmol, 99.0% yield).

1H NMR (400 MHz, CDCl$_3$): δ 8.41 (1H, br d), 7.94 (1H, br dd), 7.39 (1H, d), 4.10 (3H, s), 4.04-4.00 (2H, m), 3.72 (3H, s), 2.99 (3H, s), 1.57-1.52 (2H, m), 0.76 (3H, t).

4-methoxy-2-methyl-5-[2-methylsulfonyl-4-(trifluoromethyl)phenyl]-1H-pyridazine-3,6-dione To a solution of sodium nitrite (0.11 g, 1.6 mmol) in concentrated sulphuric acid (3 ml) at 0° C. was added dropwise a suspension of 6-amino-4-methoxy-2-methyl-5-[2-methylsulfonyl-4-(trifluoromethyl)phenyl]pyridazin-3-one (0.51 g, 1.352 mmol) in glacial acetic acid (6.294 g, 6 ml, 105 mmol). The resulting mixture was allowed to warm to room temperature and stirred for 40 min. It was then cooled to 0° C. and water (9 ml) was added dropwise. The resulting suspension was stirred for 60 minutes at room temperature, then diluted with water (10 ml) and the precipitate collected by filtration, washed with water and dried in a vacuum oven at 55° C. overnight to afford 4-methoxy-2-methyl-5-[2-methylsulfonyl-4-(trifluoromethyl)phenyl]-1H-pyridazine-3,6-dione as an off-white solid (0.35 g, 0.92 mmol, 68.25% yield).

1H NMR (400 MHz, MeOD): δ 8.38 (1H, br d), 8.08 (1H, br dd), 7.62 (1H, d), 3.95 (3H, s), 3.67 (3H, s), 3.14 (3H, s)

6-amino-4-methoxy-2-methyl-5-[2-methylsulfonyl-4-(trifluoromethyl)phenyl]-pyridazin-3-one To a solution of 4-methoxy-2-methyl-5-[2-methylsulfonyl-4-(trifluoromethyl)phenyl]-6-nitro-pyridazin-3-one (0.8 g, 1.964 mmol) in ethanol (19.7 g, 25 ml, 411 mmol) at 80° C. was added ammonium formate (2.502 g, 39.28 mmol) and palladium hydroxide on carbon (0.5517 g, 3.928 mmol). The resulting black mixture was maintained at 80° C. for 1 h (NB Sublimation of ammonium formate observed) and then hot-filtered through a short pad of celite, washing with hot ethanol, ethyl acetate and methanol. The filtrate was evaporated and the resulting residue rapidly stirred with water for 10 min and then collected by filtration and dried in a vacuum oven at 55° C. over 2 d (weekend).

Yield: 510 mg (69%, yellow solid)

1H NMR (400 MHz, MeOD): δ 8.42 (1H, br s), 8.14 (1H, br d), 7.65 (1H, d), 3.94 (3H, s), 3.66 (3H, s), 3.16 (3H, s)

4-methoxy-2-methyl-5-[2-methylsulfonyl-4-(trifluoromethyl)phenyl]-6-nitro-pyridazin-3-one To a solution of 4-methoxy-2-methyl-5-[2-methylsulfonyl-4-(trifluoromethyl)phenyl]-pyridazin-3-one (1.81 g, 5.00 mmol) in sulphuric acid (14.7 g, 8 ml, 138 mmol) at 0° C. was added dropwise nitric acid (1.26 g, 0.891 ml, 20.0 mmol). The resulting solution was stirred at 0° C. for 5 min, then allowed to warm to room temperature for 15 min and then heated to 50° C. for a further 2.5 hours. More nitric acid (1.26 g, 0.891 ml, 20.0 mmol) was added and heating continued for a further 2 h. LC-MS still showed presence of starting material. More nitric acid (1.26 g, 0.891 ml, 20.0 mmol) was added and heating continued for a further 1 hour. The reaction mixture was allowed to cool to room temperature and then carefully poured into ice-cold water with rapid stirring. The resulting pale yellow precipitate was filtered, washed with ice-cold water and then dried in a vacuum oven overnight at 55° C.

It was found that the crude product had some acid contaminant. The orange solid was dissolved in dichloromethane and the organic phase washed with water (with a few drops of aqueous sodium hydroxide added—pH 14) and then passed through a phase-separation cartridge. The filtrate was evaporated under reduced pressure to give 4-methoxy-2-methyl-5-[2-methylsulfonyl-4-(trifluoromethyl)phenyl]-6-nitro-pyridazin-3-one (0.8 g, 1.96 mmol, 39.3% Yield) as a pale pink solid.

1H NMR (400 MHz, CDCl$_3$): δ 8.38 (1H, br s), 7.98 (1H, dd), 7.41 (1H, d), 4.20 (3H, s), 3.92 (3H, s), 3.00 (3H, s)

Example 16

4-hydroxy-2-methyl-5-[1-methyl-2-oxo-6-(trifluoromethyl)-3-pyridyl]pyridazin-3-one

2-methoxy-6-(trifluoromethyl)pyridine

To a solution of 6-(trifluoromethyl)pyridin-2-ol (10.0 g, 10.0 g, 61.3 mmol) in dichloromethane (3 ml/mmol, 184 ml) was added silver carbonate (22.8 g, 82.8 mmol, 3.75 mL) and iodomethane (87.0 g, 613 mmol, 38.2 mL) and stirred in the dark for 24 hours. The reaction mixture was then filtered through Celite and washed with dichloromethane. The filtrate was concentrated at 30° C. at 250 mbar, silica added and the residue was purified by chromatography eluting with 0-10% ethyl acetate/hexane. Fractions containing product were combined to give 2-methoxy-6-(trifluoromethyl)pyridine (6.49 g, 36.6 mmol, 59.8% yield).

1H NMR (CDCl$_3$): δ 7.69 (t, J=8.1 Hz, 1H) 7.25 (d, J=7.5 Hz, 1H) 6.91 (d, J=8.6 Hz, 1H) 3.98 (s, 3H);

[2-methoxy-6-(trifluoromethyl)-3-pyridyl]boronic acid

To a solution of 2-methoxy-6-(trifluoromethyl)pyridine (1.0 g, 5.6 mmol) and in diethyl ether (1.2 mL/mmol, 6.8 mL) at −78 C under nitrogen was added nBuLi (2.5 mol/L) in hexanes (4.7 g, 17 mmol, 6.8 mL) over 5 min and allowed to warm up to room temperature over 30 minutes. Boric acid triisopropyl ester (2.1 g, 11 mmol, 2.6 mL) in diethyl ether (1.2 mL/mmol, 6.8 mL) was cooled to −78 C and [2-methoxy-6-(trifluoromethyl)-3-pyridyl]lithium was added to this solution over 15 minutes and then warmed up to room temperature over 30 mins.

Hydrogen chloride (aqueous 25%) (10 mL, 10 mmol) was added and the reaction mixture diluted with water and extracted twice with dichloromethane, passed through a phase separator and reduced under vacuum to give a yellow oil which solidified overnight.

The reaction mixture was adsorbed onto silica and purified by chromatography on silica, eluting with 0-25% ethyl acetate/hexane. Fractions containing product were combined to give [2-methoxy-6-(trifluoromethyl)-3-pyridyl]boronic acid as a yellow solid (707 mg, 3.20 mmol, 59% yield).

1H NMR (11vu941h1, CDCl$_3$): δ 8.29 (d, J=7.5 Hz, 1H) 7.34 (d, J=7.5 Hz, 1H) 5.92 (s, 2H) 4.10 (s, 3H);

4-methoxy-5-[2-methoxy-6-(trifluoromethyl)-3-pyridyl]-2-methyl-pyridazin-3-one To a mixture of 5-chloro-4-methoxy-2-methyl-pyridazin-3-one (400 mg, 2.29 mmol), prepared as described in Example 2, [2-methoxy-6-(trifluoromethyl)-3-pyridyl]boronic acid (0.71 g, 3.20 mmol) sPhos (0.19 g, 0.46 mmol) tris(dibenzylidineacetonyl)bispalladium (0.11 g, 0.11 mmol), potassium phosphate (1.00 g, 4.58 mmol, 0.39 mL) and the reaction mixture diluted with tert-butanol (1.6 mL/mmol, 2.88 g, 38.5 mmol, 3.67 mL). The reaction mixture was heated to 80 C for 50 min. The reaction mixture was diluted with brine and extracted with ethyl acetate (3×). The orange solution was passed through a phase separator, silica added and reduced under vacuum. This was then purified by chromatography, eluting with 0-50% ethyl acetate/hexane. Fractions containing product were combined to give 4-methoxy-5-[2-methoxy-6-(trifluoromethyl)-3-pyridyl]-2-methyl-pyridazin-3-one (545 mg, 0.54 g, 1.73 mmol, 75.46% yield)

5-[2-hydroxy-6-(trifluoromethyl)-3-pyridyl]-4-methoxy-2-methyl-pyridazin-3-one To 4 microwave vials was added in each 1 g of 4-methoxy-5-[2-methoxy-6-(trifluoromethyl)-3-pyridyl]-2-methyl-pyridazin-3-one (4.0 g, 13 mmol) followed by 15 ml of hydrogen bromide (48% aqueous solution) (60 ml) and heated sequentially at 40 C in the microwave for 45 minutes. The reaction mixtures were combined and ethyl acetate was added followed by brine and then extracted with ethyl acetate (3×10 ml), the combined organics passed through a phase separator and reduced under vacuum to give a white solid. This was then purified by chromatography, eluting with 0-50% ethyl acetate/hexane.

Fractions containing product were combined to give 5-[2-hydroxy-6-(trifluoromethyl)-3-pyridyl]-4-methoxy-2-methyl-pyridazin-3-one as a pink solid (1.6 g, 5.3 mmol, 42% yield)

1H NMR (11vz747h1, CDCl$_3$): δ 7.83 (s, 1H) 7.75 (d, J=7.6 Hz, 1H) 6.96 (d, J=7.4 Hz, 1H) 4.18 (s, 3H) 3.82 (s, 3H);

4-methoxy-2-methyl-5-[1-methyl-2-oxo-6-(trifluoromethyl)-3-pyridyl]pyridazin-3-one To a solution of 5-[2-hydroxy-6-(trifluoromethyl)-3-pyridyl]-4-methoxy-2-methyl-pyridazin-3-one (150 mg, 0.49797 mmol) in 1,2-dimethoxyethane (12 ml/mmol, 5.98 mL) was added dipotassium carbonic acid (0.21 g, 1.49 mmol) followed by iodomethane (0.64 g, 4.48 mmol, 0.28 ml) and the reaction mixture heated to reflux (75 C) for 30 min. The reaction mixture was cooled to room temperature and the inorganic solids were filtered and washed with ethyl acetate and the solvent; silica was added and the reaction mixture concentrated under vacuum and purified by chromatography, eluting with 0-35-50% ethyl acetate/hexane.

Fractions containing product were combined to give 4-methoxy-2-methyl-5-[1-methyl-2-oxo-6-(trifluoromethyl)-3-pyridyl]pyridazin-3-one as a white solid (88 mg, 0.28 mmol, 56.06% Yield)

1H NMR (12wk938h1, CDCl$_3$): δ 7.82 (s, 1H) 7.55 (d, J=7.5 Hz, 1H) 6.78 (d, J=7.0 Hz, 1H) 4.16 (s, 3H) 3.80 (s, 3H) 3.70 (d, J=1.1 Hz, 3H)

4-hydroxy-2-methyl-5-[1-methyl-2-oxo-6-(trifluoromethyl)-3-pyridyl]pyridazin-3-one A solution of 4-methoxy-2-methyl-5-[1-methyl-2-oxo-6-(trifluoromethyl)-3-pyridyl]pyridazin-3-one (88 mg, 0.2792 mmol) in morpholine (1 ml, 11.4 mmol) was heated to 100 C for 1.5 h. The reaction mixture was reduced under vacuum, diluted with ethyl acetate, washed with 1M HCl 3 times, reduced under vacuum and triturated with TBME to give 4-hydroxy-2-methyl-5-[1-methyl-2-oxo-6-(trifluoromethyl)-3-pyridyl]pyridazin-3-one as a white solid (48 mg, 0.16 mmol, 57.08% yield)

TABLE C1

Examples of herbicidal compounds of the present invention.

| Compound | R$^1$ | R$^2$ | R$^3$ | NMR |
|---|---|---|---|---|
| 1.001 | —CH$_2$OMe | 2-methyl-6-(methylsulfonyl)-3-(4,5-dihydroisoxazol-3-yl)phenyl | H | 2.24 (3H, s), 3.22 (3H, s), 3.31-3.52 (2H, m), 3.55 (3H, s), 4.61 (2H, t, J = 10.0), 5.54 (2H, s), 7.52 (1H, d, J = 8.2), 7.70 (1H, s), 8.10 (1H, d, J = 8.2) |
| 1.002 | p-methoxybenzyl- | 2-methyl-6-(methylsulfonyl)-3-(4,5-dihydroisoxazol-3-yl)phenyl | H | 2.21 (s, 3H), 3.21 (s, 3H), 3.38 (br. s., 2H), 3.80 (s, 3H), 4.60 (t, J = 10.00 Hz, 2H), 5.33 (s, 2H), 6.87-6.92 (m, 2H), 7.43-7.49 (m, 3H), 7.64 (s, 1H), 8.06 (d, J = 8.19 Hz, 1H) |
| 1.003 | sec-butyl | 2-methyl-6-(methylsulfonyl)-3-(4,5-dihydroisoxazol-3-yl)phenyl | H | |
| 1.004 | (tetrahydropyran-2-yl)-C(CH$_3$)$_2$- | 2-methyl-6-(methylsulfonyl)-3-(4,5-dihydroisoxazol-3-yl)phenyl | H | 1.51-1.66 (3H, m), 1.71-1.88 (3H, m), 2.23 (3H, s), 3.21 (3H, s), 3.75-3.86 (2H, br s), 4.20 (1H, dd, J = 11.6, 4.0), 4.60 (2H, t, J = 9.9), 6.09 (1H, dd, J = 10.7, 2.2), 7.49 (1H, d, J = 8.1), 7.74 (1H, s), 8.08 (1H, d, J = 8.1). |

TABLE C1-continued

Examples of herbicidal compounds of the present invention.

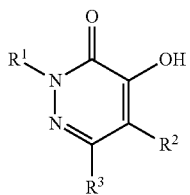

| Compound | R¹ | R² | R³ | NMR |
|---|---|---|---|---|
| 1.005 | CHF₂ | (2-methyl-6-methylsulfonyl-3-(4,5-dihydroisoxazol-3-yl)phenyl) | H | 2.21 (3H, s), 3.20 (3H, s), 3.40 (2H, br s), 4.61 (2H, t, J = 10.0), 6.98 (1H, t, J = 60), 7.49 (1H, d, J = 8.1), 8.08 (1H, s), 8.21 (1H, s, J = 8.1). |
| 1.006 | CHF₂ | (2,4-bis(trifluoromethyl)phenyl) | H | 6.96 (1H, t, J = 60), 7.60 (1H, d, J = 8.1), 7.92 (1H, d, J = 8.1), 8.07 (1H, s), 8.19 (1H, s). |
| 1.007 | Cyclopentyl | (2-methyl-6-methylsulfonyl-3-(4,5-dihydroisoxazol-3-yl)phenyl) | H | 8.09 (1H, d), 7.69 (1H, s), 7.51 (1H, d), 5.46-5.39 (1H, m), 4.60 (2H, t), 3.41 (2H, br s), 3.21 (3H, s), 2.23 (3H, s), 2.18-2.09 (2H, m), 2.04-1.88 (4H, m), 1.78-1.69 (2H, m) |
| 1.008 | Cyclopropyl | (2-methyl-6-methylsulfonyl-3-(4,5-dihydroisoxazol-3-yl)phenyl) | H | 1.00-1.15 (2H, m), 1.20-1.32 (2H, m), 2.23 (3H, s), 3.21 (3H, s), 3.38 (2H, br s), 4.18 (1H, dt, J = 7.7, 3.7), 4.60 (2H, t, J = 10.0), 7.49 (1H, d, J = 8.2), 7.60 (1H, s), 8.08 (1H, d, J = 8.1) |
| 1.009 | Et | (2-chloro-6-methylsulfonyl-3-(4,5-dihydroisoxazol-3-yl)phenyl) | H | 1.47 (3H, t, J = 7.2), 3.27 (3H, s), 3.47 (2H, t, J = 10.1), 4.30 (2H, q, J7.2), 4.63 (2H, t, J = 10.1), 7.68 (1H, d, J = 8.2), 7.74 (1H, s), 8.16 (1H, d, J = 8.2). |

TABLE C1-continued

Examples of herbicidal compounds of the present invention.

| Compound | R¹ | R² | R³ | NMR |
|---|---|---|---|---|
| 1.010 | Et | 2,3,6-trichlorophenyl | H | 7.71 (1H, s), 7.56 (1H, d), 7.30 (1H, d), 4.30 (2H, q), 1.46 (3H, t) |
| 1.011 | Et | 2,6-dichlorophenyl | H | 7.63 (1H, s), 7.43 (1H, d), 7.34-7.30 (1H, m), 4.30 (2H, br d), 1.47 (3H, br t) |
| 1.012 | i-Pr | 2-methyl-6-(methylsulfonyl)-3-(4,5-dihydroisoxazol-3-yl)phenyl | H | 1.45 (6H, d, J = 6.4), 2.24 (3H, s), 3.22 (3H, s), 3.39 (2H, br s), 4.61 (2H, t, J = 10.2), 5.22-5.38 (1H, m), 7.52 (1H, d, J = 8.1), 7.70 (1H, s), 8.08 (1H, d, J = 8.1). |
| 1.013 | i-Pr | 2-(methylsulfonyl)-4-(trifluoromethyl)phenyl | H | 8.47 (1H, d), 7.99 (1H, dd), 7.75 (1H, s), 7.55 (1H, d), 5.27 (1H, septet), 3.04 (3H, s), 1.46 (6H, d) |
| 1.014 | i-Pr | 2-chloro-3-(4,5-dihydroisoxazol-3-yl)-4-(methylsulfonyl)phenyl | H | 1.45 (6H, d, J = 7.0), 3.27 (3H, s), 3.47 (2H, t, J = 10.3), 4.63 (2H, t, J = 10.2), 5.30 (1H, m), 7.69 (1H, d, J = 8.1), 7.78 (1H, s), 8.16 (1H, d, J = 8.1). |
| 1.015 | i-Pr | 2,3,6-trichlorophenyl | H | 7.75 (1H, s), 7.56 (1H, d), 7.31 (1H, d), 5.28 (1H, septet), 1.44 (6H, d) |

TABLE C1-continued
Examples of herbicidal compounds of the present invention.
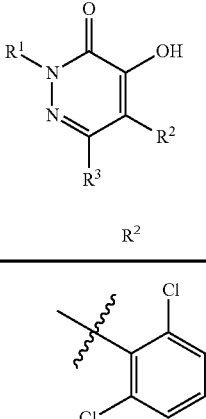
| Compound | R¹ | R² | R³ | NMR |
|---|---|---|---|---|
| 1.016 | i-Pr | 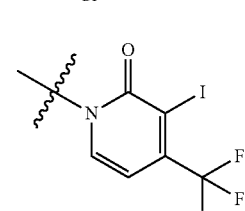 | H | 7.67 (1H, s), 7.45-7.43 (2H, 2 app s), 7.32 (1H, dd), 5.29 (1H, septet), 1.45 (6H, d) |
| 1.017 | Me | 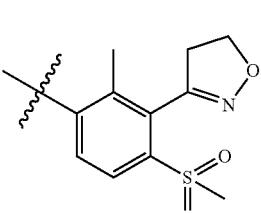 | H | 7.82 (1H, s), 7.74 (1H, d), 6.61 (1H, d), 3.79 (3H, s) |
| 1.018 | Me | 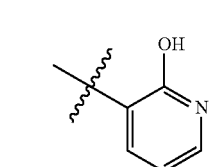 | H | 8.08 (1H, d), 7.64 (1H, s), 7.50 (1H, d), 4.61 (2H, t), 3.91 (3H, s), 3.40 (2H, br s), 3.22 (3H, s), 2.24 (3H, s) |
| 1.019 | Me | 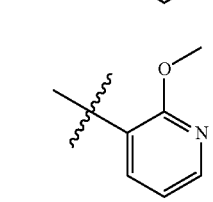 | H | 3.60 (s, 3H), 6.37-6.40 (m, 1H), 7.51-7.52 (m, 1H), 7.77-7.78 (m, 1H), 7.86 (s, 1H), 11.87 (br s, 1H). |
| 1.020 | Me | 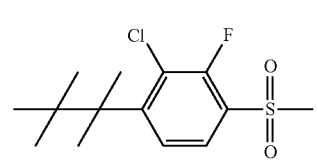 | H | 3.86 (s, 3H), 3.98 (s, 3H), 6.99-7.03 (m, 1H), 7.80-7.82 (m, 1H), 7.91 (s, 1H), 8.22-8.34 (m, 1H) |
| 1.021 | Me | 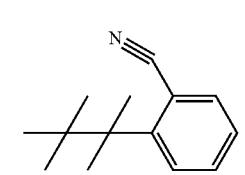 | H | |
| 1.022 | Me |  | H | 7.82 (2H, m), 7.68-7.75 (1H, m), 7.52-7.60 (2H, m), 3.89 (3H, s) |

TABLE C1-continued

Examples of herbicidal compounds of the present invention.

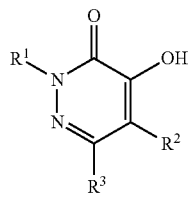

| Compound | R¹ | R² | R³ | NMR |
|---|---|---|---|---|
| 1.023 | Me | (1-substituted-4-[4-(trifluoromethyl)phenyl]pyridin-2(1H)-one) | H | 3.66 (3H, s); 6.66-6.70 (1H, dd); 6.83 (1H, d); 7.64-7.66 (1H, d); 7.78-7.82 (2H, d); 7.85 (1H, s); 7.91-7.93 (2H, d). |
| 1.024 | Me | (1-substituted-3-(pyrimidin-5-yl)-4-(trifluoromethyl)pyridin-2(1H)-one) | H | 9.22 (1H, s), 8.80 (2H, s), 7.91 (2H, m), 6.83 (1H, d), 3.82 (3H, s) |
| 1.025 | Me | (1-substituted-5-morpholino-4-(trifluoromethyl)pyridin-2(1H)-one) | H | 7.90 (1H, s), 7.25 (1H, s), 6.99 (1H, s), 3.87 (3H, s), 3.78 (4H, m), 2.86 (4H, m) |
| 1.026 | Me | (1-substituted-3-morpholino-4-(trifluoromethyl)pyridin-2(1H)-one) | H | 7.87 (1H, s), 7.22 (1H, d), 6.45 (1H, d), 3.86 (3H, s), 3.79 (4H, m), 3.17 (4H, br m) |
| 1.027 | Me | (1-substituted-4-(methylthio)pyridin-2(1H)-one) | H | 2.40 (3H, s); 3.64 (3H, s); 6.14-6.20 (2H, m); 7.32-7.34 (1H, d); 7.76 (1H, s). |

TABLE C1-continued

Examples of herbicidal compounds of the present invention.

| Compound | R¹ | R² | R³ | NMR |
|---|---|---|---|---|
| 1.028 | Me | 4-methylsulfonyl-2-(trifluoromethyl... | H | 8.48 (1H, br d), 8.00 (1H, dd), 7.69 (1H, s), 7.54 (1H, d), 3.90 (3H, s), 3.03 (3H, s) |
| 1.029 | Me | 2-methylsulfinyl-4-(trifluoromethyl)phenyl | H | 8.47 (1H, d), 7.86 (1H, dd), 7.68 (1H, s), 7.48 (1H, d), 3.90 (3H, s), 2.67 (3H, s) |
| 1.030 | Me | 4-methylsulfonyl-2,3-dihydro-1-benzofuran-7-yl | H | 3.09 ppm (3H, s); 3.90 ppm (3H, s); 5.11 ppm (2H, s); 5.47 ppm (2H, s); 7.53 ppm (1H, d); 7.71 ppm (1H, s); 7.93 ppm (1H, d) |
| 1.031 | Me | spiro[1,3-dioxolane-2,4'-thiochromane] derivative | H | 2.24 (3H, s); 2.62 ppm (2H, m); 2.78 ppm (3H, s); 3.52 ppm (2H, m); 3.90 ppm (3H, s); 4.20 ppm (2H, m); 4.31 ppm (2H, m); 7.19 ppm (1H, s); 7.59 ppm (1H, s) |
| 1.032 | Me | 2-chloro-3-(4,5-dihydroisoxazol-3-yl)-4-methylsulfonylphenyl | H | 3.27 (3H, s), 3.47 (2H, t, J = 10.2), 3.90 (3H, s), 4.63 (2H, t, J = 10.2), 7.68 (1H, d, J = 8.1), 7.72 (1H, s), 8.16 (1H, d, J = 8.1). |
| 1.033 | Me | 2,4-bis(trifluoromethyl)phenyl | H | 8.07 (1H, s), 7.91 (1H, d), 7.62 (1H, s), 7.54 (1H, d), 3.90 (3H, s) |

TABLE C1-continued

Examples of herbicidal compounds of the present invention.

| Compound | R¹ | R² | R³ | NMR |
|---|---|---|---|---|
| 1.034 | Me | (2-chloro-3-(2-methoxyethoxy)-6-(methylsulfonyl)phenyl) | H | 3.35 ppm (3H, s); 3.49 ppm (3H, s); 3.87 ppm (2H, t); 3.90 ppm (3H, s); 4.47 ppm (2H, t); 7.35 ppm (1H, d); 7.71 ppm (1H, s); 8.00 ppm (1H, d) |
| 1.035 | Me | (2,4-dimethyl-1,1-dioxo-3-oxo-2,3-dihydrobenzo[d]isothiazol-5-yl) | H | 2.70 ppm (3H, s); 3.27 ppm (3H, s); 3.92 ppm (3H, s); 7.63 ppm (1H, s); 7.70 ppm (1H, d); 7.87 ppm (1H, d) |
| 1.036 | Me | (2-(methylsulfinyl)phenyl) | H | 8.18 (1H, dd), 7.72 (1H, td), 7.70 (1H, s), 7.61 (1H, td), 7.33 (1H, dd), 3.89 (3H, s), 2.66 (3H, s) |
| 1.037 | Me | (3-(3-chlorophenyl)-1-methyl-2-oxo-4-(trifluoromethyl)-1,2-dihydropyridin-1-yl) | H | 7.85 (1H, s), 7.76 (1H, d), 7.42-7.40 (2H, m), 7.31 (1H, m), 7.22-7.20 (1H, m), 6.72 (1H, d), 3.78 (3H, s) |
| 1.038 | Me | (1-methyl-3-(m-tolyl)-2-oxo-4-(trifluoromethyl)-1,2-dihydropyridin-1-yl) | H | 7.88 (1H, s), 7.75 (1H, d), 7.34-7.31 (1H, m), 7.25-7.24 (1H, m), 7.12 (1H, s), 7.09 (1H, d), 6.74 (1H, d), 3.81 (3H, s), 2.40 (3H, s) |
| 1.039 | Me | (2-(trifluoromethyl)-1,8-naphthyridin-3-yl) | H | 9.24 (1H, dd), 8.64 (1H, s), 8.61 (1H, dd), 7.84 (1H, dd), 7.77 (1H, s), 3.85 (3H, s) |

TABLE C1-continued

Examples of herbicidal compounds of the present invention.

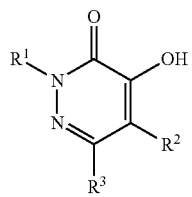

| Compound | R¹ | R² | R³ | NMR |
|---|---|---|---|---|
| 1.040 | Me | (pyridine with CH₂-N(Me)SO₂Me and CF₃) | H | 7.81 (1H, d), 7.75 (1H, d), 7.63 (1H, s), 4.62 (2H, s), 3.90 (3H, s), 2.99 (3H, s), 2.90 (3H, s) |
| 1.041 | Me | (2-tert-butylphenyl ethylsulfinyl) | H | 8.10 (1H, dd), 7.74 (1H, s), 7.70 (1H, td), 7.62 (1H, td), 7.35 (1H, dd), 3.90 (3H, s), 2.89-2.80 (1H, m), 2.77-2.68 (1H, m), 1.20 (3H, t) |
| 1.042 | Me | (2-tert-butylphenyl ethylsulfonyl) | H | 8.16 (1H, dd), 7.74 (1H, td), 7.72 (1H, s), 7.67 (1H, td), 7.37 (1H, dd), 3.88 (3H, s), 3.01 (2H, q), 1.21 (3H, t) |
| 1.043 | Me | (2-tert-butylphenyl isopropylsulfinyl) | H | 8.06 (1H, dd), 7.76 (1H, s), 7.68 (1H, td), 7.61 (1H, td), 7.36 (1H, dd), 3.90 (3H, s), 2.72 (1H, septet), 1.10 (3H, d), 1.08 (3H, d) |
| 1.044 | Me | (2-tert-butylphenyl isopropylsulfonyl) | H | 8.14 (1H, dd), 7.74-7.71 (1H, m), 7.73 (1H, s), 7.65 (1H, td), 7.37 (1H, dd), 3.88 (3H, s), 3.05 (1H, septet), 1.20 (6H, br d) |
| 1.045 | Me | (2-F, 3-Me, 4-Cl phenyl) | H | 2.37 ppm (3H, d); 3.87 ppm (3H, s); 7.29 ppm (2H, m); 7.79 ppm (1H, d) |
| 1.046 | Me | (2-methylsulfonylphenyl) | H | 8.21 (1H, dd), 7.77-7.66 (2H, m), 7.71 (1H, s), 7.37 (1H, dd), 3.89 (3H, s), 2.99 (3H, s) |

TABLE C1-continued

Examples of herbicidal compounds of the present invention.

| Compound | R¹ | R² | R³ | NMR |
|---|---|---|---|---|
| 1.047 | Me | (butyl-sulfinyl-2-tert-butylphenyl group) | H | 8.12 (1H, dd), 7.72 (1H, s), 7.69 (1H, td), 7.60 (1H, td), 7.33 (1H, dd), 3.89 (3H, s), 2.74-2.70 (2H, m), 1.75-1.52 (2H, m), 1.44-1.24 (2H, m), 0.85 (3H, t) |
| 1.048 | Me | (2-chloro-3-((tetrahydrofuran-2-yl)methoxymethyl)-6-methylsulfonylphenyl group) | H | 1.61 ppm (1H, m); 1.90 ppm (2H, m); 1.98 ppm (1H, m); 3.35 ppm (3H, s); 3.67 ppm (2H, m); 3.77 ppm (1H, m); 3.84 ppm (1H, m); 3.90 ppm (3H, s); 4.12 ppm (1H, m); 5.26 ppm (2H, m); 7.55 ppm (1H, d); 7.71 ppm (1H, s); 8.17 ppm (1H, d) |
| 1.049 | Me | (2-chloro-3-((2,2,2-trifluoroethoxy)methyl)-6-methylsulfonylphenyl group) | H | 3.26 ppm (3H, s); 3.91 ppm (3H, s); 4.08 ppm (2H, q); 5.42 ppm (2H, s); 7.61 ppm (1H, d); 7.72 ppm (1H, s): 8.19 ppm (1H, d) |
| 1.050 | Me | (2,3-dichloro-6-methylsulfonylphenyl group) | H | 3.34 ppm (3H, s); 3.89 ppm (3H, s); 7.52 ppm (1H, d); 7.70 ppm (1H, s); 8.19 ppm (1H, d) |
| 1.051 | Me | (butylsulfonyl-2-tert-butylphenyl group) | H | 8.16 (1H, dd), 7.75-7.72 (1H, m), 7.72 (1H, s), 7.66 (1H, td), 7.36 (1H, dd), 3.88 (3H, s), 2.99 (2H, app t), 1.59 (2H, br d), 1.37-1.28 (2H, m), 0.85 (3H, t) |
| 1.052 | Me | (1-(2-(trifluoromethyl)phenyl)-4-(trifluoromethyl)-2-oxo-1,2-dihydropyridin-3-yl group) | H | 7.86 (1H, s), 7.77 (1H, d), 7.64-7.60 (1H, m), 7.57-7.52 (1H, m), 7.47 (1H, d), 7.28 (1H, br d), 6.57 (1H, d), 3.85 (3H, s) |

TABLE C1-continued
Examples of herbicidal compounds of the present invention.
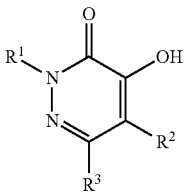
| Compound | R¹ | R² | R³ | NMR |
|---|---|---|---|---|
| 1.053 | Me | 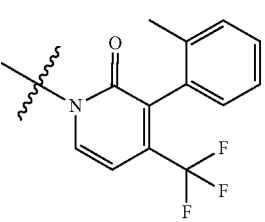 [SMILES: *n1ccc(C(F)(F)F)c(-c2ccccc2C)c1=O] | H | 7.82 (1H, s), 7.76 (1H, d), 7.30-7.19 (3H, m), 7.08 (1H, d), 6.73 (1H, d), 3.77 (3H, m), 2.12 (3H, s) |
| 1.054 | Me | 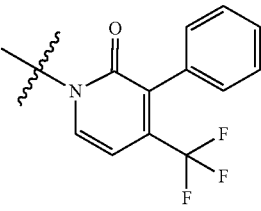 [SMILES: *n1ccc(C(F)(F)F)c(-c2ccccc2)c1=O] | H | 7.85 (1H, s), 7.73 (1H, d), 7.42-7.40 (3H, m), 7.28-7.26 (2H, m), 6.72 (1H, d), 3.78 (3H, s) |
| 1.055 | Me | 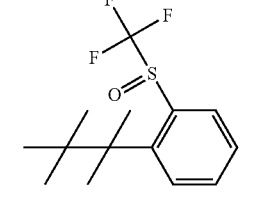 | H | 8.26-8.24 (1H, m), 7.78-7.76 (2H, m), 7.68 (1H, s), 7.42-7.40 (1H, m), 3.90 (3H, s) |
| 1.056 | Me | 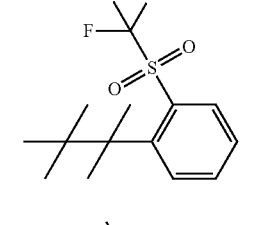 | H | 8.27 (1H, d), 7.91 (1H, td), 7.77 (1H, td), 7.65 (1H, s), 7.51 (1H, dd), 3.89 (3H, s) |
| 1.057 | Me | 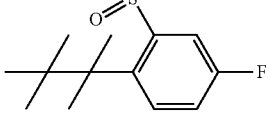 | H | 7.90 (1H, dd), 7.67 (1H, s), 7.36-7.27 (2H, m), 3.89 (3H, s), 2.64 (3H, s) |
| 1.058 | Me | 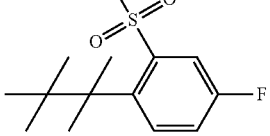 | H | 7.93 (1H, dd), 7.69 (1H, s), 7.46-7.42 (1H, m), 7.37 (1H, dd), 3.88 (3H, s), 3.00 (3H, s) |

TABLE C1-continued

Examples of herbicidal compounds of the present invention.

| Compound | R¹ | R² | R³ | NMR |
|---|---|---|---|---|
| 1.059 | Me | (2-methylsulfinyl-4-chloro-tert-butylphenyl) | H | 8.14 (1H, d), 7.66 (1H, s), 7.57 (1H, dd), 7.27 (1H, d), 3.87 (3H, s), 2.66 (3H, s) |
| 1.060 | Me | (1-(3-cyano-4-methoxy-2-oxopyridin-1-yl)ethyl) | H | 3.64 (3H, s); 3.99 (3H, s); 6.14-6.16 (1H, d); 7.68-7.70 (1H, d); 7.89 (1H, s). |
| 1.061 | Me | (2-methylsulfonyl-4-chloro-tert-butylphenyl) | H | 8.20 (1H, d), 7.70 (1H, dd), 7.68 (1H, s), 7.31 (1H, d), 3.88 (3H, s), 3.00 (3H, s) |
| 1.062 | Me | (3-methyl-2-oxopyridin-1-yl) | H | 2.02 (3H, s); 3.72 (3H, s); 6.22-6.26 (1H, t); 7.39-7.41 (2H, d); 7.84 (1H, s); 11.7-11.9 (1H br s). |
| 1.063 | Me | (2-fluoro-3-methoxy-4-chlorophenyl) | H | 3.88 ppm (3H, s); 4.02 ppm (3H, d); 7.19 ppm (1H, dd); 7.28 ppm (1H, dd); 7.81 ppm (1H, d) |
| 1.064 | Me | (2-fluoro-3-dimethylamino-4-chlorophenyl) | H | 2.92 ppm (6H, 2s); 3.88 ppm (3H, s); 7.15 ppm (1H, dd); 7.26 ppm (1H, dd); 7.80 ppm (1H, d) |
| 1.065 | Me | (4-methyl-2-oxopyridin-1-yl) | H | 2.18 (3H, s); 3.70 (3H, s); 6.18-6.20 (1H, dd); 6.30 (1H, s); 7.40-7.42 (1H, d); 7.82 (1H, s); 11.7-11.9 (1H br s). |
| 1.066 | Me | (3-cyano-4-hydroxy-2-oxopyridin-1-yl) | H | 3.70 (3H, s); 6.17-6.19 (1H, d); 7.70-7.72 (1H, d); 7.87 (1H, s). |

TABLE C1-continued

Examples of herbicidal compounds of the present invention.

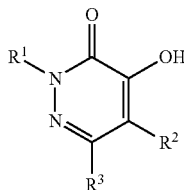

| Compound | R¹ | R² | R³ | NMR |
|---|---|---|---|---|
| 1.067 | Me | (3-position of 2-methyl-6-(trifluoromethyl)pyridine) | H | 7.74 (1H, d), 7.66 (1H, s), 7.62 (1H, d), 3.90 (3H, s), 2.58 (3H, s) |
| 1.068 | Me | (3-position of 2-methyl-6-(1-fluoroethyl)pyridine) | H | 7.83 (1H, d), 7.67 (1H, s), 7.59 (1H, d), 5.90 (1H, dq), 3.90 (3H, s), 2.59 (3H, s), 1.76 (3H, dd) |
| 1.069 | Me | (2-isoquinolin-1(2H)-onyl) | H | 3.72 (3H, s); 6.70-6.72 (1H, d); 7.30-7.32 (1H, d); 7.53-7.57 (1H, t); 7.70-7.72 (1H, d); 7.76-7.80 (1H, t); 7.92 (1H, s); 8.21-8.23 (1H, d). |
| 1.070 | Me | (3-methoxy-2-oxo-2H-pyridin-1-yl) | H | 3.79 (3H, s); 3.84 (3H, s); 6.39-6.43 (1H, t); 6.98-7.00 (1H, d); 7.08-7.10 (1H, d); 7.78 (1H, s). |
| 1.071 | Me | (4-cyano-2-(trifluoromethyl)phenyl) | H | 8.10 (1H, s), 7.94 (1H, dd), 7.60 (1H, s), 7.54 (1H, d), 3.89 (3H, s) |
| 1.072 | Me | (3-position of 2-((2-methoxyethoxy)methyl)-6-(trifluoromethyl)pyridine) | H | 7.88 (1H, d), 7.83 (1H, s), 7.73 (1H, d), 4.70 (2H, s), 3.90 (3H, s), 3.60-3.58 (2H, m), 3.45-3.43 (2H, m), 3.30 (3H, s) |
| 1.073 | Me | (3-position of 2-(methoxymethyl)-6-(trifluoromethyl)pyridine) | H | 7.88 (1H, d), 7.81 (1H, s), 7.74 (1H, d), 4.57 (2H, s), 3.90 (3H, s), 3.35 (3H, s) |

TABLE C1-continued

Examples of herbicidal compounds of the present invention.

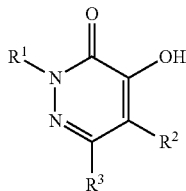

| Compound | R¹ | R² | R³ | NMR |
|---|---|---|---|---|
| 1.074 | Me | (3-(thiophen-2-yl)-6-fluoro-2-oxo-1,8-naphthyridin-4-yl) | H | 8.42 (1H, d), 8.21 (1H, s), 8.19 (1H, s), 7.73 (1H, dd), 7.53 (1H, dd), 7.38 (1H, dd), 7.07 (1H, dd), 3.85 (3H, s) |
| 1.075 | Me | (2-morpholino-6-(trifluoromethyl)pyridin-3-yl) | H | 7.99 (1H, s), 7.87 (1H, d), 7.33 (1H, d), 3.87 (3H, s), 3.73 (4H, m), 3.26 (4H, m) |
| 1.076 | Me | (2-chloro-4-(trifluoromethyl)phenyl) | H | 7.79 (1H, br s), 7.73 (1H, s), 7.63 (1H, dd), 7.54 (1H, d), 3.89 (3H, s) |
| 1.077 | Me | (2,4-dichlorophenyl) | H | 7.71 (1H, d), 7.66 (1H, s), 7.47 (1H, d), 7.39 (1H, d), 3.67 (3H, s) |
| 1.078 | Me | (2-oxo-4-(trifluoromethyl)pyridin-1(2H)-yl) | H | 7.83 (1H, s), 7.75 (1H, d), 6.94 (1H, br m), 6.61 (1H, dd), 3.79 (3H, s) |
| 1.079 | Me | (2-nitro-4-(methylsulfonyl)phenyl) | H | 8.66 (1H, d), 8.28 (1H, dd), 7.72 (1H, s), 7.71 (1H, d), 3.90 (3H, s), 3.18 (3H, s) |

TABLE C1-continued

Examples of herbicidal compounds of the present invention.

| Compound | R¹ | R² | R³ | NMR |
|---|---|---|---|---|
| 1.080 | Me | 2-tert-butyl-phenyl methylsulfonyl | H | |
| 1.081 | Me | 2-tert-butyl-4-bromo-phenyl methylsulfonyl | H | 8.35 (1H, d), 7.86 (1H, dd), 7.68 (1H, s), 7.24 (1H, d), 3.88 (3H, s), 3.00 (3H, s) |
| 1.082 | Me | 4-chloro-2-methyl-phenyl (isopropyl) | H | 7.69 (1H, s), 7.33-7.27 (1H, m), 7.23-7.19 (1H, m), 7.06 (1H, dd), 3.73 (3H, s), 2.06 (3H, d) |
| 1.083 | Me | 3-fluoro-2-methyl-phenyl (isopropyl) | H | 7.69 (1H, s), 7.33-7.27 (1H, m), 7.23-7.19 (1H, m), 7.06 (1H, dd), 3.73 (3H, s), 2.06 (3H, d) |
| 1.084 | Me | 4-cyano-2-methyl-phenyl (isopropyl) | H | 7.82 (1H, br s), 7.73 (1H, dd), 7.71 (1H, s), 7.42 (1H, d), 3.73 (3H, s), 2.21 (3H, s) |
| 1.085 | Me | 3-fluoro-4-methoxy-phenyl (isopropyl) | H | 7.74 (1H, d), 7.40 (1H, app t), 6.92 (1H, dd), 6.86 (1H, dd), 3.80 (3H, s), 3.70 (3H, s) |
| 1.086 | Me | 2-chloro-5-fluoro-phenyl (isopropyl) | H | 7.62 (1H, s), 7.51 (1H, dd), 7.26-7.19 (2H, m), 3.63 (3H, s) |
| 1.087 | Me | 2-tert-butyl-4-nitro-phenyl methylsulfonyl | H | 8.89 (1H, d), 8.63 (1H, dd), 7.77 (1H, d), 3.88 (3H, s), 3.04 (3H, s) |

TABLE C1-continued
Examples of herbicidal compounds of the present invention.
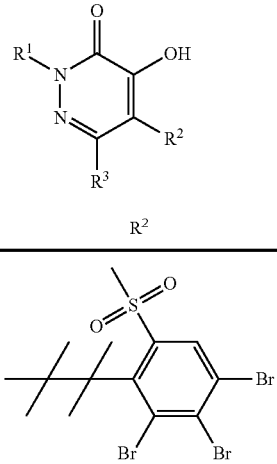
| Compound | R¹ | R² | R³ | NMR |
|---|---|---|---|---|
| 1.088 | Me | 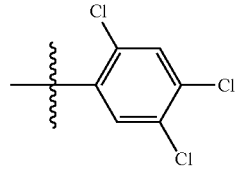 [SMILES: *c1cc(Cl)c(Cl)cc1Cl] | H | 8.45 (1H, s), 7.56 (1H, s), 3.90 (3H, s), 2.98 (3H, s) |
| 1.089 | Me | 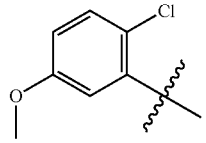 [SMILES: *c1cc(OC)ccc1Cl] | H | 8.00 (1H, s), 7.77 (1H, s), 7.74 (1H, s), 3.72 (3H, s) |
| 1.090 | Me | 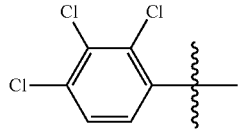 | H | 7.66 (1H, s), 7.42 (1H, d), 6.99-6.94 (2H, m), 3.73 (3H, s), 3.69 (3H, s) |
| 1.091 | Me | 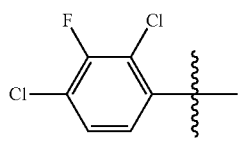 | H | 7.75 (1H, s), 7.74 (1H, d), 7.44 (1H, d), 3.72 (3H, s) |
| 1.092 | Me | 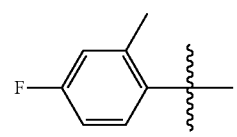 | H | 7.70 (1H, s), 7.66 (1H, dd), 7.29 (1H, dd), 3.69 (3H, s) |
| 1.093 | Me | 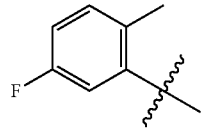 [SMILES: *c1cc(F)ccc1C] | H | 7.66 (1H, s), 7.24 (1H, dd), 7.16 (1H, dd), 7.08 (1H, td), 3.73 (3H, s), 2.16 (3H, s) |
| 1.094 | Me | 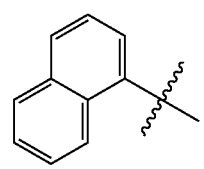 [SMILES: *c1cccc2ccccc12] | H | 7.69 (1H, s), 7.33 (1H, dd), 7.15 (1H, td), 7.08 (1H, dd), 3.73 (3H, s), 2.13 (3H, s) |
| 1.095 | Me |  | H | 8.00 (2H, d), 7.77 (1H, s), 7.61-7.46 (5H, m), 3.79 (3H, s) |

TABLE C1-continued

Examples of herbicidal compounds of the present invention.

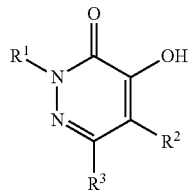

| Compound | R¹ | R² | R³ | NMR |
|---|---|---|---|---|
| 1.096 | Me | 2-F-5-CF₃-phenyl (ethyl linker) | H | 7.91-7.86 (3H, m), 7.60-7.55 (1H, m), 3.73 (3H, s) |
| 1.097 | Me | 2-OMe-6-F-phenyl (ethyl linker) | H | 7.68-7.17 (4H, m), 3.63 (6H, m) |
| 1.098 | Me | 2-Cl-4-Me-phenyl (ethyl linker) | H | 7.75-7.66 (4H, m), 3.74 (3H, s), 2.50 (3H, s) |
| 1.099 | Me | 2,5-diCl-phenyl (ethyl linker) | H | 7.68 (1H, s), 7.57-7.54 (1H, m), 7.48-7.45 (2H, m), 3.68 (3H, s) |
| 1.100 | Me | 2-Cl-5-OCF₂F-phenyl (ethyl linker) | H | 7.55 (1H, s), 7.40 (1H, d), 7.15 (1H, d), 7.11-7.08 (1H, m), 3.743 (3H, s) |
| 1.101 | Me | 2-Cl-5-Me-phenyl (ethyl linker) | H | 7.59 (1H, s), 7.25 (1H, d), 7.07-7.03 (2H, m), 3.74 (3H, s), 2.25 (3H, s) |
| 1.102 | Me | 2,3,5-triCl-phenyl (ethyl linker) | H | 7.68 (1H, s), 7.56 (1H, d), 7.30 (1H, d), 3.88 (3H, s) |

TABLE C1-continued

Examples of herbicidal compounds of the present invention.

| Compound | R¹ | R² | R³ | NMR |
|---|---|---|---|---|
| 1.103 | Me | 2-chloro-4-methoxyphenyl | H | 7.58 (1H, s), 7.18 (1H, d), 6.91 (1H, d), 6.77 (1H, dd), 3.72 (3H, s), 3.71 (3H, s) |
| 1.104 | Me | 4-methoxy-2-nitrophenyl | H | 7.70 (1H, s), 7.61 (1H, d), 7.35 (1H, d), 7.24 (1H, dd), 3.93 (3H, s), 3.88 (3H, s) |
| 1.105 | Me | 2-chloro-4-(methylsulfonyl)phenyl | H | 8.09 (1H, d), 8.00 (1H, dd), 7.79 (1H, d), 7.75 (1H, s), 3.77 (3H, s), 3.26 (3H, s) |
| 1.106 | Me | 3-bromo-2-tert-butyl-6-(methylsulfonyl)phenyl | H | 8.20 (1H, dd), 8.01 (1H, dd), 7.60 (1H, s), 7.55 (1H, app t), 3.90 (3H, s), 2.98 (3H, s) |
| 1.107 | Me | 3-chloro-2-ethoxy-6-(methylsulfonyl)phenyl | H | 7.97 (1H, d), 7.71 (1H, s), 7.32 (1H, d), 4.35 (2H, q), 3.90 (3H, s), 3.30 (3H, s), 1.53 (3H, t) |
| 1.108 | Me | 3-chloro-2-hydroxy-6-(methylsulfonyl)phenyl | H | 7.88 (1H, d), 7.72 (1H, s), 7.13 (1H, d), 3.84 (3H, s), 3.35 (3H, s) |
| 1.109 | Me | 4-chloro-2-nitrophenyl | H | 8.11 (1H, d), 7.70 (1H, dd), 7.69 (1H, s), 7.41 (1H, d), 3.88 (3H, s) |

TABLE C1-continued

Examples of herbicidal compounds of the present invention.

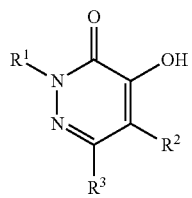

| Compound | R¹ | R² | R³ | NMR |
| --- | --- | --- | --- | --- |
| 1.110 | Me | 2-nitro-4-(trifluoromethyl)phenyl | H | 8.38 (1H, s), 7.98 (1H, d), 7.72 (1H, s), 7.63 (1H, d), 3.89 (3H, s) |
| 1.111 | Me | 2-nitrophenyl | H | 8.12 (1H, dd), 7.76-7.71 (1H, m), 7.73 (1H, s), 7.64-7.60 (1H, m), 7.47 (1H, d), 3.88 (3H, s) |
| 1.112 | Me | 4-fluoro-2-(trifluoromethyl)phenyl | H | 7.62 (1H, s), 7.51 (1H, dd), 7.39-7.32 (2H, m), 3.87 (3H, s) |
| 1.113 | Me | 4-chloro-2-(trifluoromethyl)phenyl | H | 7.79 (1H, d), 7.62 (1H, dd), 7.61 (1H, s), 7.32 (1H, d), 3.89 (3H, s) |
| 1.114 | Me | 2-chlorophenyl | H | 7.75 (1H, s), 7.53-7.51 (1H, m), 7.41-7.36 (3H, m), 3.89 (3H, s) |
| 1.115 | Me | 4-methoxy-2-(trifluoromethyl)phenyl | H | 7.62 (1H, s), 7.30 (1H, d), 7.28 (1H, d), 7.14 (1H, d), 3.89 (3H, s), 3.88 (3H, s) |
| 1.116 | Me | 2-(trifluoromethyl)phenyl | H | 7.80 (1H, d), 7.66-7.63 (2H, overlapping s and m), 7.59-7.55 (1H, m), 7.37 (1H, d), 3.89 (3H, s) |

TABLE C1-continued

Examples of herbicidal compounds of the present invention.

$$\begin{array}{c}\text{structure with pyridazinone core: } R^1-N, N, R^3, R^2, \text{OH}, =O\end{array}$$

| Compound | R¹ | R² | R³ | NMR |
|---|---|---|---|---|
| 1.117 | Me | 2-chloro-6-(trifluoromethyl)phenyl (with methyl substitution at attachment) | H | |
| 1.118 | Me | 2,6-dichlorophenyl (with methyl substitution at attachment) | H | 7.60 (1H, s), 7.43 (1H, d), 7.34-7.30 (1H, m), 3.90 (3H, s) |
| 1.119 | Me | 2-(tert-butyl)-5-(methylsulfonyl)phenyl-methylsulfonyl | H | 8.47 (1H, s), 8.27 (1H, d), , 7.71 (1H, d), 7.67 (1H, s), 3.68 (3H, s), 3.32 (3H, s), 3.15 (3H, s) |
| 1.120 | methylcyclopropyl | 3-(4,5-dihydroisoxazol-3-yl)-2-methyl-4-(methylsulfonyl)phenyl | H | 0.46-0.53 (2H, m), 0.57-0.67 (2H, m), 1.37-1.48 (1H, m), 2.25 (3H, s), 3.22 (3H, s), 3.39 (1H, br s), 4.11 (2H, d, J = 7.2), 4.61 (2H, t, J = 10.1), 7.53 (1H, d, J = 8.1), 7.66 (1H, s), 8.09 (1H, d, J = 8.1) |
| 1.121 | methylcyclopropyl | 2-(methylsulfonyl)-4-(trifluoromethyl)phenyl | H | 8.49 (1H, d), 7.99 (1H, dd), 7.71 (1H, s), 7.57 (1H, d), 4.11 (2H, br m), 3.04 (3H, s), 1.42 (1H, m), 0.64-0.59 (2H, m), 0.50-0.47 (2H, m) |
| 1.122 | methylcyclopropyl | 2-(methylsulfinyl)-4-(trifluoromethyl)phenyl | H | 8.48 (1H, s), 7.87 (1H, d), 7.70 (1H, m), 7.51 (1H, d), 4.11 (2H, m), 2.70 (3H, m), 1.42 (1H, m), 0.62 (2H, m), 0.50 (2H, m) |

TABLE C1-continued

Examples of herbicidal compounds of the present invention.

| Compound | R¹ | R² | R³ | NMR |
|---|---|---|---|---|
| 1.123 | n-Bu | 2,3,6-trichlorophenyl | H | 7.70 (1H, s), 7.56 (1H, d), 7.31 (1H, d), 4.23 (2H, dd), 1.90-1.82 (2H, m), 1.47-1.38 (2H, m), 0.99 (3H, t) |
| 1.124 | n-Bu | 2,6-dichlorophenyl | H | 7.62 (1H, br s), 7.48-7.28 (3H, br m), 4.24 (2H, br m), 1.87 (2H, br m), 1.42 (2H, br m), 0.99 (3H, br m) |
| 1.125 | n-Pr | 2-chloro-3-(4,5-dihydroisoxazol-3-yl)-6-(methylsulfonyl)phenyl | H | 1.02 (3H, t, J = 7.5), 1.84-1.97 (2H, m), 3.27 (3H, s), 3.47 (2H, t, J = 9.9), 4.16-4.25 (2H, m), 4.63 (2H, t, J = 10.2), 7.69 (1H, d, J = 8.1), 7.74 (1H, s), 8.16 (1H, d, J = 8.1). |
| 1.126 | n-Pr | 2-chloro-4-(trifluoromethyl)phenyl | H | 7.79 (1H, br d), 7.74 (1H, s), 7.63 (1H, dd), 7.55 (1H, d), 4.20 (2H, m), 1.96-1.87 (2H, m), 1.02 (3H, t) |
| 1.127 | n-Pr | 2-chloro-6-(trifluoromethyl)phenyl | H | |
| 1.128 | n-Pr | 2,3,6-trichlorophenyl | H | 7.70 (1H, s), 7.56 (1H, d), 7.31 (1H, d), 4.19 (2H, dd), 1.95-1.86 (2H, m), 1.01 (3H, t) |

TABLE C1-continued

Examples of herbicidal compounds of the present invention.

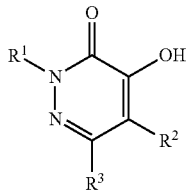

| Compound | R¹ | R² | R³ | NMR |
|---|---|---|---|---|
| 1.129 | n-Pr | 2,6-dichlorophenyl | H | 7.70-7.00 (4H, br m), 4.20 (2H, br m), 1.90 (2H, br m), 1.00 (3H, br m) |
| 1.130 | Ph | 2-methyl-3-(4,5-dihydroisoxazol-3-yl)-4-(methylsulfonyl)phenyl | H | 2.31 (3H, s), 3.23 (3H, s), 3.41 (2H, d, J = 4.6), 4.62 (2H, t, J = 10.0), 7.43-7.49 (1H, m), 7.51-7.60 (3H, m), 7.71-7.76 (2H, m), 7.81 (1H, s), 8.12 (1H, d, J = 8.2). |
| 1.131 | t-Bu | 2-methyl-3-(4,5-dihydroisoxazol-3-yl)-4-(methylsulfonyl)phenyl | H | 1.73 (9H, s), 2.25 (3H, s), 3.22 (3H, s), 3.39 (2H, br s), 4.61 (2H, t, J = 9.9), 7.51 (1H, d, J = 8.1), 7.62 (1H, s), 8.08 (1H, d, J = 8.1). |
| 1.132 | t-Bu | 2,3,6-trichlorophenyl | H | 7.67 (1H, s), 7.55 (1H, d), 7.31 (1H, d), 1.71 (9H, s) |
| 1.133 | t-Bu | 2,6-dichlorophenyl | H | 7.58 (1H, s), 7.44-7.42 (2H, 2 app s), 7.33-7.29 (1H, m), 1.73 (9H, s) |
| 1.134 | Me | 3-tert-butyl-2-(dimethylamino)-6-(trifluoromethyl)pyridin-4-yl | H | 2.88 (6H, s) 3.87 (3H, s) 7.22 (1H, d, J = 7.5 Hz) 7.77 (1H, d, J = 7.0 Hz) 7.82 (1H, s) |

TABLE C1-continued
Examples of herbicidal compounds of the present invention.
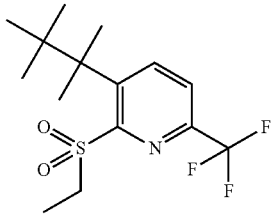 [SMILES: CCS(=O)(=O)c1nc(C(F)(F)F)ccc1C(C)(C)C(C)(C)C]
| Compound | R¹ | R² | R³ | NMR |
|---|---|---|---|---|
| 1.135 | Me |  | H | 1.37-1.48 (3H, m) 3.66 (2H, q, J = 7.5 Hz) 3.88 (3H, s) 7.91 (1H, s) 7.98 (1H, d, J = 8.1 Hz) 8.13 (1H, d, J = 8.1 Hz) |
| 1.136 | cPr | 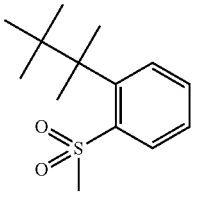 | H | 1.06 (dd, J = 7.52, 1.61 Hz, 2H), 1.22-1.31 (m, 2H), 2.99 (s, 3H), 4.15 (tt, J = 7.67, 3.94 Hz, 1H), 7.36 (dd, J = 7.52, 1.21 Hz, 1H), 7.64-7.77 (m, 3H), 8.20 (dd, J = 7.86, 1.28 Hz, 1H) |
| 1.137 | Me |  | H | |
| 1.138 | Me | 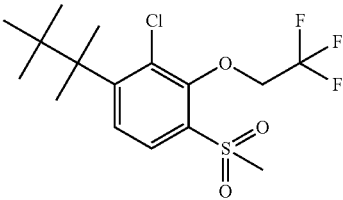 | H | δ 8.02 (br. s., 1H) 7.77-7.93 (m, 3H) 7.63-7.76 (m, 2H) 6.44 (t, J = 7.0 Hz, 1H) 3.60 (s, 3H); |
| 1.139 | Me |  | H | 8.21 (1H, d), 7.73 (1H, dd), 7.70 (1H, s), 7.32 (1H, d), 6.80 (1H, dd), 5.95 (1H, d), 5.50 (1H, d), 3.88 (3H, s), 2.99 (3H, s) |
| 1.140 | Me |  | H | 8.26 (1H, d), 7.79 (1H, dd), 7.70 (1H, s), 7.33 (1H, d), 5.55 (1H, br m), 5.29 (1H, br m), 3.88 (3H, s), 2.99 (3H, s), 2.22 (3H, br m) |
| 1.141 | Me |  | H | 8.51 (1H, d), 8.01 (1H, dd), 7.68 (1H, s), 7.53 (1H, d), 3.89 (3H, s), 3.02 (3H, s) |

TABLE C1-continued

Examples of herbicidal compounds of the present invention.

[Structure: pyridazinone core with R¹ on N, OH, R² and R³ substituents]

| Compound | R¹ | R² | R³ | NMR |
|---|---|---|---|---|
| 1.143 | Me | [3-tert-butyl-1-(3-chlorophenyl)-2-oxo-1,2-dihydropyridin-yl] | H | δ 7.86 (br. s., 1H) 7.65 (d, J = 5.9 Hz, 1H) 7.58 (br. s., 1H) 7.49 (br. s., 1H) 7.40 (br. s., 1H) 6.40 (t, J = 7.0 Hz, 1H) 3.58 (br. s., 3H); |
| 1.144 | CH₃—O—CH₂— | [2-tert-butyl-phenyl with methylsulfonyl group] | H | 8.21 (1H, dd), 7.77-7.74 (1H, m), 7.75 (1H, s), 7.71-7.67 (1H, m), 7.38 (1H, dd), 5.57-5.47 (2H, br m), 3.53 (3H, s), 3.00 (3H, s) |
| 1.145 | CH₃—O—CH₂— | [2-tert-butyl-phenyl with methylsulfinyl group] | H | 8.19 (1H, dd), 7.75 (1H, s), 7.72 (1H, dd), 7.62 (1H, td), 7.34 (1H, dd), 5.55-5.50 (2H, m), 3.54 (3H, s), 2.69 (3H, s) |
| 1.146 | CH₃—O—CH₂— | [4-tert-butyl-phenyl with methylsulfinyl and CF₃ groups] | H | 8.47 (1H, d), 7.87 (1H, dd), 7.74 (1H, s), 7.49 (1H, d), 5.54 (1H, d), 5.51 (1H, d), 3.55 (3H, s), 2.69 (3H, s) |
| 1.147 | Me | [3-tert-butyl-1-(3-nitrophenyl)-2-oxo-1,2-dihydropyridin-yl] | H | δ 8.39-8.43 (m, 1H) 8.30-8.36 (m, 1H) 7.97-8.02 (m, 1H) 7.93 (s, 1 H) 7.81-7.89 (m, 3H) 6.53 (t, J = 7.0 Hz, 1H) 3.67 (s, 3H); |
| 1.148 | Me | [3-tert-butyl-1-(3-fluorophenyl)-2-oxo-1,2-dihydropyridin-yl] | H | 8.11 (s, 1H) 7.90 (dd, J = 5.9, 1.1 Hz, 1H) 7.49 (m, J = 5.9 Hz, 2H) 7.17-7.24 (m, 2H) 6.49 (t, J = 7.0 Hz, 1H) 3.84 (s, 2H); |
| 1.149 | Me | [4-tert-butyl-2,3,6-trifluoropyridinyl] | H | 3.90 (2H, s) 7.73 (1H, d, J = 1.074 Hz) 8.02 (1H, dd, J = 2.149, 1.074 Hz) |

TABLE C1-continued

Examples of herbicidal compounds of the present invention.

| Compound | R¹ | R² | R³ | NMR |
|---|---|---|---|---|
| 1.150 | Me | (3-chloro-2-methoxy-4-tert-butylpyridin-yl) | H | 3.88 (2H, s) 4.07 (2H, s) 6.93 (1H, d, J = 5.37 Hz) 7.73 (1H, s) 8.14 (1H, d, J = 5.37 Hz) 8.15-8.16 (1H, m) |
| 1.151 | Me | (3-fluoro-7-methyl-2-trifluoromethyl-1,8-naphthyridin-6-yl with tert-butyl) | H | 8.26 (s, 1H), 7.82 (d, 1H), 7.71 (s, 1H), 3.91 (s, 3H), 2.87 (d, 3H) |
| 1.152 | Me | (1-(3-trifluoromethylphenyl)-2-oxo-3-tert-butyl-pyridin-yl) | H | δ 7.89 (s, 2H), 7.79-7.81 (m, 5H), 6.51-6.54 (t, 1H), 3.66 (s, 3H); |
| 1.153 | Me | (2,6-dimethoxy-3-tert-butyl-pyridin-yl) | H | 3.85 (3H, s), 3.97 (3H, s), 4.05 (s, 3H), 6.40-6.44 (1H, d), 7.75-7.77 (1H, d), 7.93 (1H, s) |
| 1.154 | Me | (7-methyl-2-trifluoromethyl-1,8-naphthyridin-6-yl with tert-butyl) | H | 8.20 (s, 1H), 8.18 (d, 1H), 7.71 (s, 1H), 7.56 (d, 1H), 3.90 (s, 3H), 2.90 (s, 3H) |
| 1.156 | Me | (1-(3-methoxyphenyl)-2-oxo-3-tert-butyl-pyridin-yl) | H | δ 8.09 (br s, 1H), 7.88-7.90 (d, 1H), 7.50-7.51 (d, 1H), 7.41-7.45 (t, 1H), 6.94-7.03 (m, 2H), 6.48-6.52 (t, 1H), 3.84 (s, 3H), 3.83 (br s, 3H); |

TABLE C1-continued

Examples of herbicidal compounds of the present invention.

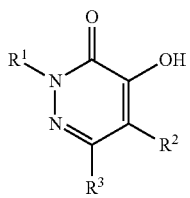

| Compound | R¹ | R² | R³ | NMR |
|---|---|---|---|---|
| 1.157 | Me | (2-tBu-6-Me-3-(4,5-dihydroisoxazol-3-yl)-4-methylsulfonyl-phenyl) | Me | 8.08-8.10 (d, 1H), 7.38-7.40 (d, 1H), 4.58-4.63 (t, 2H), 3.86 (s, 3H), 3.40 (br s, 2H), 3.23 (s, 3H), 2.13 (s, 3H), 2.02 (s, 3H) |
| 1.157 | Me | (3-fluoro-7-methyl-8-(trifluoromethyl)-1,8-naphthyridinyl) | H | 9.18 (d, 1H), 8.35 (s, 1H), 7.98 (dd, 1H), 7.69 (s, 1H), 3.90 (s, 3H) |
| 1.158 | cPr | (2-chloro-6-tBu-3-(4,5-dihydroisoxazol-3-yl)-4-methylsulfonyl-phenyl) | H | 3.30 (s, 6H), 3.47 (t, J = 10.27 Hz, 4H), 4.64 (t, J = 10.14 Hz, 4H), 7.56 (m, J = 8.06 Hz, 2H), 8.19 (m, J = 8.19 Hz, 2H) |
| 1.159 | Me | (1-tBu-3-(2-chlorophenyl)-4-trifluoromethyl-2-oxo-pyridinyl) | H | 7.82-7.80 (2H, m), 7.50-7.48 (1H, m), 7.43-7.35 (2H, m), 7.29-7.27 (1H, m), 6.74 (1H, d), 3.78 (3H, s) |
| 1.160 | Me | (4,5-dibromo-2-tBu-6-methylsulfonyl-phenyl) | H | 8.29 (1H, s), 7.92 (1H, s), 7.68 (1H, s), 3.70 (3H, s), 3.17 (3H, s) |
| 1.161 | Me | (3,4-dibromo-2-tBu-6-methylsulfonyl-phenyl) | H | 8.04 (1H, d), 7.96 (1H, d), 7.58 (1H, s), 3.90 (3H, s), 2.96 (3H, s) |

TABLE C1-continued
Examples of herbicidal compounds of the present invention.
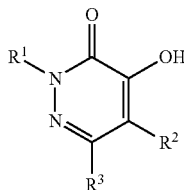
| Compound | R¹ | R² | R³ | NMR |
|---|---|---|---|---|
| 1.163 | C≡C—CH₂— | (2-tert-butyl-6-methyl-3-(methylsulfonyl)phenyl with 4,5-dihydroisoxazol-3-yl substituent) | H | 2.24 (s, 3H), 2.45 (t, J = 2.55 Hz, 1H), 3.22 (s, 3H), 3.40 (br. s., 2H), 4.61 (t, J = 10.00 Hz, 2H), 5.04 (d, J = 2.42 Hz, 2H), 7.51 (d, J = 8.19 Hz, 1H), 7.71 (s, 1H), 8.09 (d, J = 8.19 Hz, 1H) |
| 1.164 | Me | (tert-butyl-trifluoromethyl-morpholinyl-1,8-naphthyridine) | H | 9.13 (m, 1H), 8.08 (s, 1H), 7.70 (s, 1H), 7.28 (s, 1H), 3.95 (m, 4H), 3.90 (s, 3H), 3.42 (m, 4H) |
| 1.165 | Me | (tert-butyl-methoxyphenyl) | H | 7.84 (s, 1H), 7.32-7.34 (dd, 1H), 7.21-7.25 (m, 1H), 6.89-6.92 (m, 2H), 3.79 (s, 3H); |

TABLE C2

Examples of herbicidal compounds of the present invention.

[Structure: pyridazinone core with OH, =O, R¹ on N, R³, and phenyl ring bearing R⁵, R⁶, R⁷, R⁸, R⁹]

| CMP | R¹ | R³ | R⁵ | R⁶ | R⁷ | R⁸ | R⁹ | NMR |
|---|---|---|---|---|---|---|---|---|
| 2.001 | -allyl | H | —S(O)₂Me | H | H | H | H | 8.20 (1H, dd, J = 7.9, 1.3 Hz), 7.71-7.77 (2H, m), 7.64-7.71 (1H, m), 7.38 (1H, dd, J = 7.5, 1.2 Hz), 6.04 (1H, ddt, J = 17.3, 10.0, 6.0, 6.0 Hz), 5.27-5.35 (2H, m), 4.83 (2H, d, J = 19.7 Hz), 3.01 (3H, s) |
| 2.002 | Methoxy-methyl- | H | H | —CF₃ | H | H | H | 8.48 (1H, br s), 8.00 (1H, dd), 7.73 (1H, s), 7.55 (1H, d), 5.52 (2H, br s), 3.54 (3H, s), 3.04 (3H, s) |
| 2.003 | Methoxy-methyl- | H | —SOEt | H | H | H | H | 8.11 (1H, dd), 7.76 (1H, s), 7.70 (1H, td), 7.61 (1H, td), 7.35 (1H, dd), 5.54 (1H, d), 5.51 (1H, d), 3.54 (3H, s), 2.84-2.75 (1H, m), 2.70-2.61 (1H, m), 1.18 (3H, t) |
| 2.004 | Methoxy-methyl- | H | —SO₂Et | H | H | H | H | 8.16 (1H, dd), 7.77-7.73 (1H, m), 7.75 (1H, s), 7.68 (1H, td), 7.39 (1H, dd), 5.52 (2H, br d), 3.53 (3H, s), 3.02 (2H, q), 1.21 (3H, t) |
| 2.005 | Methoxy-methyl- | H | —S(O)₂Me | Cl | H | H | H | 8.20 (1H, d), 7.72 (1H, dd), 7.71 (1H, s), 7.33 (1H, d), 5.51 (2H, br s), 3.53 (3H, s), 3.01 (3H, s) |
| 2.006 | Methoxy-methyl- | H | —S(O)₂Me | F | H | H | H | 7.93 (1H, dd), 7.72 (1H, s), 7.48-7.43 (1H, m), 7.39 (1H, dd), 5.52 (2H, br s), 3.53 (3H, s), 3.01 (3H, s) |

TABLE C2-continued

Examples of herbicidal compounds of the present invention.

| CMP | R¹ | R³ | R⁵ | R⁶ | R⁷ | R⁸ | R⁹ | NMR |
|---|---|---|---|---|---|---|---|---|
| 2.007 | i-butyl | H | Me | —S(O)₂Me | H | (4,4-dimethyl-4,5-dihydroisoxazol-3-yl) | H | 8.09 (1H, d, J = 8.1 Hz), 7.65 (1H, s), 7.48-7.56 (1H, m), 4.61 (2H, t, J = 9.9 Hz), 4.07 (2H, d, J = 7.5 Hz), 3.39 (2H, br. s.), 3.22 (3H, s), 2.35 (1H, dt, J = 13.6, 6.9 Hz), 2.24 (3H, s) 1.00 (6H, d, J = 6.4 Hz) |
| 2.008 | p-methoxy-benzyl- | H | —S(O)₂Me | Cl | H | H | H |  |
| 2.009 | -ethynyl | H | Me | Cl | H | (4,4-dimethyl-4,5-dihydroisoxazol-3-yl) | H |  |
| 2.010 | -ethynyl | H | —S(O)₂Me | —CF₃ | H | H | H | 8.5 (1H, br s), 8.0 (1H, d), 7.7 (1H, s), 7.5 (1H, d), 5.0 (2H, br d), 3.0 (3H, s), 2.4 (1H, m) |
| 2.011 | -ethynyl | H | —S(O)₂Me | Cl— | H | H | H | 8.2 (1H, s), 7.7 (2H, m), 7.3 (1H, d), 5.0 (2H, br d), 3.0 (3H, s), 2.4 (1H, m) |
| 2.012 | CHF₂CH₂— | H | —S(O)₂Me | H | H | H | H | 8.20 (1H, dd, J = 7.9, 1.1 Hz), 7.64-7.81 (3H, m), 7.35-7.43 (1H, m), 4.69 (1H, br. s.), 4.46 (1H, br. |

TABLE C2-continued

Examples of herbicidal compounds of the present invention.

| CMP | R¹ | R³ | R⁵ | R⁶ | R⁷ | R⁸ | R⁹ | NMR |
|---|---|---|---|---|---|---|---|---|
| 2.013 | $CH_3C\equiv CCH_2-$ | H | —S(O)₂Me | H | H | H | H | 8.21 (1H, dd, J = 7.9, 1.3 Hz), 7.72-7.79 (2H, m), 7.69 (1H, dd, J = 7.7, 1.4 Hz), 7.38 (1H, dd, J = 7.6, 1.3 Hz), 4.75-5.15 (1H, m), 3.54-3.80 (1H, m), 3.00 (3H, s), 1.87 (3H, t, J = 2.4 Hz) |
| 2.014 | c-Propyl- | H | —S(O)₂Me | Cl | H | H | H | 8.19 (1H, d, J = 2.1 Hz), 7.69 (1H, dd, J = 8.2, 2.1 Hz), 7.63 (1H, s), 7.30 (1H, d, J = 8.2 Hz), 4.15 (1H, tt, J = 7.7, 3.9 Hz), 3.00 (4H, s), 1.26 (2H, br. s.), 1.06 (2H, dd, J = 7.5, 1.6 Hz) |
| 2.015 | c-Propyl | H | —S(O)₂Me | —CF₃ | H | H | H | 8.48 (1H, s), 7.96-8.01 (1H, m), 7.65 (1H, s), 7.53 (1H, d, J = 7.9 Hz), 4.16 (1H, dt, J = 7.8, 3.7 Hz), 3.03 (3H, s), 1.27 (2H, br. s.), 1.07 (2H, dd, J = 7.5, 1.6 Hz) |
| 2.016 | Ethyl | H | —S(O)₂Me | —CF₃ | H | H | H | 8.5 (1H, s), 8.0 (1H, d), 7.7 (1H, s), 7.5 (1H, d), 4.3 (2H, br q), 3.0 (3H, s), 1.5 (3H, t) |
| 2.017 | Ethyl | H | —S(O)₂Me | Cl | H | H | H | 8.2 (1H, br s), 7.8 (1H, dd), 7.6 (1H, s), 7.4 (1H, d), 4.3 (2H, br m), 3.1 (3H, s), 1.4 (3H, t) |
| 2.018 | i-propyl | H | Cl | H | Cl | H | H | |

TABLE C2-continued

Examples of herbicidal compounds of the present invention.

| CMP | R¹ | R³ | R⁵ | R⁶ | R⁷ | R⁸ | R⁹ | NMR |
|---|---|---|---|---|---|---|---|---|
| 2.019 | Methyl | cPr | 4,5-dihydroisoxazol-3-yl | —S(O)₂Me | H | H | H | 0.71-0.82 (2H, m) 0.87-1.07 (2H, m) 1.21-1.32 (1H, m) 2.18 (3H, s) 3.23 (3H, s) 3.41 (2H, br. s.) 3.81 (3H, s) 4.60 (2H, t, J = 9.9 Hz) 7.48 (1H, d, J = 8.1 Hz) 8.09 (1H, d, J = 8.1 Hz) |
| 2.020 | Methyl | vinyl | 4,5-dihydroisoxazol-3-yl | —S(O)₂Me | H | H | H | 2.13 (3H, s) 3.24 (3H, s) 3.40 (2H, br. s.) 3.93 (3H, s) 4.60 (2H, t, J = 9.9 Hz) 5.29-5.34 (1H, m) 5.95-6.10 (2H, m) 7.41 (1H, d, J = 8.1 Hz) 8.09 (1H, d, J = 8.1 Hz) |
| 2.021 | Methyl | —S(O)₂Et | Me | —S(O)₂Me | H | H | 4,5-dihydroisoxazol-3-yl | 1.40 (3H, t, J = 7.3 Hz) 2.17 (3H, s) 3.22 (3H, s) 3.30-3.61 (2H, m and 2H, br s) 3.95 (3H, s) 4.58 (2H, t, J = 9.9 Hz) 7.51 (1H, d, J = 8.1 Hz) 8.06 (1H, d, J = 8.1 Hz) |
| 2.022 | Methyl | —NO₂ | —S(O)₂Me | —CF₃ | H | H | H | 8.40 (1H, br d), 8.02 (1H, dd), 7.53 (1H, d), 3.99 (3H, s), 2.98 (3H, s) |
| 2.023 | Methyl | CH2=C(CH3)— | Me | H | H | H | 4,5-dihydroisoxazol-3-yl | 1.83 (3H, d, J = 1.6 Hz) 2.16 (3H, s) 3.23 (3H, s) 3.29-3.48 (2H, br s) 3.91 (3H, s) 4.60 (2H, t, J = 9.9 Hz) 4.76 (1H, s) 5.13 (1H, s) 7.38 (1H, d, J = 8.1 Hz) 8.03 (1H, d, J = 8.1 Hz) |

TABLE C2-continued

Examples of herbicidal compounds of the present invention.

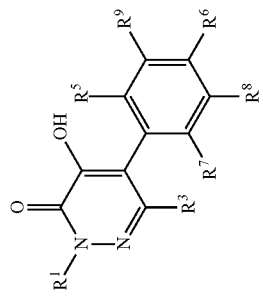

| CMP | R¹ | R³ | R⁵ | R⁶ | R⁷ | R⁸ | R⁹ | NMR |
|---|---|---|---|---|---|---|---|---|
| 2.024 | Methyl | i-Pr | Me | —S(O)₂Me | H | H | ![isoxazoline] | 1.07 (3H, d, J = 7.0 Hz) 1.10 (3H, d, J = 7.0 Hz) 2.13 (3H, s) 2.42-2.54 (1H, m) 3.24 (3H, s) 3.33-3.50 (2H, br s) 3.88 (3H, s) 4.60 (2H, t, J = 10.2 Hz) 7.40 (1H, d, J = 8.1 Hz) 8.08 (1H, d, J = 8.6 Hz) 0039 |
| 2.025 | Methyl | —CN | Me | —S(O)₂Me | H | H | ![isoxazoline] | 2.23 (3H, s) 3.24 (3H, s) 3.30-3.51 (2H, br s) 3.98 (3H, s) 4.61 (2H, t, J = 10.2 Hz) 7.52 (1H, d, J = 8.1 Hz) 8.14 (1H, d, J = 8.6 Hz) |
| 2.026 | Methyl | H | —S(O)₂Me | H | Br | H | ![morpholine] | 7.98 (1H, d), 7.56 (1H, s), 7.45 (1H, d), 3.88 (7H, s overlapping with br s), 3.36 (3H, s), 3.17 (2H, br m), 2.96 (2H, br m) |
| 2.027 | Methyl | H | —S(O)₂Me | Br | Br | H | ![morpholine] | 8.18 (1H, s), 7.55 (1H, s), 4.22-4.17 (1H, m), 3.97-3.95 (1H, m), 3.91-3.83 (3H, m), 3.87 (3H, s), 3.79-3.74 (1H, m), 3.34 (3H, s), 2.99-2.97 (1H, m), 2.73-2.71 (1H, m) |
| 2.028 | Methyl | H | —S(O)₂Me | —C≡C | H | H | H | 8.31 (1H, dd), 7.68 (1H, s), 7.33 (1H, d), 3.88 (3H, s), 3.28 (1H, s), 2.99 (3H, s) |
| 2.029 | Methyl | H | —S(O)₂Me | —C≡C—CH₃ | H | H | H | 8.20 (1H, dd), 7.69 (1H, d), 7.68 (1H, s), 7.27 (1H, d), 3.87 (3H, s), 2.98 (3H, s), |

TABLE C2-continued

Examples of herbicidal compounds of the present invention.

| CMP | R¹ | R³ | R⁵ | R⁶ | R⁷ | R⁸ | R⁹ | NMR |
|---|---|---|---|---|---|---|---|---|
| 2.030 | Methyl | H | —S(O)₂Me | CF₃CH₂—O— | H | H | H | 2.10 (3H, s) 7.75 (1H, d), 7.68 (1H, s), 7.35-7.29 (2H, m), 4.50 (1H, d), 4.46 (1H, d), 3.88 (3H, s), 2.98 (3H, s) |
| 2.031 | Methyl | H | —S(O)₂Me | Me | H | H | H | 8.01 (1H, m), 7.69 (1H, s), 7.54-7.52 (1H, m), 7.25 (1H, d), 3.88 (3H, s), 2.97 (3H, s), 2.51 (3H, s) |
| 2.032 | Methyl | H | —S(O)₂Me | —NO₂ | H | H | H | 9.06 (1H, d), 8.57 (1H, dd), 7.69 (1H, s), 7.61 (1H, d), 3.90 (3H, s), 3.06 (3H, s) |
| 2.033 | Methyl | H | —S(O)₂Me | -phenyl | H | H | H | 8.42 (1H, d), 7.94 (1H, dd), 7.75 (1H, s), 7.68-7.66 (2H, m), 7.53-7.43 (4H, m), 3.90 (3H, s), 3.03 (3H, s) |
| 2.034 | Methyl | H | —S(O)₂Me | NH₂C(O)— | H | H | H | |
| 2.035 | Methyl | H | —S(O)₂Me | Benzyl-S— | H | H | H | 8.05 (1H, d), 7.66 (1H, s), 7.55 (1H, dd), 7.40-7.28 (5H, m), 7.21 (1H, d), 4.25 (2H, s), 3.87 (3H, s), 2.92 (3H, s) |
| 2.036 | Methyl | H | —S(O)₂Me | Benzyl-S(O)₂— | H | H | H | 8.39 (1H, d), 7.94 (1H, dd), 7.65 (1H, s), 7.45 (1H, d), 7.38-7.30 (3H, m), 7.16-7.15 (2H, m), 4.42 (2H, s), 3.89 (3H, s), 2.94 (3H, s) |
| 2.037 | Methyl | H | —S(O)₂Me | ![morpholine sulfonyl] | H | H | H | 8.55 (1H, d), 8.10 (1H, dd), 7.71 (1H, s), 7.58 (1H, d), 3.90 (3H, s), 3.80 (4H, m), 3.12 (4H, m), 3.04 (3H, s) |

TABLE C2-continued

Examples of herbicidal compounds of the present invention.

| CMP | R¹ | R³ | R⁵ | R⁶ | R⁷ | R⁸ | R⁹ | NMR |
|---|---|---|---|---|---|---|---|---|
| 2.038 | Methyl | H | —S(O)₂Me | (CH₃)₂CHN(CH₃)S(O)₂— | H | H | H | 8.59 (1H, d), 8.15 (1H, dd), 7.69 (1H, s), 7.52 (1H, d), 4.31 (1H, pent), 3.89 (3H, s), 3.03 (3H, s), 2.80 (3H, s), 1.10 (6H, d) |
| 2.039 | Methyl | —NH₂ | —S(O)₂Me | CH₃O—CH₂—CF₃ | H | H | H | |
| 2.040 | Methyl | H | —S(O)₂Me | CH₃O—CH₂—CF₃ | H | H | H | 8.16 (1H, br d), 7.71 (1H, br dd), 7.69 (1H, s), 7.35 (1H, d), 4.58 (2H, s), 3.88 (3H, s), 3.48 (3H, s), 2.99 (3H, s) |
| 2.041 | Methyl | CH₃—O— | —S(O)₂Me | —CF₃ | H | H | H | 8.43 (1H, br d), 7.97 (1H, br dd), 7.47 (1H, d), 3.78 (3H, s), 3.75 (3H, s), 3.01 (3H, s) |
| 2.042 | Methyl | H | —S(O)₂Me | —C(O)OH | H | H | H | 8.16 (1H, d), 7.73 (1H, dd), 7.69 (1H, s), 7.34 (1H, d), 4.62 (2H, s), 3.86 (3H, s), 3.76 (1H, pent), 2.99 (3H, s), 1.27 (6H, d) |
| 2.043 | Methyl | H | —S(O)₂Me | i-Pr-O—CH₂— | H | H | H | |
| 2.044 | Methyl | H | —S(O)₂Me | c-hexyl-CH₂—O—CH₂— | H | H | H | |
| 2.045 | Methyl | H | —S(O)₂Me | [neopentyl-O-CH₂CH₂-tetrahydropyranyl-CH₂] | H | H | H | |
| 2.046 | Methyl | H | —S(O)₂Me | [neopentyl-O-CH₂CH₂-morpholinyl] | H | H | H | |

TABLE C2-continued

Examples of herbicidal compounds of the present invention.

| CMP | R¹ | R³ | R⁵ | R⁶ | R⁷ | R⁸ | R⁹ | NMR |
|---|---|---|---|---|---|---|---|---|
| 2.047 | Methyl | H | —S(O)₂benzyl | —CF₃ | H | H | H | 7.90 (1H, dd), 7.69 (1H, br d), 7.64 (1H, s), 7.53 (1H, d), 7.34-7.31 (1H, m), 7.26-7.22 (2H, m), 7.08-7.07 (2H, m), 4.28 (2H, s), 3.91 (3H, s) |
| 2.048 | Methyl | H | —S(O)₂N(CH₃)(i-Pr) | —CF₃ | H | H | H | 8.30 (1H, d), 7.94 (1H, dd), 7.73 (1H, s), 7.56 (1H, d), 3.88 (3H, s), 3.65-3.62 (4H, m), 2.98 (4H, br s) |
| 2.049 | Methyl | H | [morpholine sulfonyl group] | —CF₃ | H | H | H | 8.43 (1H, br d), 7.96 (1H, dd), 7.47 (1H, d), 4.17 (2H, q), 3.76 (3H, s), 3.01 (3H, s), 1.19 (3H, t) |
| 2.050 | Methyl | EtO— | —S(O)₂Me | —CF₃ | H | H | H | 8.43 (1H, br d), 7.96 (1H, dd), 7.47 (1H, d), 4.05 (2H, t), 3.76 (3H, s), 3.01 (3H, s), 1.61-1.52 (2H, m), 0.78 (3H, t) |
| 2.051 | Methyl | nPr-O— | —S(O)₂Me | —CF₃ | H | H | H | 8.42 (1H, br d), 7.96 (1H, dd), 7.44 (1H, d), 5.01 (1H, pent), 3.76 (3H, s), 3.01 (3H, s), 1.19 (3H, d), 1.16 (3H, d) |
| 2.052 | Methyl | iPr-O— | —S(O)₂Me | —CF₃ | H | H | H | 8.16 (1H, d), 7.75 (1H, dd), 7.69 (1H, s), 7.39 (1H, d), 4.82 (2H, s), 3.97 (2H, q), 3.88 (3H, s), 2.99 (3H, s) |
| 2.053 | Methyl | H | —S(O)₂Me | CF₃CH₂OCH₂— | H | H | H | 8.20 (1H, dd, J = 7.9, 1.1 Hz) 7.81 (1H, td, J = 7.6, 1.4 Hz) 7.74 (1H, td, J = 7.7, 1.3 Hz) 7.70 (1H, s), 7.40 (1H, |
| 2.054 | Vinyl | H | —S(O)₂Me | H | H | H | H | |

TABLE C2-continued
Examples of herbicidal compounds of the present invention.
[Structure shown with R¹, R³, R⁵, R⁶, R⁷, R⁸, R⁹ substituents on pyridazinone-phenyl core]
| CMP | R¹ | R³ | R⁵ | R⁶ | R⁷ | R⁸ | R⁹ | NMR |
|---|---|---|---|---|---|---|---|---|
| 2.055 | H | H | Cl | —S(O)₂Me | H | H | 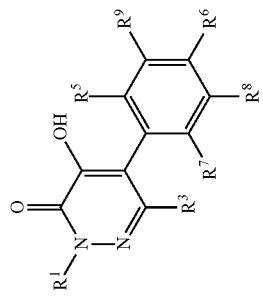 | 8.17 (1H, d, J = 8.1 Hz), 7.76 (1H, s), 7.69 (1H, d, J = 8.6 Hz), 4.64 (2H, t, J = 10.2 Hz), 3.47 (2H, t, J = 10.2 Hz), 3.28 (3H, s) |
| 2.056 | Me | —OH | —S(O)₂Me | —CF₃ | H | H | H | 8.37 (1H, br d), 8.06 (1H, br dd), 7.61 (1H, d), 3.66 (3H, s), 3.14 (3H, s) |
| 2.057 | Me | H | —S(O)₂Me | CH₃O—C₂H₅—O—CH₂— | H | H | H | 8.17 (1H, d), 7.74 (1H, dd), 7.69 (1H, s), 7.34 (1H, d), 4.70 (2H, s), 3.88 (3H, s), 3.74-3.72 (2H, m), 3.64-3.62 (2H, m), 3.42 (3H, s), 2.99 (3H, s) |

TABLE C3

Examples of herbicidal compounds of the present invention.

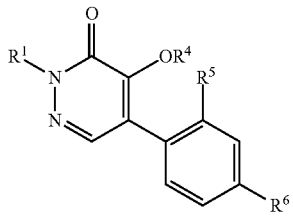

| Cmp | R¹ | R⁴ | R⁵ | R⁶ | NMR |
|---|---|---|---|---|---|
| 3.001 | Methyl | CH₃C(O)— | —S(O)₂Me | —CF₃ | 8.49 (1H, br d), 7.98 (1H, dd), 7.77 (1H, s), 7.52 (1H, d), 3.88 (3H, s), 3.02 (3H, s), 2.21 (3H, s) |
| 3.002 | Methyl | Phenyl-C(O)— | —S(O)₂Me | —CF₃ | 8.46 (1H, br d), 7.97-7.94 (3H, m), 7.83 (1H, s), 7.64-7.60 (2H, m), 7.46-7.42 (2H, m), 3.91 (3H, s), 3.09 (3H, s) |
| 3.003 | Methyl | CH₃OC(O)— | —S(O)₂Me | —CF₃ | 8.48 (1H, br d), 8.00 (1H, dd), 7.78 (1H, s), 7.54 (1H, d), 3.90 (3H, s), 3.88 (3H, s), 3.03 (3H, s) |
| 3.004 | Methyl | C₂H₅SC(O)— | —S(O)₂Me | —CF₃ | 8.48 (1H, br d), 7.99 (1H, dd), 7.76 (1H, s), 7.53 (1H, d), 3.89 (3H, s), 3.02 (3H, s), 2.91 (2H, q), 1.30 (3H, t) |
| 3.005 | Methyl | nPr-S(O)₂— | —S(O)₂Me | —CF₃ | 8.44 (1H, br d), 8.03 (1H, br dd), 7.78 (1H, s), 7.64 (1H, d), 3.90 (3H, s), 3.91-3.85 (1H, m), 3.79-3.73 (1H, m), 3.07 (3H, s), 2.01-1.95 (2H, m), 1.10 (3H, t) |
| 3.006 | Methyl | 4-Me-phenyl-S(O)₂— | —S(O)₂Me | —CF₃ | 8.43 (1H, br d), 8.00 (1H, br dd), 7.8 (2H, d), 7.77 (1H, s), 7.65 (1H, d), 7.33 (2H, d), 3.87 (3H, s), 3.06 (3H, s), 2.45 (3H, s) |

TABLE C4

Examples of herbicidal compounds of the present invention.

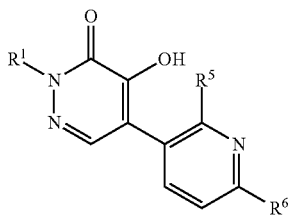

| Compound | R¹ | R⁵ | R⁶ | NMR |
|---|---|---|---|---|
| 4.001 | Ethyl- | —SO₂Me | —CF₃ | 8.1 (1H, d), 8.0 (1H, d), 7.9 (1H, br s), 4.3 (2H, q), 3.4 (3H, s), 1.4 (3H, t) |
| 4.002 | Methyl- | ![oxetanyl-O-] | —CF₃ | |
| 4.003 | Methyl- | —SO₂Me | —CF₃ | 3.41 (3 H, s) 3.86 (3 H, s) 7.85 (1 H, s) 8.00 (1 H, d, J = 8.1 Hz) 8.13 (1 H, d, J = 8.1 Hz) |
| 4.004 | Methyl- | ![dimethylmorpholino-] | —CF₃ | 1.14 (6 H, d, J = 5.9 Hz) 2.58-2.69 (21 H, m) 3.41 (2 H, d, J = 10.7 Hz) 3.64-3.76 (2 H, m) 3.88 (3 H, s) 7.31 (1 H, d, J = 8.1 Hz) 7.86 (1 H, d, J = 7.0 Hz) 7.95 (1 H, s) |

TABLE C4-continued

Examples of herbicidal compounds of the present invention.

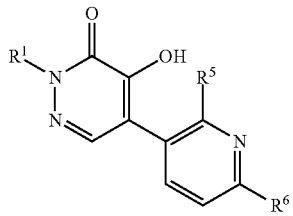

| Compound | R¹ | R⁵ | R⁶ | NMR |
|---|---|---|---|---|
| 4.005 | Methyl- | CH₃—O— | —CF₃ | δ 11.28 (br s, 1 H) 7.97 (d, J = 7.5 Hz, 1 H) 7.77 (s, 1 H) 7.53 (d, J = 7.5 Hz, 1 H) 3.85 (s, 3 H) 3.65 (s, 3 H); |
| 4.006 | Methyl- | —OH | —CF₃ | δ 12.21 (br. s., 1 H) 7.90 (d, J = 8.1 Hz, 1 H) 7.77 (s, 1 H) 7.35 (d, J = 7.0 Hz, 1 H) 3.65 (s, 3 H); |
| 4.007 | Methyl- | HOC(O)CH₂O— | —CF₃ | |
| 4.008 | Methyl- | Ph-O— | —CF₃ | 3.88 (3 H, s) 7.14-7.19 (2 H, m) 7.19-7.24 (1 H, m) 7.36-7.42 (2 H, m) 7.49 (1 H, d, J = 8.1 Hz) 8.01 (1 H, s) 8.07 (1 H, d, J = 8.6 Hz) |
| 4.009 | Methyl | 3-Cl-benzyl-O— | —CF₃ | 3.87 (3 H, s) 5.46 (2 H, s) 7.27-7.35 (3 H, m) 7.40 (1 H, d, J = 7.5 Hz) 7.45 (1 H, s) 7.89 (1 H, s) 7.97 (1 H, d, J = 7.5 Hz) |
| 4.010 | Methyl | [triazolyl-tBu] | —CF₃ | 3.88 (3 H, s) 7.63 (1 H, s) 7.85 (1 H, d, J = 7.5 Hz) 7.95 (1 H, s) 8.11 (1 H, d, J = 8.1 Hz) 9.08 (1 H, s) |
| 4.011 | Methyl | CHF₂CH₂O— | H | δ 7.87-8.10 (m, 2 H) 7.59 (s, 1 H) 7.02 (dd, J = 7.5, 4.8 Hz, 1H) 6.30 (tt, J = 54.8, 3.8 Hz, 1 H) 4.50 (td, J = 15.0, 3.2 Hz, 2 H) 3.53 (s, 3 H); |
| 4.012 | Methyl | C₂H₅OC(O)—O— | —CF₃ | |
| 4.013 | Methyl | CH₂CHCH₂O— | —CF₃ | |
| 4.014 | Methyl | Cl | —CF₃ | 3.90 (3 H, s) 7.75 (1 H, d, J = 8.1 Hz) 7.79 (1 H, s) 7.97 (1 H, d, J = 7.0 Hz) |
| 4.015 | Methyl | —CN | —CF₃ | 3.71 (1 H, s) 7.46-7.53 (1 H, m) 8.10-8.16 (1 H, m) 8.19 (1 H,s) |
| 4.016 | Methyl | [morpholino-SO₂-tBu] | —CF₃ | 3.54-3.63 (4 H, m) 3.76-3.83 (4 H, m) 3.89 (3 H, s) 7.89 (1 H, s) 7.94 (1 H, d, J = 8.1 Hz) 8.10 (1 H, d, J = 8.1 Hz) |
| 4.017 | Methyl | (CH3)₂CHN(CH₃)—SO₂— | —CF₃ | 1.23 (6 H, d, J = 6.4 Hz) 2.99 (3 H, s) 3.88 (3 H, s) 4.20 (1 H, dt, J = 13.4, 6.7 Hz) 7.89 (1 H, s) 7.91 (1 H, d, J = 2.7 Hz) 8.06 (1 H, d, J = 7.5 Hz) |
| 4.018 | Methyl | —S(O)₂Et | —CN | |
| 4.019 | Methyl | —S(O)₂NH₂ | —CF₃ | |

TABLE C5

Examples of herbicidal compounds of the present invention.

[Structure: pyridazinone substituted with naphthyridine bearing R1, R5, R13a, R13b groups]

| Compound | R¹ | R5 | R13a | R13b | NMR |
|---|---|---|---|---|---|
| 5.001 | Ethyl | —CF$_3$ | H | H | 9.3 (1H, m), 8.4 (1H, s), 8.3 (1H, d), 7.7 (1H, s), 7.6 (1H, d), 4.4 (2H, q), 1.5 (3H, t) |
| 5.002 | Methyl | —CF$_3$ | Methyl | Methyl | 2.72 (s, 3 H), 2.83 (s, 3 H), 3.92 (s, 3 H), 7.39 (s, 1 H), 7.72 (s, 1 H), 8.41 (s, 1 H) |

TABLE C6

Examples of herbicidal compounds of the present invention.

[Structure: pyridazinone linked to pyridinone with R¹, R⁷, R⁸ substituents]

| Compound | R¹ | R⁸ | R⁷ | NMR |
|---|---|---|---|---|
| 6.001 | Methyl | Methyl | -phenyl | 2.48 (3 H, s) 3.84 (3 H, s) 7.39-7.4 (1 H, m) 7.47-7.53 (2 H, m) 7.57-7.62 (2H, m) 7.63 (1 H, s) 8.25 (1 H, s) |
| 6.002 | Methyl | Methyl | [thiophen-3-yl] | 2.49 (3 H, s) 3.85 (3 H, s) 7.32-7.37 (1 H, m) 7.55 (1 H, s) 7.63 (1 H, dd, J = 5.4, 1.6 Hz) 8.03-8.08 (1 H, m) 8.22 (1 H, s) |
| 6.003 | Methyl | Methyl | n-butyl | 0.97 (3 H, t, J = 7.3 Hz) 1.41 (21 H, dd, J = 15.0, 7.5 Hz) 1.77-1.87 (2 H, m) 2.42 (3 H, s) 3.83 (3 H, s) 4.19-4.26 (2 H, m) 7.47 (1 H, s) 8.08 (1 H, s) |

TABLE C7

Examples of herbicidal compounds of the present invention.

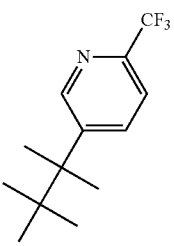 [SMILES: CC(C)(C)C(C)(C)c1ccc(C(F)(F)F)nc1]

| Compound | $R^6$ | $R^9$ | NMR |
|---|---|---|---|
| 7.001 | | 4-CF$_3$-phenyl- | δ 9.51 (s, 1 H) 7.83-7.91 (m, 3 H) 7.79 (d, J = 7.0 Hz, 1 H) 7.75 (d, J = 7.0 Hz, 1 H) 7.68 (d, J = 7.5 Hz, 2 H) 6.46 (t, J = 7.0 Hz, 1 H) 3.61 (s, 3 H) |
| 7.002 | —CF$_3$ | 3-NH$_2$-phenyl- | |
| 7.003 | —CF$_3$ | 3-MeO-phenyl- | 7.83 (1H, s), 7.73 (1H, d), 7.41-7.37 (1H, m), 7.12-7.10 (1H, m), 7.05-7.03 (1H, m), 7.01-6.97 (1H, m), 6.70 (1H, d), 3.79 (3H, s), 3.77 (3H, s) |
| 7.004 | —CF$_3$ | 3-CH$_3$C(O)NH-phenyl- | |
| 7.005 | —CF$_3$ | 3-CF$_3$O-phenyl- | 7.88 (1H, s), 7.79 (1H, d), 7.55-7.51 (1H, m), 7.35-7.29 (2H, m), 7.23 (1H, m), 6.75 (1H, d), 3.79 (3H, s) |
| 7.006 | —CF$_3$ | 4-CH$_3$-phenyl- | 7.85 (1H, s), 7.72 (1H, dd), 7.24 (2H, d), 7.15 (2H, d), 6.71 (1H, d), 3.78 (3H, s), 2.38 (3H, s) |
| 7.007 | —CF$_3$ | 2-CH$_3$,5F-phenyl | 7.86 (1H, s), 7.81 (1H, dd), 7.27 (1H, dd), 7.05 (1H, td), 6.89 (1H, dd), 6.76 (1H, d), 3.79 (3H, s), 2.10 (3H, s) |
| 7.008 | —CF$_3$ | 3-MeS(O)$_2$—NH— | |
| 7.009 | —CF$_3$ | 4-NO$_2$-phenyl | 8.31 (2H, d), 7.87 (1H, s), 7.83 (1H, dd), 7.57 (2H, d), 6.78 (1H, d), 3.79 (3H, s) |
| 7.010 | —CF$_3$ | | 3.85 (3H, s), 6.65 (1H, d), 7.4-7.8 (4H, m), 7.85 (1H, s) |
| 7.011 | —CF$_3$ | 3-vinyl-phenyl- | 3.8 (3H, s), 5.25 1H, d), 5.75 (1H, d), 6.6 (1H, d), 6.7 (1H, dd), 7.2-7.7 (5H, m), 7.8 (1H, s) |
| 7.012 | —CF$_3$ | 3-F-phenyl- | 3.85 (3H, s), 6.6 (1H, d), 7.0-7.7 (5H, m), 7.9 (1H, s) |
| 7.013 | —CF$_3$ | 3-HC(O)-phenyl- | |
| 7.014 | —CF$_3$ | 3-iPr-phenyl- | 1.3 (6H, d), 2.9 (1H, m), 3.85 (3H, s), 6.7 (1H, d), 7.1-7.4 (5H, m), 7.9 (1H, s) |
| 7.015 | —CF$_3$ | 2-MeO,5-iPr-phenyl- | 1.2 (6H, d), 2.9 (1H, m), 3.85 (3H, s), 6.6 (1H, d), 6.9-7.45 (4H, m), 7.9 (1H, s) |
| 7.016 | —CF$_3$ | 3-EtO-phenyl- | 1.4 (3H, t), 3.85 (3H, s), 4.05 (2H, q), 6.6 (1H, d), 6.8-7.7 (5H, m), 7.9 (1H, s) |
| 7.017 | —CF$_3$ | 3,4,5 trifluorophenyl- | 3.85 (3H, s), 6.6 (1H, d), 6.9-7.7 (3H, m), 7.9 (1H, s) |
| 7.018 | —CF$_3$ | 3-CF$_3$-phenyl- | 3.85 (3H, s), 6.6 (1H, d), 7.4-7.7 (4H, m), 7.9 (1H, s) |
| 7.019 | —CF$_3$ | 3-CN-phenyl- | 3.8 (3H, s), 6.7 (1H, d), 7.5-7.7 (4H, m), 7.9 (1H, s) |
| 7.020 | —CF$_3$ | 3-MeS-phenyl- | 2.5 (3H, s), 3.85 (3H, s), 6.6 (1H, d), 7.1-7.7 (5H, m), 7.9 (1H, s) |
| 7.021 | —CF$_3$ | 3,4,5 trimethoxy-phenyl- | 3.89 (3H, s), 3.85 (3H, s), 3.84 (6H, s), 6.5 (2H, s), 6.6 (1H, d), 7.4 (1H, d), 7.9 (1H, s) |
| 7.022 | —CF$_3$ | 3,5 dichlorophenyl- | 3.8 (3H, s), 6.6 (1H, d), 7.2-7.5 (4H, m), 7.9 (1H, s) |
| 7.023 | —CF$_3$ | 3-MeS(O)$_2$-phenyl- | 3.1 (3H, s), 3.8 (3H, s), 6.65 (1H, d), 7.5-8.0 (5H, m), 7.9 (1H, s) |
| 7.024 | —CF$_3$ | 3-(CH$_3$)$_2$N-phenyl- | 3.15 (6H, s), 3.85 (3H, s), 6.7 (1H, d), 7.2-7.55 (5H, m), 7.9 (1H, s) |
| 7.025 | —CF$_3$ | 3-(CH$_3$)$_2$NS(O)$_2$-phenyl- | |
| 7.026 | —CF$_3$ | 3-CN,4-Cl-phenyl- | 3.85 (3H, s), 6.6 (1H, d), 7.2-7.5 (4H, m), 7.85 (1H, s) |
| 7.027 | —CF$_3$ | 3-NO$_2$,4Me phenyl- | 2.65 (3H, s), 3.85 (3H, s), 6.6 (1H, d), 7.4-7.7 (3H, m), 7.9 (1H, s), 8.0 (1H, s) |

TABLE C7-continued

Examples of herbicidal compounds of the present invention.

| Compound | R⁶ | R⁹ | NMR |
|---|---|---|---|
| 7.028 | —CF₃ | (morpholine-N-SO₂- group) | |
| 7.029 | —CF₃ | 2,3-dichlorophenyl- | 3.85 (3H, s), 6.6 (1H, d), 7.15-7.55 (4H, m), 7.9 (1H, s) |
| 7.030 | —CF₃ | 2-Me,3-Cl-phenyl- | 2.2 (3H, s), 3.85 (3H, s), 6.6 (1H, d), 6.95-7.7 (4H, m), 7.9 (1H, s) |
| 7.031 | —CF₃ | 4-CN-phenyl- | 3.85 (3H, s), 6.65 (1H, d), 7.45-7.75 (5H, m), 7.85 (1H, s) |
| 7.032 | —CF₃ | 2-Cl,5-Me-phenyl- | 2.35 (3H, s), 3.85 (3H, s), 6.6 (1H, d), 7.05-7.5 (4H, m), 7.9 (1H, s) |
| 7.033 | —CF₃ | 4-MeO-phenyl- | 3.84 (3H, s), 3.85 (3H, s), 6.6 (1H, d), 6.9-7.4 (5H, m), 7.9 (1H, s) |
| 7.034 | —CF₃ | 2-vinylphenyl- | 3.85 (3H, s), 5.3 (1H, d), 5.8 (1H, d), 6.6 (1H, d), 6.75 (1H, dd), 7.1-7.7 (5H, m), 7.9 (1H, s) |
| 7.035 | —CF₃ | 4-CF₃-phenyl- | 3.85 (3H, s), 6.6 (1H, d), 7.4-7.7 (5H, m), 7.9 (1H, s) |
| 7.036 | —CF₃ | 4-MeS-phenyl- | 2.5 (3H, s), 3.85 (3H, s), 6.6 (1H, d), 7.2-7.7 (5H, m), 7.9 (1H, s) |
| 7.037 | —CF₃ | 4-CH(O)-phenyl- | |
| 7.038 | —CF₃ | 2-Me,4-Cl-phenyl- | 2.15 (3H, s), 3.85 (3H, s), 6.6 (1H, d), 7.05-7.5 (4H, m), 7.9 (1H, s) |
| 7.039 | —CF₃ | 2,4 dichlorophenyl- | 3.85 (3H, s), 6.6 (1H, d), 7.15-7.55 (4H, m), 7.9 (1H, s) |
| 7.040 | —CF₃ | (2,3-dihydro-1,4-benzodioxin-6-yl group) | |
| 7.041 | —CF₃ | 2-Cl,4-CF₃ phenyl- | 3.85 (3H, s), 6.6 (1H, d), 7.15-7.5 (4H, m), 7.9 (1H, s) |
| 7.042 | —CF₃ | 2-Me,4-CN-phenyl- | 2.2 (3H, s), 3.85 (3H, s), 6.65 (1H, d), 7.2-7.6 (4H, m), 7.9 (1H, s) |

TABLE C8

Examples of herbicidal compounds of the present invention.

| Compound | R¹ | R⁵ | R⁶ | NMR |
|---|---|---|---|---|
| 8.001 | Methyl | (morpholin-4-yl group) | —CF₃ | 2.96-3.10 (2 H, m) 3.22-3.33 (2 H, m) 3.45-3.54 (2 H, m) 3.63-3.76 (10 H, m) 3.79 (3 H, s) 7.52 (1 H, s) 8.19 (1 H, s) |

TABLE C9

Examples of herbicidal compounds of the present invention.

| Compound | R⁶ | R⁹ | NMR |
|---|---|---|---|
| 9.001 | —CF₃ | 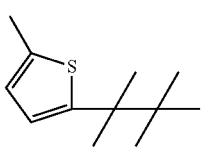 | δ 8.26 (t, J = 8.1 Hz, 1 H) 8.08 (d, J = 8.6 Hz, 1 H) 8.00 (d, J = 8.1 Hz, 1 H) 7.90 (dd, J = 7.0, 2.1 Hz, 1 H) 7.77 (dd, J = 7.0, 2.1 Hz, 1 H) 6.51 (t, J = 7.0 Hz, 1 H) 3.63 (s, 3 H); |
| 9.002 | H | CH2=CH—CH₂— | δ 7.93 (s, 1 H) 7.88 (dd, J = 7.0, 1.6 Hz, 1 H) 7.74 (dd, J = 6.4, 1.6 Hz, 1 H) 6.56 (t, J = 7.0 Hz, 1 H) 5.97-6.08 (m, 1 H) 5.17-5.30 (m, 2 H) 4.71 (dt, J = 5.4, 1.6 Hz, 2 H) 3.77 (s, 3 H) |
| 9.003 | H | Methyl | δ 7.91-7.94 (m, 1 H) 7.88 (dd, J = 7.0, 2.1 Hz, 1 H) 7.80 (dd, J = 6.4, 2.1 Hz, 1 H) 6.54 (t, J = 7.0 Hz, 1 H) 3.77 (s, 3H) 3.66 (s, 3 H) |
| 9.004 | H | 4-MeO-benzyl- | δ 7.91 (s, 1 H) 7.80-7.88 (m, 2 H) 7.28-7.35 (m, 2 H) 6.87-6.92 (m, 2 H) 6.54 (t, J = 7.0 Hz, 1 H) 5.21 (s, 2 H) 3.76 (d, J = 1.1 Hz, 6 H); |
| 9.005 | H | CF₃CH₂— | δ 7.91 (s, 1 H) 7.89 (dd, J = 7.5, 1.6 Hz, 2 H) 7.70-7.75 (m, 1 H) 6.54 (t, J = 7.0 Hz, 1 H) 4.89 (q, J = 8.6 Hz, 2 H) 3.77 (s, 3 H) |
| 9.006 | H | cPr-CH₂— | δ 7.93 (s, 1 H) 7.89 (dd, J = 7.5, 1.6 Hz, 1 H) 7.85 (dd, J = 6.4, 2.1 Hz, 1 H) 6.57 (t, J = 7.0 Hz, 1 H) 3.95 (d, J = 7.5 Hz, 2 H) 3.77 (s, 3 H) 1.29-1.40 (m, 1 H) 0.56-0.63 (m, 2 H) 0.42-0.49 (m, 2 H) |
| 9.007 | H | CH₃C(=CH₂)—CH₂— | δ 7.96 (br. s., 1 H) 7.90 (dd, J = 7.5, 1.6 Hz, 1 H) 7.71 (dd, J = 7.0, 1.6 Hz, 1 H) 6.58 (t, J = 7.0 Hz, 1 H) 4.96 (s, 1 H) 4.67 (s, 3 H) 3.77 (s, 3 H) 1.77 (s, 3 H) |
| 9.008 | H | Benzyl- | δ 7.92 (s, 1 H) 7.81-7.90 (m, 2 H) 7.31 (m, J = 4.3 Hz, 5 H) 6.55 (t, J = 7.0 Hz, 1 H) 5.29 (s, 2 H) 3.76 (s, 3 H) |
| 9.009 | H | CH₃OCH₂CH₂— | δ 7.94 (br. s., 1 H) 7.89 (dd, J = 7.0, 2.1 Hz, 1 H) 7.75 (dd, J = 6.4, 2.1 Hz, 1 H) 6.54 (t, J = 7.0 Hz, 1 H) 4.28 (t, J = 4.8 Hz, 1 H) 3.78 (s, 1 H) 3.71 (t, J = 5.4 Hz, 2 H) 3.34 (s, 2 H) |
| 9.010 | —CF₃ | Me | δ 7.93 (s, 1 H) 7.88 (d, J = 7.0 Hz, 1 H) 7.00 (d, J = 7.5 Hz, 1 H) 3.77 (s, 3 H) 3.69 (s, 3 H) |
| 9.011 | —CF₃ | CH₂=CHCH₂— | δ 8.12 (s, 1 H) 7.85 (d, J = 7.5 Hz, 1 H) 6.84 (d, J = 7.5 Hz, 1 H) 5.93 (m, J = 10.9, 10.9, 5.6 Hz, 1 H) 5.18-5.33 (m, 2 H) 4.78 (d, J = 4.8 Hz, 2H) 3.84 (s, 3H); |
| 9.012 | H |  | 2.48 (3H, s), 3.83 (3H, s), 6.47 (1H, app.t), 6.68 (1H, m), 6.94 (1H, d), 7.68 (1H, d), 7.87 (1H, d), 8.09 (1H, s) |
| 9.013 | H | 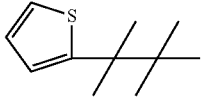 | 3.82 (3H, s), 6.51 (1H, app.t), 7.25 (1H, d), 7.44-7.51 (2H, m), 7.62 (1H, d), 7.91 (1H, d), 8.08 (1H, s) |
| 9.014 | H |  | 3.82 (3H, s), 6.52 (1H, app.t), 7.03 (1H, m), 7.18 (1H, m), 7.28 (1H, m), 7.72 (1H, d), 7.86 (1H, d), 8.08 (1H, s) |
| 9.015 | H | 3Cl,4-F-phenyl- | 3.82 (3H, s), 6.50 (1H, app.t), 7.02 (1H, m), 7.33 (1H, m), 7.42 (1H, d), 7.53 (1H, d), 7.89 (1H, d), 8.03 (1H, s) |
| 9.016 | H | 4-MeO-phenyl- | |

TABLE C9-continued
Examples of herbicidal compounds of the present invention.
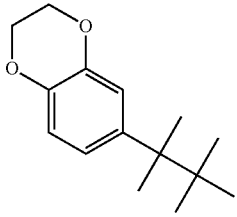 [SMILES: CC(C)(C)C(C)(C)c1ccc2c(c1)OCCO2]
| Compound | R⁶ | R⁹ | NMR |
|---|---|---|---|
| 9.017 | H | 4-Me-phenyl | 3.81 (3H, s), 6.53 (1H, app.t), 7.31-7.59 (6H, m), 7.89 (1H, d), 8.08 (1H, s) |
| 9.018 | H | Phenyl- | 2.53 (3H, s), 3.82 (3H, s), 6.51 (1H, app.t), 7.11 (2H, m), 7.21 (1H, m), 7.51 (1H, d), 7.89 (1H, m), 8.08 (1H, s) |
| 9.019 | H | 3-F,4-Me-phenyl- | 2.41 (3H, s), 3.78 (3H, s), 6.52 (1H, app.t), 7.20 (1H, d), 7.33-3.41 (2H, m), 7.50 (1H, d), 7.89 (1H, d), 8.05 (1H, s) |
| 9.020 | H | 2-Cl,4-Me-phenyl- | 3.79 (3H, s), 6.53 (1H, app.t), 7.47 (1H, d), 7.62 (2H, d), 7.84 (2H, d), 7.91 (1H, d), 8.06 (1H, s) |
| 9.021 | H | 3-CN-phenyl- | |
| 9.022 | H | 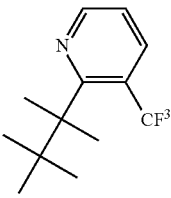 | |
| 9.023 | H | 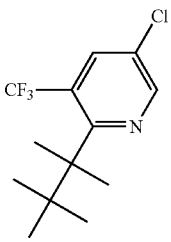 | 3.80 (3H, s), 6.52 (1H, app.t), 7.38 (1H, d), 7.64 (1H, m), 7.94 (1H, d), 8.11 (1H, s), 8.21 (1H, d), 8.89 (1H, s) |
| 9.024 | H | 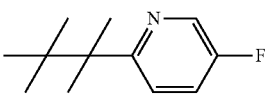 | 3.81 (3H, s), 6.50 (1H, app.t), 7.34 (1H, d), 7.98 (1H, d), 8.09 (1H, s), 8.18 (1H, s), 8.79 (1H, s) |
| 9.025 | H | 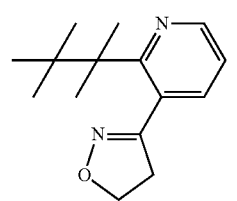 | 3.82 (3H, s), 6.51 (1H, app.t), 7.57 (1H, dd), 7.85 (1H, d), 7.92-8.00 (2H, m), 8.09 (1H, s), 8.41 (1H, s) |
| 9.026 | H |  | |

TABLE C9-continued

Examples of herbicidal compounds of the present invention.

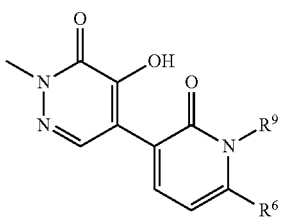

| Compound | R⁶ | R⁹ | NMR |
|---|---|---|---|
| 9.027 | H | | |

TABLE C10

Examples of herbicidal compounds of the present invention.

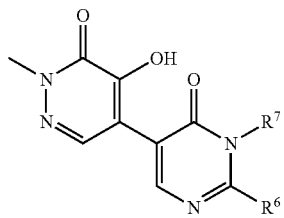

| Compound | R⁶ | R⁷ | NMR |
|---|---|---|---|
| 10.001 | H | —CH₂CH=CH₂ | 3.85 (3 H, s) 4.64 (2 H, d, J = 5.9 Hz) 5.30-5.42 (2 H, m) 5.94-6.06 (1 H, m) 8.13 (1 H, s) 8.14-8.23 (1 H, m) 8.35-8.43 (1 H, m) |
| 10.002 | 3-Cl-phenyl- | nPr | 0.83 (3 H, t, J = 7.5 Hz) 1.70 (2 H, dd, J = 15.6, 7.5 Hz) 3.86 (3 H, s) 3.93-4.00 (2 H, m) 7.39-7.57 (4 H, m) 8.17 (1 H, s) 8.41 (1 H, s) |
| 10.003 | 3-F-phenyl- | chexyl- | 0.95-1.09 (2 H, m) 1.14-1.29 (1 H, m) 1.57 (1 H, d, J = 14.0 Hz) 1.72 (2 H, d, J = 11.8 Hz) 1.81 (2 H, d, J = 12.9 Hz) 2.71 (2 H, td, J = 12.8, 9.4 Hz) 3.85 (3 H, s) 3.90-4.00 (1 H, m) 7.20-7.26 (1 H, m) 7.27-7.30 (1 H, m) 7.52 (1 H, td, J = 7.9, 5.6 Hz) 8.12 (1 H, s) 8.32 (1 H, s) |
| 10.004 | 3-F-phenyl- | 2-Me,5-Cl phenyl- | 2.14 (3 H, s) 3.86 (3 H, s) 7.03-7.14 (4 H, m) 7.16-7.33 (3 H, m) 8.24 (1 H, s) 8.63 (1 H, s) |
| 10.005 | c-propyl | n-butyl | 1.01 (3 H, t, J = 7.3 Hz) 1.14-1.22 (2 H, m) 1.30-1.35 (2 H, m) 1.49 (2 H, dq, J = 15.0, 7.4 Hz) 1.74 -1.85 (2 H, m) 2.01 (1 H, ddd, J = 12.5, 7.9, 4.8 Hz) 3.83 (3 H, s) 4.26-4.33 (2 H, m) 8.07 (1 H, s) 8.21 (1 H, s) |

Biological Examples

Seeds of a variety of test species are sown in standard soil in pots (*Alopecurus myosuroides* (ALOMY), *Setaria faberi* (SETFA), *Echinochloa crus-galli* (ECHCG), *Solanum nigrum* (SOLNI), *Amaranthus retoflexus* (AMARE), *Ipomoea hederacea* (IPOHE)). After cultivation for one day (pre-emergence) or after 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). Compounds are applied at 1000 g/h. The test plants are then grown in a glasshouse under controlled conditions in a glasshouse (at 24/16° C., day/night; 14 hours light; 65% humidity) and watered twice daily. After 13 days for pre and post-emergence, the test is evaluated for the percentage herbicidal damage caused to the plant. The biological activities are shown in the following table on a five point scale (5=80-100% damage; 4=60-79% damage; 3=40-59% damage; 2=20-39% damage; 1=0-19% damage).

TABLE B1

| Compound | POST Application | | | | | | PRE Application | | | | | |
|---|---|---|---|---|---|---|---|---|---|---|---|---|
| | SOLNI | AMARE | SETFA | ALOMY | ECHCG | IPOHE | SOLNI | AMARE | SETFA | ALOMY | ECHCG | IPOHE |
| 1.001 | 5 | 5 | 5 | 5 | 5 | 5 | 5 | 5 | 5 | 5 | 5 | 5 |
| 1.002 | 5 | 3 | 1 | 1 | 1 | 2 | 1 | 1 | 1 | 1 | 1 | 1 |
| 1.003 | 5 | 5 | 5 | 2 | 5 | 5 | 4 | 5 | 1 | 1 | 5 | 3 |
| 1.004 | 5 | 5 | 4 | 1 | 5 | 4 | 1 | 1 | 1 | 1 | 3 | 1 |
| 1.005 | 5 | 5 | 5 | 4 | 5 | 5 | 3 | 5 | 5 | 1 | 5 | 1 |
| 1.006 | 5 | 5 | 1 | 1 | 1 | 5 | 3 | 5 | 1 | 2 | 2 | 3 |
| 1.007 | 5 | 5 | 4 | 4 | 5 | 4 | 2 | 3 | 4 | 1 | 4 | 2 |
| 1.008 | 5 | 5 | 5 | 5 | 5 | 5 | 5 | 4 | 4 | 4 | 5 | 3 |
| 1.009 | 5 | 5 | 5 | 5 | 5 | 5 | 5 | 5 | 5 | 5 | 5 | — |
| 1.010 | 4 | 2 | 1 | 1 | 1 | 4 | 1 | 1 | 1 | 1 | 1 | 1 |
| 1.011 | 4 | 4 | 2 | 2 | 2 | 2 | 1 | 1 | 1 | 1 | 1 | 1 |
| 1.012 | 5 | 5 | 5 | 5 | 5 | 5 | 5 | 5 | 4 | 4 | 5 | 4 |
| 1.013 | 5 | 5 | 5 | 5 | 5 | 5 | 5 | 5 | 5 | 5 | 5 | 4 |
| 1.014 | 5 | 5 | 5 | 5 | 5 | 5 | 5 | 5 | 5 | 5 | 5 | 2 |
| 1.015 | 4 | 2 | 1 | 1 | 2 | 4 | — | — | 1 | 1 | 1 | 1 |
| 1.016 | 3 | 5 | 3 | 2 | 2 | 2 | 1 | 1 | 1 | 1 | 1 | 1 |
| 1.018 | 5 | 5 | 5 | 4 | 5 | 5 | 5 | 5 | 4 | 2 | 5 | 5 |
| 1.021 | 5 | 5 | 1 | 1 | 5 | 5 | 1 | 5 | 1 | 2 | 5 | 2 |
| 1.022 | 3 | 2 | 1 | 1 | 1 | 1 | 1 | 1 | 1 | 1 | 1 | 1 |
| 1.023 | 2 | 3 | 4 | 2 | 1 | 1 | 1 | 5 | 4 | 2 | 1 | 1 |
| 1.024 | 5 | 5 | 3 | 1 | 2 | 4 | 1 | 5 | 1 | 1 | 2 | 4 |
| 1.025 | 4 | 2 | 1 | 1 | 1 | 2 | 1 | 1 | 1 | 1 | 1 | 1 |
| 1.026 | 5 | 5 | 5 | 5 | 5 | 5 | 5 | 5 | 5 | 5 | 5 | 5 |
| 1.027 | 5 | 5 | 5 | 1 | 5 | 5 | 4 | 5 | 3 | 1 | 5 | 1 |
| 1.028 | 5 | 5 | 5 | 5 | 5 | 5 | 5 | 5 | 5 | 5 | 5 | 5 |
| 1.029 | 5 | 5 | 5 | 5 | 5 | 5 | 5 | 5 | 5 | 5 | 5 | 5 |
| 1.030 | 5 | 5 | 2 | 1 | 4 | 3 | 4 | 5 | 1 | 1 | 2 | 1 |
| 1.031 | 5 | 5 | 5 | 2 | 5 | 5 | 2 | 5 | 4 | 1 | 5 | 1 |
| 1.032 | 5 | 5 | 5 | 5 | 5 | 5 | 5 | 5 | 5 | 5 | 5 | 4 |
| 1.033 | 5 | 5 | 1 | 2 | 2 | 5 | 5 | 5 | 1 | 1 | 2 | 1 |
| 1.034 | 5 | 5 | 5 | 4 | 5 | 5 | 5 | 5 | 5 | 2 | 5 | 3 |
| 1.035 | 5 | 5 | 1 | 2 | 5 | 5 | 3 | 5 | 1 | 1 | 5 | 4 |
| 1.036 | 5 | 5 | 5 | 5 | 5 | 5 | 1 | 3 | 2 | 3 | 2 | 1 |
| 1.037 | 5 | 5 | 4 | 4 | 4 | 4 | 5 | 5 | 4 | 4 | 5 | 1 |
| 1.038 | 5 | 5 | 5 | 4 | 4 | 4 | 5 | 5 | 3 | 3 | 5 | 1 |
| 1.039 | 5 | 5 | 5 | 4 | 5 | 5 | 4 | 5 | 3 | 2 | 5 | 5 |
| 1.040 | 5 | 5 | 5 | 4 | 5 | 5 | 5 | 5 | 5 | 5 | 5 | 4 |
| 1.041 | 5 | 5 | 5 | 4 | 5 | 5 | 2 | 4 | 2 | 3 | 4 | 1 |
| 1.042 | 5 | 5 | 5 | 5 | 5 | 4 | 5 | 5 | 5 | 5 | 5 | 1 |
| 1.043 | 5 | 5 | 4 | 2 | 4 | 4 | 1 | 1 | 1 | 1 | 1 | 1 |
| 1.044 | 5 | 5 | 5 | 5 | 5 | 5 | 5 | 5 | 5 | 5 | 5 | 1 |
| 1.045 | 4 | 2 | 1 | 1 | 1 | 1 | 1 | 1 | 1 | 1 | 1 | 1 |
| 1.046 | 5 | 5 | 5 | 5 | 5 | 5 | 5 | 5 | 3 | 5 | 5 | 1 |
| 1.047 | 4 | 3 | 1 | 1 | 1 | 3 | 1 | 1 | 1 | 1 | 1 | 1 |
| 1.049 | 5 | 5 | 5 | 5 | 5 | 5 | 5 | 5 | 3 | 2 | 5 | 1 |
| 1.050 | 5 | 5 | 4 | 2 | 5 | 5 | 3 | 5 | 2 | 1 | 5 | 1 |
| 1.051 | 5 | 5 | 2 | 1 | 2 | 4 | 1 | 5 | 1 | 2 | 4 | 1 |
| 1.052 | 5 | 5 | 5 | 4 | 5 | 5 | 5 | 5 | 4 | 4 | 5 | 1 |
| 1.053 | 5 | 5 | 4 | 5 | 5 | 5 | 5 | 5 | 4 | 5 | 5 | 2 |
| 1.054 | 5 | 5 | 5 | 5 | 5 | 4 | 5 | 5 | 5 | 5 | 5 | 3 |
| 1.055 | 5 | 5 | 1 | 1 | 4 | 4 | 4 | 5 | 1 | 1 | 2 | 2 |
| 1.056 | 5 | 5 | 5 | 5 | 5 | 5 | 4 | 5 | 1 | 5 | 5 | 1 |
| 1.057 | 5 | 5 | 5 | 5 | 5 | 5 | 5 | 5 | 5 | 5 | 5 | 2 |
| 1.058 | 5 | 5 | 5 | 5 | 5 | 5 | 5 | 5 | 5 | 5 | 5 | 5 |
| 1.059 | 5 | 5 | 5 | 5 | 5 | 5 | 5 | 5 | 5 | 5 | 5 | 5 |
| 1.061 | 5 | 5 | 5 | 5 | 5 | 5 | 5 | 5 | 5 | 5 | 5 | 4 |
| 1.062 | 4 | 5 | 4 | 2 | 5 | 5 | 1 | — | 1 | 1 | 1 | 1 |
| 1.063 | 2 | 3 | 1 | 1 | 1 | 3 | 1 | 1 | 1 | 1 | 1 | 1 |
| 1.064 | 5 | 5 | 1 | 1 | 1 | 4 | 1 | 1 | 1 | 1 | 1 | 1 |
| 1.065 | 4 | 5 | 5 | 1 | 5 | 4 | 1 | 5 | 2 | 1 | 3 | — |
| 1.066 | 3 | 1 | 1 | 2 | 1 | 2 | 4 | 4 | 1 | 3 | 2 | 5 |
| 1.067 | 5 | 5 | 4 | 2 | 5 | 5 | 3 | 4 | 1 | 1 | 5 | 2 |
| 1.068 | 5 | 5 | 3 | 3 | 5 | 5 | 4 | 4 | 2 | 2 | 5 | 3 |
| 1.069 | 4 | 5 | 1 | 2 | 5 | 4 | 2 | 2 | 2 | 1 | 5 | 4 |
| 1.070 | 4 | 3 | 4 | 1 | 4 | 1 | 1 | 1 | 1 | 1 | 1 | 1 |
| 1.071 | 5 | 5 | 4 | 3 | 5 | 5 | 5 | 5 | 4 | 4 | 5 | 2 |
| 1.072 | 5 | 5 | 5 | 4 | 5 | 5 | 5 | 5 | 5 | 4 | 5 | 5 |
| 1.073 | 5 | 5 | 5 | 4 | 5 | 5 | 5 | 5 | 5 | 5 | 5 | 2 |
| 1.074 | 5 | 5 | 5 | 2 | 5 | 5 | 1 | 5 | 1 | 2 | 4 | 1 |
| 1.075 | 5 | 5 | 2 | 3 | 5 | 5 | 5 | 5 | 1 | 1 | 5 | 2 |
| 1.076 | 4 | 5 | 1 | 2 | 2 | 4 | 2 | 5 | 1 | 1 | 1 | 1 |
| 1.077 | 2 | 4 | 1 | 1 | 1 | 2 | 3 | 3 | 1 | 1 | 1 | 1 |
| 1.078 | 5 | 5 | 5 | 1 | 5 | 4 | 5 | 5 | 5 | 2 | 5 | 2 |

TABLE B1-continued

| | POST Application | | | | | | PRE Application | | | | | |
|---|---|---|---|---|---|---|---|---|---|---|---|---|
| Compound | SOLNI | AMARE | SETFA | ALOMY | ECHCG | IPOHE | SOLNI | AMARE | SETFA | ALOMY | ECHCG | IPOHE |
| 1.081 | 5 | 5 | 5 | 5 | 5 | 5 | 5 | 5 | 5 | 5 | 5 | 2 |
| 1.082 | 4 | 2 | 1 | 1 | 1 | 2 | 1 | 1 | 1 | 1 | 1 | 1 |
| 1.084 | 4 | 4 | 2 | 1 | 3 | 4 | 1 | 1 | 1 | 1 | 1 | 1 |
| 1.086 | 1 | 1 | 1 | 1 | 1 | 1 | 1 | 1 | 1 | 1 | 1 | 1 |
| 1.088 | 5 | 5 | 1 | 1 | 5 | 1 | 1 | 5 | 1 | 1 | 1 | 1 |
| 1.089 | 1 | 1 | 1 | 1 | 1 | 1 | 1 | 1 | 1 | 1 | 1 | 1 |
| 1.090 | 2 | 1 | 1 | 1 | 1 | 1 | 1 | 1 | 1 | 1 | 1 | 1 |
| 1.091 | 2 | 1 | 1 | 1 | 1 | 1 | 1 | 1 | 1 | 1 | 1 | 1 |
| 1.092 | 2 | 1 | 1 | 1 | 1 | 2 | 1 | 1 | 1 | 1 | 1 | 1 |
| 1.093 | 2 | 1 | 1 | 1 | 1 | 1 | 1 | 1 | 1 | 1 | 1 | 1 |
| 1.094 | 2 | 1 | 1 | 1 | 1 | 1 | 1 | 1 | 1 | 1 | 1 | 1 |
| 1.095 | 1 | 1 | 1 | 1 | 1 | 1 | 1 | 1 | 1 | 1 | 1 | 1 |
| 1.096 | 1 | 1 | 1 | 1 | 1 | 2 | 1 | 1 | 1 | 1 | 1 | 1 |
| 1.098 | 3 | 2 | 1 | 1 | 1 | 2 | 1 | 1 | 1 | 1 | 1 | 1 |
| 1.099 | 2 | 3 | 1 | 1 | 1 | 2 | 1 | 1 | 1 | 1 | 1 | 1 |
| 1.100 | 2 | 2 | 1 | 1 | 1 | 2 | 1 | 1 | 1 | 1 | 1 | 1 |
| 1.101 | 1 | 1 | 1 | 1 | 1 | 1 | 1 | 1 | 1 | 1 | 1 | 1 |
| 1.103 | 2 | 1 | 1 | 1 | 1 | 1 | 1 | 1 | 1 | 1 | 1 | 1 |
| 1.105 | 5 | 5 | 1 | 2 | 5 | 5 | 4 | 5 | 2 | 2 | 5 | 1 |
| 1.106 | 4 | 5 | 2 | 2 | 4 | 2 | 1 | 4 | 1 | 1 | 1 | 1 |
| 1.108 | 3 | 3 | 1 | 1 | 1 | 1 | 1 | 1 | 1 | 1 | 1 | 1 |
| 1.109 | 4 | 5 | 1 | 1 | 2 | 4 | 2 | 5 | 1 | 1 | 1 | 1 |
| 1.110 | 5 | 5 | 1 | 1 | 3 | 5 | 1 | 5 | 1 | 1 | 1 | 1 |
| 1.111 | 3 | 2 | 1 | 1 | 1 | 1 | | | 1 | 1 | 1 | 2 |
| 1.112 | 4 | 5 | 1 | 1 | 1 | 4 | 1 | 1 | 1 | 1 | 1 | 1 |
| 1.113 | 5 | 5 | 3 | 2 | 2 | 5 | 4 | 5 | 1 | 1 | 1 | 2 |
| 1.114 | 1 | 1 | 1 | 1 | 1 | 1 | 1 | 1 | 1 | 1 | 1 | 1 |
| 1.115 | 5 | 2 | 1 | 1 | 1 | 4 | 4 | 4 | 1 | 1 | 2 | |
| 1.116 | 5 | 4 | 2 | 1 | 2 | 4 | 3 | 5 | 2 | 2 | 1 | 1 |
| 1.118 | 3 | 4 | 1 | 1 | 2 | 2 | 1 | 1 | 1 | 1 | 1 | 1 |
| 1.119 | 5 | 5 | 5 | 5 | 5 | 5 | 5 | 5 | 5 | 5 | 5 | 5 |
| 1.120 | 5 | 5 | 5 | 5 | 5 | 5 | 4 | 5 | 4 | 3 | 5 | 4 |
| 1.125 | 5 | 5 | 5 | 5 | 5 | 5 | 4 | 5 | 5 | 4 | 5 | 1 |
| 1.126 | 4 | 5 | 2 | 1 | 2 | 3 | 1 | | 1 | 1 | 1 | 1 |
| 1.128 | 4 | 1 | 2 | 1 | 1 | 3 | 1 | 1 | 1 | 1 | 1 | 1 |
| 1.129 | 3 | 3 | 2 | 1 | 2 | 2 | 1 | 1 | 1 | 1 | 1 | 1 |
| 1.131 | 5 | 5 | 4 | 4 | 5 | 5 | 4 | 3 | 1 | 1 | 1 | 1 |
| 1.133 | 2 | 1 | 1 | 1 | 3 | 2 | 1 | 1 | 1 | 1 | 1 | 1 |
| 1.134 | 5 | 5 | 2 | 1 | 2 | 5 | 5 | 5 | 1 | 1 | 1 | 2 |
| 1.135 | 5 | 5 | 5 | 4 | 5 | 5 | 5 | 5 | 5 | 4 | 5 | 5 |
| 1.137 | 5 | 5 | 5 | 1 | 5 | 5 | 3 | 2 | 1 | 1 | 1 | 1 |
| 1.138 | 5 | 5 | 5 | 1 | 4 | 1 | 1 | 1 | 1 | 1 | 1 | 1 |
| 1.139 | 5 | 5 | 5 | 5 | 5 | 5 | | 5 | 1 | 5 | 5 | 4 |
| 1.140 | 5 | 5 | 3 | 5 | 5 | 5 | 5 | 5 | 1 | 5 | 5 | 2 |
| 1.141 | 5 | 5 | 5 | 5 | 5 | 5 | 5 | 5 | 5 | 5 | 5 | 5 |
| 1.143 | 4 | 1 | 1 | 2 | 2 | 1 | 1 | 3 | 1 | 2 | 1 | 1 |
| 1.144 | 5 | 5 | 5 | 5 | 5 | 5 | 5 | 5 | 4 | 5 | 5 | 4 |
| 1.145 | 5 | 5 | 5 | 3 | 5 | 5 | 2 | 5 | 2 | 1 | 4 | 1 |
| 1.146 | 5 | 5 | 5 | 5 | 5 | 5 | 5 | 5 | 2 | 4 | 5 | 4 |
| 1.147 | 3 | 1 | 1 | 1 | 1 | 1 | 1 | 2 | 2 | 1 | 1 | 1 |
| 1.148 | 3 | 2 | 4 | 1 | 2 | 3 | 1 | 1 | 1 | 1 | 1 | 2 |
| 1.149 | 4 | 4 | 1 | 2 | 1 | 1 | 1 | 1 | 1 | 1 | 1 | 1 |
| 1.150 | 4 | 1 | 1 | 1 | 1 | 1 | 1 | 2 | 1 | 1 | 1 | 2 |
| 1.151 | 5 | 5 | 5 | 5 | 5 | 5 | 4 | 5 | 2 | 2 | 5 | 5 |
| 1.152 | 1 | 1 | 1 | 1 | 1 | 2 | 2 | 2 | 5 | 4 | 2 | 1 |
| 1.153 | 4 | 2 | 1 | 1 | 1 | 2 | 2 | 2 | 1 | 1 | 2 | 3 |
| 1.154 | 5 | 5 | 5 | 4 | 5 | 5 | 2 | 5 | 2 | 2 | 5 | 5 |
| 1.157 | 5 | 5 | 5 | 3 | 5 | 5 | 3 | 5 | 3 | 2 | 5 | 3 |
| 1.158 | 5 | 5 | 5 | 5 | 5 | 5 | 4 | 5 | 3 | 3 | 5 | 3 |
| 1.159 | 5 | 5 | 5 | 4 | 5 | 5 | 5 | 5 | 5 | 5 | 5 | 1 |
| 1.160 | 5 | 5 | 4 | 3 | 5 | 5 | 4 | 5 | 1 | 1 | 5 | 2 |
| 1.161 | 4 | 5 | 4 | 3 | 4 | 2 | 1 | 3 | 1 | 1 | 1 | 1 |
| 1.163 | 5 | 5 | 5 | 5 | 5 | 5 | 5 | 5 | 5 | 5 | 5 | 4 |
| 1.164 | 5 | 5 | 5 | 1 | 5 | 5 | 2 | 3 | 2 | 1 | 4 | 4 |
| 1.165 | 1 | 1 | 1 | 1 | 1 | 1 | 1 | 1 | 1 | 1 | 1 | 1 |

* Applied at 250 g/ha

TABLE B2

| Compound | POST Application | | | | | | PRE Application | | | | | |
|---|---|---|---|---|---|---|---|---|---|---|---|---|
| | SOLNI | AMARE | SETFA | ALOMY | ECHCG | IPOHE | SOLNI | AMARE | SETFA | ALOMY | ECHCG | IPOHE |
| 2.001 | 5 | 5 | 5 | 5 | 5 | 5 | 5 | 5 | 5 | 5 | 5 | 5 |
| 2.002 | 5 | 5 | 5 | 5 | 5 | 5 | 5 | 5 | 5 | 5 | 5 | 5 |
| 2.003 | 5 | 5 | 4 | 3 | 5 | 4 | 1 | 5 | 4 | 3 | 4 | 1 |
| 2.004 | 5 | 5 | 5 | 3 | 5 | 5 | 5 | 5 | 5 | 5 | 5 | 4 |
| 2.005 | 5 | 5 | 5 | 5 | 5 | 5 | 5 | 5 | 5 | 5 | 5 | 5 |
| 2.006 | 5 | 5 | 5 | 5 | 5 | 5 | 5 | 5 | 5 | 5 | 5 | 5 |
| 2.007 | 5 | 5 | 5 | 2 | 5 | 5 | 4 | 5 | 1 | 1 | 5 | 3 |
| 2.008 | 5 | 5 | 5 | 3 | 5 | 5 | 5 | 5 | 2 | 4 | 5 | 3 |
| 2.010 | 5 | 5 | 5 | 5 | 5 | 5 | 5 | 5 | 5 | 5 | 5 | 5 |
| 2.011 | 5 | 5 | 5 | 5 | 5 | 5 | 5 | 5 | 5 | 5 | 5 | 5 |
| 2.012 | 5 | 5 | 5 | 5 | 5 | 5 | 5 | 5 | 5 | 5 | 5 | 5 |
| 2.014 | 5 | 5 | 5 | 5 | 5 | 5 | 5 | 5 | 5 | 5 | 5 | 5 |
| 2.015 | 5 | 5 | 5 | 5 | 5 | 5 | 5 | 5 | 5 | 5 | 5 | 5 |
| 2.016 | 5 | 5 | 5 | 5 | 5 | 5 | 5 | 5 | 5 | 5 | 5 | 5 |
| 2.017 | 5 | 5 | 5 | 5 | 5 | 5 | 5 | 5 | 5 | 5 | 5 | 5 |
| 2.019 | 5 | 5 | 4 | 5 | 4 | 5 | 5 | 5 | 2 | 4 | 5 | 4 |
| 2.020 | 5 | 5 | 4 | 4 | 4 | 5 | 5 | 5 | 1 | 4 | 5 | 1 |
| 2.021 | 5 | 5 | 2 | 1 | 5 | 5 | 1 | 5 | 1 | 1 | 1 | 1 |
| 2.022 | 5 | 5 | 5 | 5 | 5 | 5 | 5 | 5 | 4 | 5 | 5 | 5 |
| 2.023 | 5 | 5 | 5 | 5 | 5 | 5 | 5 | 5 | 1 | 5 | 5 | 4 |
| 2.024 | 5 | 5 | 5 | 5 | 5 | 5 | 4 | 5 | 4 | 5 | 5 | 4 |
| 2.025 | 5 | 5 | 1 | 2 | 4 | 4 | 5 | 5 | 1 | 1 | 1 | 5 |
| 2.026 | 5 | 4 | 3 | 3 | 4 | 2 | 4 | 5 | 1 | 1 | 2 | 1 |
| 2.027 | 5 | 5 | 4 | 4 | 5 | 5 | 3 | 5 | 1 | 2 | 5 | 3 |
| 2.028 | 5 | 5 | 5 | 5 | 5 | 5 | 5 | 5 | 4 | 5 | 5 | 4 |
| 2.029 | 5 | 5 | 5 | 5 | 5 | 5 | 5 | 5 | 3 | 5 | 5 | 1 |
| 2.030 | 5 | 5 | 5 | 5 | 5 | 5 | 5 | 5 | 5 | 5 | 5 | 4 |
| 2.031 | 5 | 5 | 5 | 4 | 5 | 5 | 5 | 5 | 5 | 4 | 5 | 3 |
| 2.032 | 5 | 5 | 4 | 3 | 5 | 5 | 5 | 5 | 2 | 2 | 5 | 3 |
| 2.033 | 5 | 5 | 3 | 5 | 5 | 5 | 5 | 5 | 2 | 4 | 4 | 1 |
| 2.035 | 5 | 5 | 5 | 4 | 5 | 5 | 5 | 5 | 2 | 3 | 3 | 3 |
| 2.036 | 5 | 5 | 5 | 5 | 5 | 5 | 5 | 5 | 5 | 5 | 5 | 5 |
| 2.037 | 5 | 5 | 4 | 3 | 5 | 5 | 5 | 5 | 2 | 3 | 5 | 4 |
| 2.038 | 5 | 5 | 5 | 4 | 5 | 4 | 5 | 5 | 4 | 5 | 5 | 4 |
| 2.039 | 5 | 5 | 5 | 5 | 5 | 5 | 5 | 5 | 5 | 5 | 5 | 5 |
| 2.040 | 5 | 5 | 5 | 5 | 5 | 5 | 5 | 5 | 4 | 5 | 5 | 3 |
| 2.041 | 5 | 5 | 5 | 5 | 5 | 5 | 5 | 5 | 5 | 5 | 5 | 5 |
| 2.043 | 5 | 5 | 4 | 3 | 5 | 5 | 5 | 5 | 1 | 3 | 5 | 2 |
| 2.047 | 5 | 5 | 3 | 3 | 5 | 4 | 4 | 2 | 1 | 1 | 5 | 1 |
| 2.049 | 5 | 5 | 1 | 1 | 5 | 5 | 5 | 5 | 2 | 1 | 5 | 4 |
| 2.050 | 5 | 5 | 5 | 5 | 5 | 5 | 5 | 5 | 5 | 5 | 5 | 5 |
| 2.051 | 5 | 5 | 5 | 5 | 5 | 5 | 5 | 5 | 3 | 5 | 5 | 4 |
| 2.052 | 5 | 5 | 5 | 5 | 5 | 5 | 5 | 5 | 3 | 4 | 5 | 4 |
| 2.053 | 5 | 5 | 2 | 3 | 3 | 5 | 5 | 5 | 2 | 3 | 5 | 1 |
| 2.054 | 5 | 5 | 5 | 5 | 5 | 5 | 5 | 5 | 5 | 5 | 5 | 4 |
| 2.055 | 5 | 5 | 5 | 3 | 5 | 3 | 2 | 4 | 1 | 2 | 2 | 1 |
| 2.056 | 5 | 5 | 5 | 5 | 5 | 5 | 5 | 5 | 5 | 4 | 5 | 3 |

TABLE B3

| Compound | POST Application | | | | | | PRE Application | | | | | |
|---|---|---|---|---|---|---|---|---|---|---|---|---|
| | SOLNI | AMARE | SETFA | ALOMY | ECHCG | IPOHE | SOLNI | AMARE | SETFA | ALOMY | ECHCG | IPOHE |
| 3.001 | 5 | 5 | 5 | 5 | 5 | 5 | 5 | 5 | 5 | 5 | 5 | 5 |
| 3.002 | 5 | 5 | 5 | 5 | 5 | 5 | 5 | 5 | 5 | 5 | 5 | 5 |
| 3.003 | 5 | 5 | 5 | 5 | 5 | 5 | 5 | 5 | 5 | 5 | 5 | 5 |
| 3.004 | 5 | 5 | 5 | 5 | 5 | 5 | 5 | 5 | 5 | 5 | 5 | 5 |
| 3.005 | 5 | 5 | 5 | 5 | 5 | 5 | 5 | 5 | 5 | 5 | 5 | 4 |
| 3.006 | 5 | 5 | 5 | 5 | 5 | 5 | 5 | 5 | 5 | 5 | 5 | 4 |

TABLE B4

| Compound | POST Application | | | | | | PRE Application | | | | | |
|---|---|---|---|---|---|---|---|---|---|---|---|---|
| | SOLNI | AMARE | SETFA | ALOMY | ECHCG | IPOHE | SOLNI | AMARE | SETFA | ALOMY | ECHCG | IPOHE |
| 4.001 | 5 | 5 | 5 | 5 | 5 | 5 | 5 | 5 | 5 | 5 | 5 | 5 |
| 4.003 | 5 | 5 | 5 | 5 | 5 | 5 | 5 | 5 | 5 | 5 | 5 | 5 |
| 4.004 | 5 | 5 | 2 | 1 | 3 | 5 | 3 | 5 | 1 | 1 | 3 | |
| 4.005 | 3 | 5 | 1 | 1 | 1 | 2 | 1 | 5 | 1 | 1 | 1 | 1 |

TABLE B4-continued

| | POST Application | | | | | | PRE Application | | | | | |
|---|---|---|---|---|---|---|---|---|---|---|---|---|
| Compound | SOLNI | AMARE | SETFA | ALOMY | ECHCG | IPOHE | SOLNI | AMARE | SETFA | ALOMY | ECHCG | IPOHE |
| 4.006 | 4 | 3 | 1 | 1 | 1 | 2 | 1 | 1 | 1 | 1 | 1 | 1 |
| 4.008 | 5 | 5 | 2 | 1 | 2 | 4 | 1 | 5 | 1 | 1 | 1 | 1 |
| 4.009 | 5 | 4 | 1 | 1 | 1 | 1 | 1 | 3 | 1 | 1 | 1 | 1 |
| 4.010 | 5 | 5 | 4 | 3 | 5 | 5 | 5 | 5 | 1 | 1 | 5 | 5 |
| 4.011 | 5 | 4 | 1 | 1 | 1 | 3 | 1 | 1 | 1 | 1 | 1 | 1 |
| 4.014 | 5 | 5 | 2 | 1 | 3 | 5 | 4 | 5 | 1 | 1 | 5 | 2 |
| 4.015 | 1 | 1 | 1 | 1 | 1 | 1 | 1 | 1 | 1 | 1 | 1 | 1 |
| 4.016 | 5 | 5 | 5 | 5 | 5 | 5 | 5 | 5 | 5 | 5 | 5 | 5 |
| 4.017 | 5 | 5 | 5 | 5 | 5 | 5 | 5 | 5 | 4 | 4 | 5 | 5 |

TABLE B5

| | POST Application | | | | | | PRE Application | | | | | |
|---|---|---|---|---|---|---|---|---|---|---|---|---|
| Compound | SOLNI | AMARE | SETFA | ALOMY | ECHCG | IPOHE | SOLNI | AMARE | SETFA | ALOMY | ECHCG | IPOHE |
| 5.001 | 5 | 5 | 5 | 5 | 5 | 5 | 5 | 5 | 5 | 5 | 5 | 5 |
| 5.002 | 5 | 5 | 2 | 1 | 3 | 5 | 1 | 5 | 1 | 1 | 2 | 3 |

TABLE B6

| | POST Application | | | | | | PRE Application | | | | | |
|---|---|---|---|---|---|---|---|---|---|---|---|---|
| Compound | SOLNI | AMARE | SETFA | ALOMY | ECHCG | IPOHE | SOLNI | AMARE | SETFA | ALOMY | ECHCG | IPOHE |
| 6.001 | 5 | 5 | 3 | 3 | 5 | 1 | 1 | 1 | 1 | 1 | 1 | 1 |
| 6.002 | 3 | 4 | 1 | 1 | 1 | 2 | 5 | 5 | 1 | 1 | 1 | 2 |
| 6.003 | 4 | 4 | 2 | 2 | 4 | 2 | 1 | 1 | 1 | 1 | 1 | 1 |

TABLE B7

| | POST Application | | | | | | PRE Application | | | | | |
|---|---|---|---|---|---|---|---|---|---|---|---|---|
| Compound | SOLNI | AMARE | SETFA | ALOMY | ECHCG | IPOHE | SOLNI | AMARE | SETFA | ALOMY | ECHCG | IPOHE |
| 7.001 | 4 | 3 | 3 | 2 | 4 | 2 | 1 | 1 | 1 | 1 | 1 | 1 |
| 7.003 | 5 | 5 | 3 | 4 | 5 | 3 | 5 | 5 | 4 | 4 | 4 | 3 |
| 7.005 | 5 | 5 | 4 | 4 | 5 | 4 | 5 | 5 | 4 | 4 | 5 | 1 |
| 7.006 | 5 | 4 | 3 | 3 | 5 | 3 | 5 | 5 | 4 | 3 | 5 | 2 |
| 7.007 | 5 | 5 | 5 | 5 | 5 | 5 | 5 | 5 | 5 | 5 | 5 | 4 |
| 7.009 | 5 | 5 | 5 | 5 | 5 | 5 | 5 | 5 | 5 | 5 | 5 | 4 |
| 7.010 | 5 | 5 | 5 | 5 | 5 | 5 | 5 | 5 | 5 | 5 | 5 | 5 |
| 7.011 | 5 | 5 | 3 | 1 | 5 | 3 | 5 | 5 | 2 | 2 | 1 | 2 |
| 7.012 | 5 | 5 | 5 | 5 | 5 | 5 | 5 | 5 | 5 | 5 | 5 | 1 |
| 7.014 | 5 | 5 | 4 | 1 | 5 | 3 | 5 | 5 | 4 | 3 | 3 | 1 |
| 7.015 | 5 | 5 | 3 | 2 | 4 | 3 | 5 | 5 | 4 | 3 | 3 | 4 |
| 7.016 | 5 | 5 | 2 | 2 | 2 | 1 | 5 | 5 | 2 | 2 | 2 | 1 |
| 7.017 | 5 | 5 | 5 | 5 | 5 | 5 | 5 | 5 | 5 | 5 | 5 | 4 |
| 7.018 | 5 | 5 | 5 | 5 | 5 | 3 | 5 | 5 | 5 | 5 | 5 | 2 |
| 7.019 | 5 | 5 | 5 | 5 | 5 | 2 | 5 | 5 | 5 | 5 | 5 | 2 |
| 7.021 | 5 | 5 | 5 | 5 | 5 | 4 | 5 | 5 | 5 | 5 | 5 | 4 |
| 7.022 | 5 | 5 | 5 | 4 | 5 | 2 | 5 | 5 | 5 | 5 | 5 | 2 |
| 7.023 | 5 | 5 | 4 | 1 | 4 | 1 | 5 | 5 | 4 | 2 | 2 | 2 |
| 7.027 | 5 | 5 | 5 | 3 | 5 | 2 | 5 | 5 | 3 | 3 | 5 | 1 |
| 7.029 | 5 | 5 | 2 | 3 | 5 | 4 | 5 | 5 | 1 | 2 | 2 | 1 |
| 7.030 | 5 | 5 | 5 | 5 | 5 | 5 | 5 | 5 | 4 | 5 | 5 | 4 |
| 7.031 | 5 | 5 | 5 | 5 | 5 | 5 | 5 | 5 | 5 | 5 | 5 | 5 |
| 7.032 | 5 | 5 | 5 | 3 | 5 | 5 | 5 | 5 | 5 | 4 | 5 | 5 |
| 7.033 | 5 | 5 | 5 | 5 | 5 | 3 | 5 | 5 | 5 | 5 | 5 | 4 |
| 7.034 | 5 | 5 | 5 | 1 | 3 | 2 | 5 | 5 | 1 | 2 | 1 | 1 |
| 7.035 | 5 | 5 | 5 | 5 | 5 | 4 | 5 | 5 | 5 | 5 | 5 | 3 |
| 7.036 | 5 | 5 | 3 | 2 | 4 | 4 | 5 | 5 | 2 | 2 | 1 | 4 |
| 7.038 | 5 | 5 | 3 | 5 | 5 | 5 | 5 | 5 | 3 | 5 | 5 | 4 |

TABLE B8

| Compound | POST Application | | | | | | PRE Application | | | | | |
|---|---|---|---|---|---|---|---|---|---|---|---|---|
| | SOLNI | AMARE | SETFA | ALOMY | ECHCG | IPOHE | SOLNI | AMARE | SETFA | ALOMY | ECHCG | IPOHE |
| 8.001 | 5 | 5 | 2 | 1 | 5 | 5 | 5 | 5 | 2 | 1 | 5 | 3 |

TABLE B9

| Compound | POST Application | | | | | | PRE Application | | | | | |
|---|---|---|---|---|---|---|---|---|---|---|---|---|
| | SOLNI | AMARE | SETFA | ALOMY | ECHCG | IPOHE | SOLNI | AMARE | SETFA | ALOMY | ECHCG | IPOHE |
| 9.001 | 4 | 3 | 4 | 4 | 4 | 1 | 1 | 2 | 1 | 3 | 2 | 1 |
| 9.002 | 5 | 4 | 2 | 1 | 2 | 2 | 1 | 1 | 1 | 1 | 1 | 1 |
| 9.003 | 4 | 4 | 2 | 1 | 1 | 2 | 1 | 2 | 1 | 1 | 1 | 1 |
| 9.004 | 4 | 4 | 1 | 1 | 1 | 3 | 1 | 1 | 1 | 1 | 1 | 1 |
| 9.005 | 4 | 2 | 1 | 1 | 1 | 2 | 1 | 1 | 1 | 1 | 1 | 1 |
| 9.006 | 3 | 3 | 2 | 2 | 1 | 2 | 1 | 1 | 1 | 1 | 1 | 1 |
| 9.007 | 4 | 3 | 2 | 1 | 1 | 2 | 1 | 1 | 1 | 1 | 1 | 1 |
| 9.008 | 3 | 3 | 1 | 1 | 1 | 1 | 2 | 2 | 1 | 1 | 4 | 1 |
| 9.009 | 5 | 4 | 3 | 2 | 3 | 3 | 1 | 1 | 1 | 1 | 1 | 1 |
| 9.010 | 5 | 5 | 2 | 2 | 4 | 4 | 1 | 5 | 1 | 1 | 5 | 1 |
| 9.011 | 5 | 5 | 5 | 4 | 5 | 4 | 1 | 4 | 3 | 2 | 5 | 1 |
| 9.016 | 5 | 5 | 3 | 3 | 4 | 2 | 1 | 1 | 1 | 2 | 1 | 1 |
| 9.017 | 4 | 3 | 2 | 2 | 5 | 2 | 1 | 1 | 1 | 2 | 1 | 2 |

TABLE B10

| Compound | POST Application | | | | | | PRE Application | | | | | |
|---|---|---|---|---|---|---|---|---|---|---|---|---|
| | SOLNI | AMARE | SETFA | ALOMY | ECHCG | IPOHE | SOLNI | AMARE | SETFA | ALOMY | ECHCG | IPOHE |
| 10.002 | 5 | 5 | 1 | 1 | 2 | 4 | 1 | 4 | 1 | 1 | 1 | 1 |
| 10.003 | 5 | 5 | 4 | 1 | 5 | 4 | 1 | 5 | 1 | 1 | 1 | 1 |
| 10.004 | 5 | 5 | 3 | 1 | 4 | 4 | 1 | 2 | 1 | 1 | 1 | 1 |
| 10.005 | 5 | 5 | 5 | 2 | 5 | 4 | 5 | 5 | 1 | 1 | 2 | 1 |

The invention claimed is:

1. A compound Formula (I):

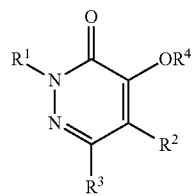

(I)

or an agronomically acceptable salt thereof,
wherein:—
$R^1$ is selected from the group consisting of hydrogen, $C_1$-$C_6$alkyl, $C_3$-$C_6$cycloalkyl, $C_2$-$C_6$alkenyl, $C_2$-$C_6$alkynyl, $C_1$-$C_6$haloalkyl, $C_1$-$C_6$alkoxy-$C_1$-$C_3$-alkyl, $C_3$-$C_6$cycloalkyl$C_1$-$C_3$-alkyl-, and tetrahydropyranyl-;
$R^2$ is selected from the group consisting of A1, A2 and A3

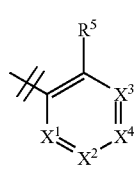

(A1)

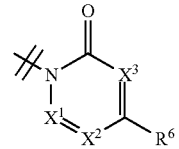

(A2)

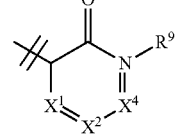

(A3)

wherein
$X^1$ is N or $CR^7$;
$X^2$ is N or $CR^8$;
$X^3$ is N or $CR^9$;
$X^4$ is N or $CR^6$;
$R^3$ is selected from the group consisting of hydrogen, halo, nitro, amino, cyano, $C_1$-$C_6$alkyl, $C_1$-$C_3$alkoxy-, $C_3$-$C_6$cycloalkyl, $C_2$-$C_6$alkenyl, $C_2$-$C_6$alkynyl, $C_1$-$C_6$haloalkyl, $C_1$-$C_6$alkoxy-$C_1$-$C_3$-alkyl, $C_3$-$C_6$cycloalkyl-$C_1$-$C_3$-alkyl, $C_1$-$C_6$alkyl-S(O)$_p$-, $C_1$-$C_6$alkyl-S(O)$_p$-$C_1$-$C_3$-alkyl, $C_1$-$C_6$haloalkyl-S(O)$_p$-, $C_1$-$C_3$alkylamino, $C_1$-$C_3$dialkylamino and $C_1$-$C_6$haloalkyl-S(O)$_p$-$C_1$-$C_3$-alkyl;
$R^4$ is selected from the group consisting of hydrogen, $C_1$-$C_6$alkylcarbonyl-, arylcarbonyl-, $C_1$-$C_6$alkoxycarbonyl-, $C_1$-$C_6$alkyl-$S(O)_p$-, $C_1$-$C_6$alkyl-$S(O)_p$carbonyl- and aryl-$S(O)_p$-, wherein said aryl groups may be optionally substituted by one or more $R^{11}$;

$R^5$ is selected from the group consisting of hydroxyl, halogen, $C_1$-$C_6$alkyl, $C_1$-$C_6$cycloalkyl, $C_1$-$C_6$haloalkyl, $C_2$-$C_6$alkenyl, $C_2$-$C_6$haloalkenyl, $C_2$-$C_6$alkynyl, $C_1$-$C_6$ alkoxy-, $C_2$-$C_6$ alkenyloxy-, $C_3$-$C_6$cycloalkyl$C_1$-$C_3$-alkyl-, $C_1$-$C_6$ alkoxy$C_1$-$C_3$alkyl-, $C_1$-$C_6$ alkoxy-$C_2$-$C_6$alkoxy-, $C_1$-$C_6$ alkoxy-$C_2$-$C_6$alkoxy-$C_1$-$C_3$alkyl-, $C_1$-$C_6$ haloalkoxy-, $C_1$-$C_6$ haloalkoxy-$C_1$-$C_3$alkyl-, $C_1$-$C_6$alkyl-$S(O)_p$-, $C_1$-$C_6$haloalkyl-$S(O)_p$-, aryl, aryl-$S(O)_p$-, heterocyclyl, heterocyclyl-$S(O)_p$-, aryloxy-, aryl-$C_2$-$C_6$alkyl-, aryl-$C_1$-$C_6$alkoxy-, heterocyclyloxy-, heterocyclyl-$C_1$-$C_3$alkoxy-$C_1$-$C_3$alkyl-, hydroxycarbonyl, hydroxycarbonyl-$C_1$-$C_3$ alkoxy-, $C_1$-$C_3$ alkoxycarbonyl-, $C_1$-$C_3$ alkoxycarbonyl-$C_1$-$C_3$ alkoxy-, $C_1$-$C_3$alkylamino-, $C_1$-$C_3$dialkylamino-, $C_1$-$C_3$ alkylamino-$S(O)_p$-, $C_1$-$C_3$ alkylamino-$S(O)_p$-$C_1$-$C_3$alkyl-, $C_1$-$C_3$ dialkylamino-$S(O)_p$-, $C_1$-$C_3$ dialkylamino-$S(O)_p$- $C_1$-$C_3$alkyl-, $C_1$-$C_3$alkylaminocarbonyl-, $C_1$-$C_3$alkylaminocarbonyl-$C_1$-$C_3$alkyl-, $C_1$-$C_3$dialkylaminocarbonyl-, $C_1$-$C_3$ dialkylaminocarbonyl-$C_1$-$C_3$alkyl-, $C_1$-$C_3$alkylcarbonylamino-, $C_1$-$C_3$ alkyl-$S(O)_p$-amino-, $C_1$-$C_3$alkyl-$S(O)_p$-$C_1$-$C_3$alkylamino-, $C_1$-$C_3$alkyl-$S(O)_p$- amino$C_1$-$C_3$alkyl-, cyano and nitro, wherein said heterocyclyls are five or six membered heterocyclyls containing from one to three heteroatoms each independently selected from the group consisting of oxygen, nitrogen and sulphur, and wherein the aryl or heterocyclyl components may be optionally substituted by one or more substituents selected from the group consisting of halo, $C_1$-$C_3$alkyl, $C_1$-$C_3$haloalkyl, $C_1$-$C_3$ alkoxy, $C_1$-$C_3$ haloalkoxy, $C_1$-$C_6$alkyl-$S(O)_p$-, phenyl, cyano and nitro;

$R^6$ and $R^9$ are independently selected from the group consisting of hydrogen, hydroxyl, halogen, $C_1$-$C_6$alkyl, $C_1$-$C_6$cycloalkyl, $C_1$-$C_6$haloalkyl, $C_2$-$C_6$alkenyl, $C_2$-$C_6$haloalkenyl, $C_2$-$C_6$alkynyl, $C_1$-$C_6$ alkoxy-, $C_2$-$C_6$ alkenyloxy-, $C_3$-$C_6$cycloalkyl$C_1$-$C_3$-alkyl-, $C_1$-$C_6$ alkoxy$C_1$-$C_3$alkyl-, $C_1$-$C_6$ alkoxy-$C_2$-$C_6$alkoxy-, $C_1$-$C_6$ alkoxy-$C_2$-$C_6$alkoxy-$C_1$-$C_3$alkyl-, $C_1$-$C_6$ haloalkoxy-, $C_1$-$C_6$ haloalkoxy-$C_1$-$C_3$alkyl-, $C_1$-$C_6$alkyl-$S(O)_p$-, $C_1$-$C_6$haloalkyl-$S(O)_p$-, aryl, aryl-$S(O)_p$-, heterocyclyl, heterocyclyl-$S(O)_p$-, aryloxy-, aryl-$C_2$-$C_6$alkyl-, aryl-$C_1$-$C_6$alkoxy-, heterocyclyloxy-, heterocyclyl-$C_1$-$C_3$alkoxy-$C_1$-$C_3$alkyl-, hydroxycarbonyl, hydroxycarbonyl-$C_1$-$C_3$alkoxy-, $C_1$-$C_3$ alkoxycarbonyl-, $C_1$-$C_3$alkoxycarbonyl-$C_1$-$C_3$ alkoxy-, $C_1$-$C_3$alkylamino-, $C_1$-$C_3$dialkylamino-, $C_1$-$C_3$alkylamino-$S(O)_p$-, $C_1$-$C_3$ alkylamino-$S(O)_p$-$C_1$-$C_3$alkyl-, $C_1$-$C_3$ dialkylamino-$S(O)_p$-, $C_1$-$C_3$ dialkylamino-$S(O)_p$-$C_1$-$C_3$alkyl-, $C_1$-$C_3$alkylaminocarbonyl-, $C_1$-$C_3$alkylaminocarbonyl-$C_1$-$C_3$alkyl-, $C_1$-$C_3$dialkylaminocarbonyl-, $C_1$-$C_3$ dialkylaminocarbonyl-$C_1$-$C_3$alkyl-, $C_1$-$C_3$alkylcarbonylamino-, $C_1$-$C_3$ alkyl-$S(O)_p$-amino-, $C_1$-$C_3$alkyl-$S(O)_p$-$C_1$-$C_3$alkylamino-, $C_1$-$C_3$alkyl-$S(O)$ p- amino$C_1$-$C_3$alkyl-, cyano and nitro, wherein said heterocyclyls are five or six membered heterocyclyls containing from one to three heteroatoms each independently selected from the group consisting of oxygen, nitrogen and sulphur, and wherein the aryl or heterocyclyl components may be optionally substituted by one or more substituents selected from the group consisting of halo, $C_1$-$C_3$alkyl, $C_1$-$C_3$haloalkyl, $C_1$-$C_3$ alkoxy, $C_1$-$C_3$ haloalkoxy, $C_1$-$C_6$alkyl-$S(O)_p$-, phenyl, cyano and nitro;

$R^7$ and $R^8$ are independently selected from the group consisting of hydrogen, halogen, $C_1$-$C_3$ alkyl-, $C_1$-$C_3$ alkoxy-, $C_2$-$C_3$alkenyl-, $C_2$-$C_3$alkynyl-, $C_1$-$C_3$ haloalkyl- and $C_1$-$C_3$haloalkoxy-;

and wherein $R^5$ and $R^9$ can together form a saturated or unsaturated 5- or 6-membered carbocyclic or heterocyclic ring, said heterocyclic ring comprising one or more nitrogen and/or oxygen heteroatoms, the 5- or 6-membered ring being optionally substituted by one or more $R^{12}$; or $R^6$ and $R^9$ can together form a saturated or unsaturated 5- or 6-membered carbocyclic or heterocyclic ring, said heterocyclic ring comprising one or more hetereoatoms selected from the group consisting of nitrogen, oxygen and $S(O)_2$, the 5- or 6-membered ring being optionally substituted by one or more $R^{12}$; or $R^6$ and $R^8$ can together form a saturated or unsaturated 5- or 6-membered carbocyclic or heterocyclic ring, said heterocyclic ring comprising one or more nitrogen heteroatoms, the 5- or 6-membered ring being optionally substituted by one or more $R^{13}$; and $R^{11}$ is selected from the group consisting of halo-, $C_1$-$C_3$alkyl, $C_1$-$C_3$ haloalkyl and $C_1$-$C_6$alkoxy;

$R^{12}$ is selected from the group of hydrogen, cyano, halo-, oxy-, $C_1$-$C_3$alkylS(O)p-, $C_1$-$C_3$ alkyl, $C_2$-$C_3$alkenyl, $C_2$-$C_3$alkynyl, $C_1$-$C_3$ alkoxy and $C_1$-$C_3$ haloalkyl;

$R^{13}$ is selected from the group of hydrogen, cyano, halo-, $C_1$-$C_3$alkylS(O)p-, $C_1$-$C_3$ alkyl, $C_2$-$C_3$alkenyl, $C_2$-$C_3$alkynyl, morpholinyl- and $C_1$-$C_3$ haloalkyl; and =0, 1 or 2.

2. A compound according to claim 1, wherein $R^3$ and/or $R^4$ is hydrogen.

3. A compound according to claim 1, wherein $R^2$ is selected from the group consisting of A1a, A1b, A1c, A1d, A1e, A1f, A1g, A1h, A2a, A2b, A3a A3b and A3 c:

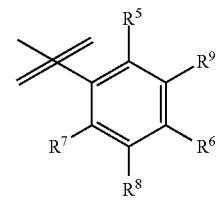

(A1a)

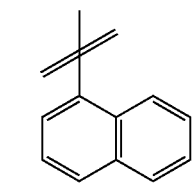

(A1b)

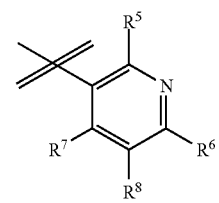

(A1c)

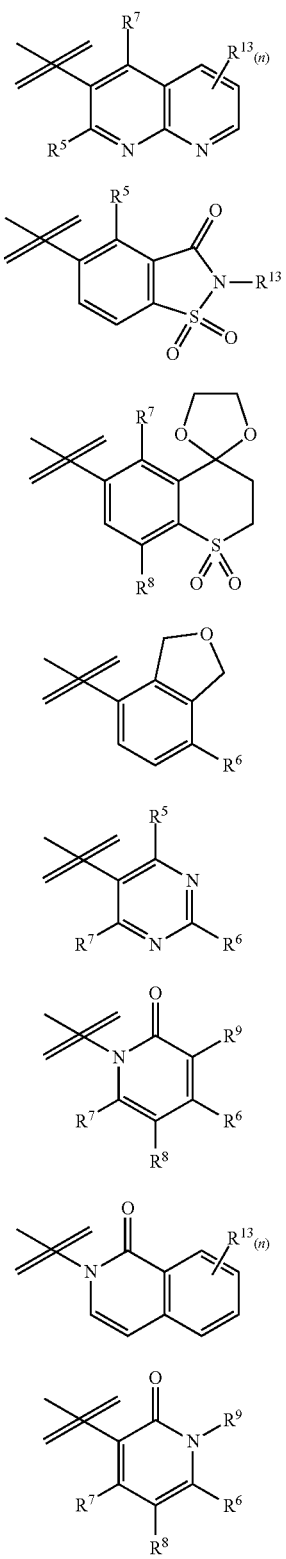

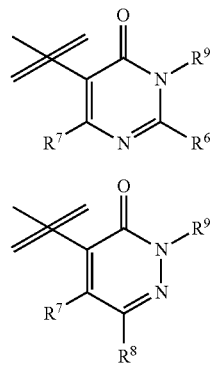

wherein $R^5$, $R^6$, $R^7$, $R^8$, $R^9$ and $R^{13}$ are as defined previously and n is 0, 1, 2 or 3.

4. A compound according to claim 3, wherein $R^2$ is A1a.

5. A compound according to claim 1, wherein $R^5$ is selected from the group consisting of hydroxyl, halo, $C_1$-$C_6$alkyl, $C_1$-$C_6$cycloalkyl, $C_1$-$C_6$haloalkyl, $C_1$-$C_6$ alkoxy, $C_1$-$C_6$ alkoxyC$_1$-C$_3$alkyl, $C_1$-$C_6$ alkoxy-C$_2$-C$_6$alkoxy-C$_1$-C$_3$alkyl, $C_1$-$C_6$ haloalkoxyC$_1$-C$_3$alkyl, $C_1$-$C_6$alkyl-S(O)$_p$-, aryl, aryloxy, heterocyclyl-C$_1$-C$_3$alkoxy-C$_1$-C$_3$alkyl, $C_1$-$C_3$dialkylamino-, $C_1$-$C_3$alkyl-S(O)$_p$-amino-C$_1$-C$_3$dialkyl, cyano and nitro.

6. A compound according to claim 5, wherein $R^5$ is selected from the group consisting of chloro, fluoro, methyl, trifluoromethyl, 2-fluoroethyl-, methoxyethoxymethyl-, trifluoromethoxymethyl-, methylS(O)$_p$-, aryl, isoxazolinyl, morpholinyl, methyl-S(O)$_p$-dimethylamino-, cyano and nitro, wherein the aryl or heterocyclyl components may be optionally substituted by one or more substituents selected from the group consisting of chloro, methyl or trifluoromethyl.

7. A compound according to claim 1, wherein $R^6$ is selected from the group consisting of hydrogen, halogen, $C_1$-$C_6$alkyl, $C_1$-$C_6$haloalkyl, $C_1$-$C_6$alkyl-S(O)$_p$-, $C_2$-$C_6$alkenyl and $C_2$-$C_6$alkynyl.

8. A compound according to claim 1, wherein $R^7$ and $R^8$ are independently selected from the group consisting of hydrogen, halogen and $C_1$-$C_3$ alkyl-.

9. A compound according to claim 1, wherein $R^9$ is selected from the group consisting of hydrogen, halogen, $C_1$-$C_6$alkyl, $C_1$-$C_6$haloalkyl, $C_1$-$C_6$alkyl-S(O)$_p$-, $C_2$-$C_6$alkenyl and $C_2$-$C_6$alkynyl.

10. A herbicidal composition comprising a herbicidal compound according to claim 1 and an agriculturally acceptable formulation adjuvant.

11. A herbicidal composition according to claim 10, further comprising at least one additional pesticide.

12. A herbicidal composition according to claim 11, wherein the additional pesticide is a herbicide or herbicide safener.

13. A method of controlling weeds at a locus comprising application to the locus of a weed controlling amount of a composition comprising a compound of Formula (I) as described in claim 1 or an agronomically acceptable salt thereof.

* * * * *